(12) United States Patent
Konradi et al.

(10) Patent No.: US 8,138,272 B2
(45) Date of Patent: Mar. 20, 2012

(54) PREPARATION OF POLYMER CONJUGATES OF THERAPEUTIC, AGRICULTURAL, AND FOOD ADDITIVE COMPOUNDS

(75) Inventors: Andrei W. Konradi, Burlingame, CA (US); Jenifer L. Smith, South San Francisco, CA (US)

(73) Assignee: Elan Pharmaceuticals, Inc., South San Francisco, CA (US)

(*) Notice: Subject to any disclaimer, the term of this patent is extended or adjusted under 35 U.S.C. 154(b) by 449 days.

(21) Appl. No.: 11/752,063

(22) Filed: May 22, 2007

(65) Prior Publication Data

US 2008/0031848 A1    Feb. 7, 2008

Related U.S. Application Data

(60) Provisional application No. 60/802,349, filed on May 22, 2006.

(51) Int. Cl.
*C08G 73/00* (2006.01)
(52) U.S. Cl. .............. 525/440.06; 525/437; 525/523
(58) Field of Classification Search .......... 525/437, 525/440.06, 523
See application file for complete search history.

(56) References Cited

U.S. PATENT DOCUMENTS

| | | | |
|---|---|---|---|
| 4,507,466 A | 3/1985 | Tomalia et al. | |
| 4,631,337 A | 12/1986 | Tomalia et al. | |
| 4,960,832 A * | 10/1990 | Arnold et al. | 525/328.8 |
| 5,041,516 A | 8/1991 | Frechet et al. | |
| 5,177,059 A | 1/1993 | Handley et al. | |
| 5,530,092 A | 6/1996 | Meijer et al. | |
| 5,824,701 A | 10/1998 | Greenwald et al. | |
| 5,880,131 A | 3/1999 | Greenwald et al. | |
| 6,664,331 B2 | 12/2003 | Harris et al. | |
| 6,716,821 B2 | 4/2004 | Zhao et al. | |
| 2003/0149104 A1 * | 8/2003 | Boije et al. | 514/532 |
| 2004/0043040 A1 | 3/2004 | Dunussi-Joannopoulos | |
| 2006/0013799 A1 * | 1/2006 | Konradi et al. | 424/78.27 |
| 2007/0021555 A1 * | 1/2007 | Konradi et al. | 525/54.1 |

FOREIGN PATENT DOCUMENTS

| | | |
|---|---|---|
| WO | 0154690 | 8/2001 |
| WO | 2004000366 | 12/2003 |
| WO | WO 2004010957 A2 * | 2/2004 |
| WO | 2005070921 | 8/2005 |
| WO | WO 2005111020 A2 * | 11/2005 |
| WO | 2006010054 | 1/2006 |
| WO | 2007008563 | 1/2007 |
| WO | WO 2007008563 A2 * | 1/2007 |
| WO | 2007137260 | 11/2007 |
| WO | WO 2009075806 A1 * | 6/2009 |

OTHER PUBLICATIONS

Huryn et al, Synthesis, Characterization and evaluation of pro-drugs of VLA-4 antagonists, Bioorganic & Medicinal Chemistry Letters, 14, 2004, 1651-1654.*
Porter et al, N-pyrimidin-4-yl and N-pyridine-2-yl phenylalanine derivatives as VLA-4 integrin antagonists, Bioorganic & Medicinal Chemistry Letters, 12, 2002, 1595-1598.*
Macchiarulo et al, Insights into phenylalanine derivatives recognition of VLA-4 integrin: from a pharmacophoric study to 3D-QSAR and molecular docking analysis, J. Chem. Inf. Comput. Sci. 2004, 44, 1829-1839.*
Pepinksy et al, Design, synthesis and analysis of a polyethylene glycol modified (PEGylated) small molecule inhibitor of integrin alpha4beta1 with improved pharmaceutical properties, Journal of Pharmacology and Experimental Therapeutics, 312, 2, 2005, 742-750.*
Chirakul et al, Synthesis and characterization of amine terminated self-assembled monolayers containing diethylene glycol linkages, Langmuir, 2002, 18, 4324-4330.*
Pepinsky RB et al., "Design, Synthesis, and Analysis of a Polyethelene Glycol-Modified (Pegylated) Small Molecule Inhibitor of Integrin .AlPHA.4.BETA.1 with Improved Pharmaceutical Properties," Journal of Pharmacology and Experimental Therapeutics, American Society for Pharmacology, 312(2), 742-750 (2005).
Zaplinsky et al., "Attachment of Drugs to Polyethylene Glycols," Eur. Polym. J., 19, No. 12, p. 1177-1183 (1983).
Zaplinsky, "Chemistry of polyethylene glycol conjugates with biologically active molecules," Advanced Drug Delivery Reviews, 16, 157-182 (199.
Veronese et al., "Preparation, Physico-Chemical and Pharmacokinetic Characterization of Monomethoxypoly(ethylene Glycol)-Derivatized Superoxide Dismutase," Journal of Controlled Release, 19:145-154 (1989).
Kameda, Y. et al., "The use of PVP as a polymeric carrier to improve the plasma half-life of drugs," Biomaterials, 25:3259-3266 (2004).
Thanou, M. et al., "Polymer-Protein and polymer-drug conjugates in cancer therapy," Current Opinion in Investigational Drugs 4(6): 701-709 (2003).
Veronese et al., "Bioconjugation in pharmaceutical chemistry," IL Farmaco, 54:497-516 (1999).

(Continued)

*Primary Examiner* — Alicia Toscano
(74) *Attorney, Agent, or Firm* — McDonnell Boehnen Hulbert & Berghoff LLP

(57) ABSTRACT

This invention provides an improved synthesis of polymer conjugates of formula (I),

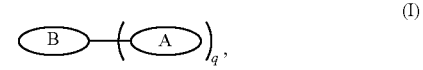

of agricultural, therapeutic, and food additive compounds. In particular, a process is described for the preparation of conjugates by treating primary or secondary alcohol substituents of active compounds with polymeric nucleophiles using "Mitsunobu" or related reaction conditions.

42 Claims, No Drawings

OTHER PUBLICATIONS

Gunatillake et al., "Thermal Polymerization of a 2-(carboxyalkyl)-2-oxazoline," Macromolecules, 21, 1556-1562 (1988).

Hawker et al., "One-Step Synthesis of Hyperbranched Dendritic Polyesters," J. Am. Chem. Soc., 113, 4583-4588 (1991).

Tomalia et al., "Discovery of Dendrimers and Dendritic Polymers: A Brief Historical Perspective," J. Polym. Sci Part A: Polym. Chem., 40, 2719-2728 (2002).

Boas et al., "Dendrimers in drug research," Chem. Soc. Rev., 33, 43-63 (2004).

Sakamoto et al. "Preparation of (Cyanomethylene)trimethylphosphorane as a New Mitsunobu-Type Reagent" Chem. Pharm. Bull. 51(4), 474-476 (2003).

Swamy et al. "Mitsunobu and Related Reactions: Advances and Applications" Chem. Rev. 109, 2551-2651 (2009).

Andrew L. Ternay, Jr. Contemporary Organic Chemistry. Philadelphia: W. B. Saunders Company, 1979; p. 388.

L. G. Wage, Jr. Organic Chemistry. Englewood Cliffs: Prentice-Hall, Inc., 1991; p. 365.

* cited by examiner

PREPARATION OF POLYMER CONJUGATES OF THERAPEUTIC, AGRICULTURAL, AND FOOD ADDITIVE COMPOUNDS

This application claims priority of U.S. application Ser. No. 60/802,349, filed May 22, 2006, the disclosure of which is incorporated herein in its entirety.

BACKGROUND OF THE INVENTION

1. Field of the Invention

This invention relates to processes for making polymer conjugates of therapeutic, agricultural, and food additive compounds. More specifically, the invention relates to processes employing "Mitsunobu" reaction conditions to prepare conjugates for use in treating various mammalian, particularly human, diseases and disorders as well as in agriculture and as food additives. In certain aspects, the invention relates to using "Mitsunobu" conditions with an alcohol, particularly a primary or secondary alcohol-containing active compound, and a polymeric nucleophile to form the desired conjugates.

2. Description of the Related Art

Attachment of biologically active compounds to polymers has received significant attention and has become a common method to control various characteristics, e.g., biodistribution, pharmacokinetics, and toxicity, of such compounds. A frequent choice of polymer for use in making polymer conjugates of biologically active compounds is polyethylene glycol (PEG). It is widely used as a covalent modifier of both small and large biologically active molecules. For discussions of such conjugates, see, Eur. Polym. J. 19, No. 12, pages. 1177-1183 (Zaplinsky et al., 1983) et al., Journal of Controlled Release 10 (1989) 145-154 (Veronese et al., 1989), and Advanced Drug Delivery Reviews, 16, 157-182 (Zaplinsky, 1995).

It has recently been discovered that polymer conjugates of, for example, $\alpha_4\beta_1$ (VLA-4) antagonists have greatly improved serum half-life. These polymer compounds can be prepared using various synthetic methods, including carboxamide formation by reaction of an ester of the active molecule with a polymer amine, carbamate formation between an amine of the active molecule and a polymer chloroformate, or carbamate formation between an isocyanate of the active molecule and a polymer alcohol. The overall yields from these methods are typically less than desirable, often involving multiple steps and purification means. It is therefore necessary to design a process which isolates a conjugate of a VLA-4 inhibitor in quantitative or near quantitative yields.

The importance of such polymer conjugates indicates that there is a need for convenient and efficient syntheses of such materials.

SUMMARY OF THE INVENTION

This invention provides an improved synthesis of polymer conjugates of agricultural, therapeutic, and food additive compounds. The process of this invention produces the final conjugate products in good, often excellent, yields. In a preferred aspect, the invention provides a process for the preparation of conjugates by treating primary or secondary alcohol substituents of active compounds with polymeric nucleophiles using "Mitsunobu" or related reaction conditions.

In one aspect, the invention provides a process for the preparation of conjugates of active compounds, comprising the steps of:
(a) treating a primary or secondary alcohol substituent of at least one active compound under "Mitsunobu" or related conditions; and
(b) treating the product of (a) with a polymer containing nucleophilic substituents active under "Mitsunobu" or related conditions.

DETAILED DESCRIPTION OF THE INVENTION

In another aspect, the invention provides a process for the preparation of conjugates of active compounds, comprising the steps of:
(a) treating a primary or secondary alcohol substituent of at least one active compound with a trivalentphosphine, an azodicarbonyl compound, and an optional tertiary amine additive, in at least one solvent; and
(b) treating the product of (a) with a polymer containing nucleophilic substituents active under "Mitsunobu" conditions.

In another aspect, the invention provides a process for the preparation of conjugates of VLA-4 antagonists, comprising the steps of:
(a) treating a primary or secondary alcohol substituent of at least one VLA-4 antagonist with a trivalentphosphine, an azodicarbonyl compound, and an optional tertiary amine additive, in at least one solvent; and
(b) treating the product of (a) with a polymer containing nucleophilic substituents active under "Mitsunobu" conditions.

In a preferred aspect, the invention provides a process for the preparation of conjugates of VLA-4 antagonists, comprising the steps of:
(a) treating a primary alcohol substituent of at least one VLA-4 antagonist with a trivalentphosphine, an azodicarbonyl compound, and an optional tertiary amine additive, in at least one solvent; and
(b) treating the product of (a) with a polymer containing nucleophilic substituents active under "Mitsunobu" conditions.

In a preferred aspect, the invention provides a process for the preparation of conjugates of VLA-4 antagonists, comprising the steps of:
(a) treating a primary alcohol substituent of at least one VLA-4 antagonist with a trivalentphosphine, an azodicarbonyl compound, and an optional tertiary amine additive, in at least one solvent; and
(b) treating the product of (a) with a polymer containing nucleophilic substituents with a pKa of less than 13.

In a preferred aspect, the invention provides a process for the preparation of conjugates of VLA-4 antagonists, comprising the steps of:
(a) treating a primary alcohol substituent of at least one VLA-4 antagonist with a trivalentphosphine, an azodicarbonyl compound, and an optional tertiary amine additive, in at least one solvent; and
(b) treating the product of (a) with a polymer containing nucleophilic substituents with a pKa of less than 11.

In another aspect, the invention provides a process for the preparation of conjugates of formula (I),

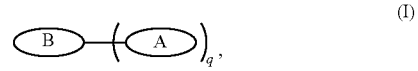

wherein q is from 1 to 100;

A, at each occurrence, is independently an active compound of formula (II),

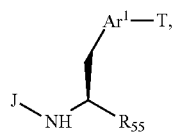

(II)

or a pharmaceutically acceptable salt thereof, wherein
$Ar^1$ is aryl or heteroaryl, wherein
the aryl or heteroaryl is optionally substituted with one or more groups which are each independently —$NO_2$, —CN, -halo, —$(Z^1)_aM_b((Z^2)_cR^Z)$ or -$D_dE_eF$—, wherein,
M is —C(O)—, —C(S)—, —S(O)—, or —$S(O)_2$—, provided when M is —S(O) or —$S(O)_2$, either a or c is zero;
$Z^1$ is —O—, —S—, or —$N(R^N)$—, wherein
$R^N$ is —H, —$(C_1-C_6)$alkyl, —$(C_1-C_6)$alkenyl, —$(C_1-C_6)$alkynyl, —$(C_1-C_6)$haloalkyl, —$(C_1-C_6)$alkanoyl, —$(C_3-C_8)$cycloalkyl, -heterocycle, -aryl, -heteroaryl, —$(C_3-C_8)$cycloalkanoyl, -heterocycloyl, -aroyl, -heteroaroyl, —$(C_1-C_6)$alkoxycarbonyl, or -aryl$(C_1-C_6)$alkoxycarbonyl, wherein
the aryl or heteroaryl is optionally substituted with one or more groups which are independently -halo, —$NO_2$, —CN, —$(C_1-C_6)$alkyl, —$(C_1-C_6)$haloalkyl, —$(C_1-C_6)$alkanoyl, or -aroyl;
$Z^2$ is —O—, —S—, or —$N(R^N)$—;
a, b and c are independently 0 or 1, provided when b is zero, a is zero, and when b is one, a is 0 or 1;
$R^Z$ is —H, —$(C_1-C_6)$alkyl, —$(C_1-C_6)$alkenyl, —$(C_1-C_6)$alkynyl, —$(C_1-C_6)$haloalkyl, —$(C_3-C_8)$cycloalkyl, —$(C_1-C_6)$alkylaryl, -heterocycle, -aryl, or -heteroaryl;
D is —$CH_2$—, —$OCH_2$—, —$CH_2O$—, —C(O)—, —$C(O)_2$—, —$C(O)(NR^N)$—, —$S(O)_2$—, —C(S)—, or —$C(S)_2$—;
E is —$CH(R_e)$—, —$CH(R_e)CH_2$—, —$(C_3-C_{16})$alkyl-, —$(C_1-C_6)$alkoxy-, —$(C_1-C_6)$alkenyl-, —$(C_1-C_6)$alkynyl-, —$(C_1-C_6)$haloalkyl-, —$(C_3-C_8)$ cycloalkyl-, -heterocycle-, -aryl-, or -heteroaryl-, wherein
$R_e$ is —H or —$N(R")(R^N)$; and
R" is —H or together with $R_f$ form a heterocycloalkyl;
F is a bond, —$CH(R_f)$—, or —$CH_2CH(R_f)$—, provided that F is covalently bonded to B, wherein
$R_f$ is —H, —$(C_1-C_6)$alkyl, —$(C_1-C_6)$haloalkyl, -aryl, —$(C_1-C_6)$alkylaryl, —$(C_3-C_8)$cycloalkyl, -heterocycloalkyl, heteroaryl, or together with R" form a heterocycloalkyl, wherein
each aryl or heteroaryl is optionally substituted with one or more groups which are each independently —$NO_2$, —CN, -halo, or —$(Z^1)_aM_b((Z^2)_cR^Z)$;
d is 0 or 1; and
e is 0 or 1, provided when E is —$(C_1-C_6)$alkoxy-, e is 1 to 250;
J is:
a) a group of formula (a),

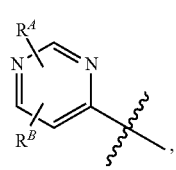

(a)

wherein
$R^A$ is —$(Z^1)_aM_b((Z^2)_cR^Z)$; and
$R^B$ is —H, —$NO_2$, —$(C_1-C_6)$alkyl, —$(C_3-C_8)$cycloalkyl, -aryl, -heteroaryl, —$(C_1-C_6)$haloalkyl, or $(N(R^{A1}))M_b((Z^2)_cR^Z)$, provided that when b is zero, c is also zero, wherein
each aryl or heteroaryl is optionally substituted with one or more groups which are each independently —CN, —$NO_2$, -halo, or —$(Z^1)_aM_b((Z^2)_cR^Z)$;
or
b) a group of formula (b),

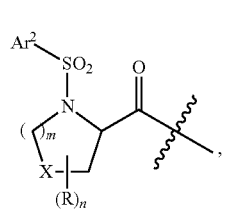

(b)

wherein
$Ar^2$ is $Ar^1$;
m is 0, 1, or 2;
n is 0, 1, or 2;
each R is independently —$(Z^1)_aM_b((Z^2)_cR^Z)$ or -$D_dE_eF$—; and
X is —$N(R^N)$—, —O—, —S—, —S(O)—, —$S(O)_2$—, or —$C(R)_2$—;
T is:
a) a group of formula (c),

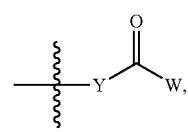

(c)

wherein
Y is —O— or —$N(R^N)$—; and
W is -$L_1$-$L_2$-, wherein
$L_1$ is $NR^2R^3$, wherein
$R^2$ and $R^3$ are independently —H or —$(C_1-C_6)$alkyl, or together with the nitrogen atom bound thereto, form a heterocycle containing 0 to 4 additional heteroatoms independently selected from —O—, —S—, and —$N(R^N)$; and
$L_2$ is absent, $R^N$, or -$D_dE_eF$—;
or
b) a group of formula (d)

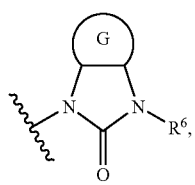

(d)

wherein
G is aryl or a monocyclic heteroaryl containing 1 to 3 nitrogens; and
$R^6$ is $R^N$ or $-D_dE_eF—$; and
$R^{55}$ is $-M(Z^2R^Z)$;
and
B is a group of formula (Ia)

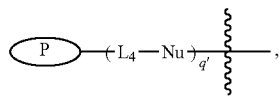
(Ia)

wherein
P is a polymer;
q' is greater than or equal to q, as defined in formula (I);
$L_4$ is $-D_dE_eF'_{f'}—$, wherein
F' is F or $—C(O)—$; and
f' is 0 or 1; and
Nu is $—N(SO_2R^4)—$, $—[S(O)_2]N(R^N)—$, -aryl-O—, -aryl-S—, $—N(C(O)CF_3)—$, $—(NC)C(H)C(O)—$, $—(NC)C(H)S(O)_2—$, $—[R^4S(O)_2]C(H)[S(O)_2]—$, $—[R^4S(O)_2]C(H)C(O)—$, or $—C(O)O—$, wherein
the aryl is optionally substituted with one or more groups that are each independently $—NO_2$, $—CN$, $—S(O)_2R^5$, $—C(O)OR^5$, or $—C(O)R^5$, wherein
$R^5$ is each independently $—H$, $—(C_1-C_6)$alkyl, $—(C_1-C_6)$alkenyl, $—(C_1-C_6)$alkynyl, $—(C_1-C_6)$haloalkyl, $—(C_3-C_8)$cycloalkyl, heterocycle, -aryl, -heteroaryl, wherein the aryl or heteroaryl is optionally substituted with $—(Z^1)_aM_b((Z^2)_cR^Z)$; and
$R^4$ is $—(C_1-C_6)$alkyl, $—(C_1-C_6)$alkenyl, $—(C_1-C_6)$alkynyl, $—(C_1-C_6)$haloalkyl, $—(C_3-C_8)$cycloalkyl, -heterocycle, -heteroaryl, or -aryl, wherein
the aryl or heteroaryl is optionally substituted with 1 to 4 groups which are independently $—NO_2$, $—CN$, -halo, or $—(Z^1)_aM_b((Z^2)_cR^Z$;
provided that when X is $—O—$ or $—N(R^N)—$, then m is two; and
provided that when R is covalently bonded to B, n is one and X is not $—O—$, $—S—$, $—S(O)—$, or $—S(O)_2—$;
where the process comprises the steps of:
a) treating, in at least one solvent, at least one active compound of formula (Ib),

(Ib)

wherein
A is as defined in formula (I); and
—OH is covalently bonded to F;
with a trivalentphosphine, an azodicarbonyl compound, and an optional tertiary amine additive; and
b) adding a polymeric nucleophile of formula (Ic),

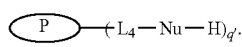
(Ic)

In another embodiment, the invention provides a process for preparing the conjugate of formula (I), wherein
Nu is $—N(SO_2R^4)—$, -phenyl-O—, $—N(C(O)CF_3)—$, $—(NC)C(H)C(O)—$, or $—C(O)O—$, wherein
$R^4$ is $—(C_1-C_6)$alkyl, $—(C_1-C_6)$haloalkyl, or -aryl, wherein
the aryl is optionally substituted with 1 to 4 groups which are independently $—NO_2$, $—CN$, -halo, or $—(Z^1)_aM_b((Z^2)_cR^Z)$;
and A, D, E, F, F', G, J, $L^1$, $L^2$, $L^4$, M, P, R, $R^4$, $R^B$, $R^N$, $R^Z$, $R_e$, $R_f$, $R^2$, $R^3$, $R^6$, $R^{55}$, R', T, W, X, Y, $Z^1$, $Z^2$, a, b, c, d, e, f', m, n, q, q', $Ar^1$, and $Ar^2$ are as defined in formula (I).

In embodiments of the invention, the Nu-H group of formula (Ic) has nucleophilic character.

In another embodiment, the invention provides a process for preparing the conjugate of formula (I), wherein
Nu is $—N(SO_2R^4)—$, -phenyl-O—, $—N(C(O)CF_3)—$, $—(NC)C(H)C(O)—$, or $—C(O)O—$, wherein
$R^4$ is $—(C_1-C_6)$alkyl, $—(C_1-C_6)$haloalkyl, or -aryl, wherein
the aryl is optionally substituted with 1 to 4 groups which are independently $—NO_2$, $—CN$, -halo, or $—(Z^1)_aM_b((Z^2)_cR^Z)$;
$L_4$ is $-D'_{d'}E'_{e'}F''_{f''}—$, wherein
D' is $—CH_2—$ or $—C(O)—$;
E' is $—CH(R_{e'})—$, $—(C_3-C_{16})$alkyl-, or -aryl-, wherein
$R_{e'}$ is $—H$ or $—NH(R^N)$;
F" is a bond or $—CH(R_{f'})—$ provided that F" is covalently bonded to B, wherein
$R_{f'}$ is $—H$, $—(C_1-C_6)$alkyl, $—(C_1-C_6)$haloalkyl, -aryl, or -heteroaryl,
wherein each aryl or heteroaryl is optionally substituted with one or more groups which are each independently $—NO_2$, $—CN$, -halo, or $—(Z^1)_aM_b((Z^2)_cR^Z)$;
d' is 0 or 1;
e' is 0 or 1; and
f" is 0 or 1;
and A, D, E, F, G, J, $L^1$, $L^2$, M, P, R, $R^4$, $R^B$, $R^N$, $R^Z$, $R_e$, $R_f$, $R^2R^3$, $R^6$, $R^{55}$, R", T, W, X, Y, $Z^1$, $Z^2$, a, b, c, d, e, m, n, q, q', $Ar^1$, and $Ar^2$ are as defined in formula (I).

In another embodiment, the invention provides a process for preparing the conjugate of formula (I), wherein
A at each occurrence is independently a compound of formula (III), (IV), (V), or (VI),

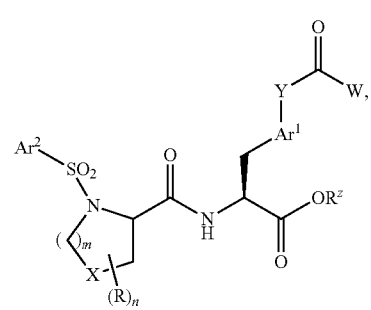
(III)

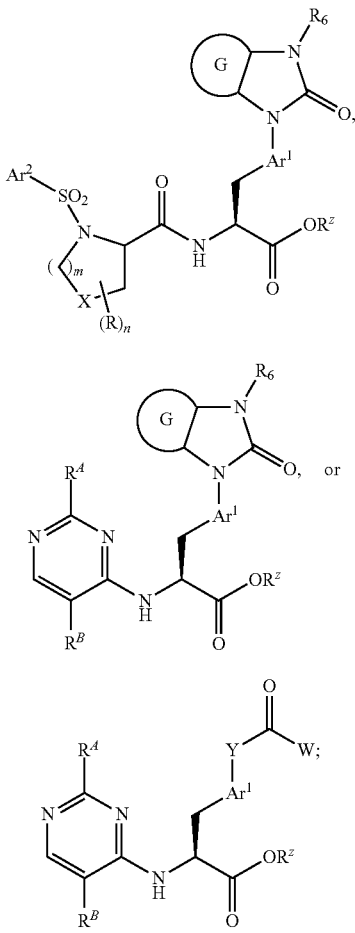

Nu is —N(SO₂R⁴)—, -phenyl-O—, —N(C(O)CF₃)—, —(NC)C(H)C(O)—, or —C(O)O—, wherein
R⁴ is —(C₁-C₆)alkyl, —(C₁-C₆)haloalkyl, or -aryl, wherein
the aryl is optionally substituted with 1 to 4 groups which are independently —NO₂, —CN, -halo, or —(Z¹)ₐMᵦ((Z²)𝒸R^Z);
L₄ is -D'_d E'_e F"_f'—, wherein
D' is —CH₂— or —C(O)—;
E' is —CH(R_e')—, —(C₃-C₁₆)alkyl-, or -aryl-, wherein
R_e' is —H or —NH(R^N);
F" is a bond or —CH(R_f')—, provided that F" is covalently bonded to B, wherein
R_f' is —H, —(C₁-C₆)alkyl, —(C₁-C₆)haloalkyl, -aryl, or -heteroaryl,
wherein each aryl or heteroaryl is optionally substituted with one or more groups which are each independently —NO₂, —CN, -halo, or —(Z¹)ₐMᵦ((Z²)𝒸R^Z);
d' is 0 or 1;
e' is 0 or 1; and
f" is 0 or 1;
and D, E, F, G, L¹, L², M, P, R, R⁴, R^B, R^N, R^Z, R_e, R_f, R², R³, R⁶, R", W, X, Y, Z¹, Z², a, b, c, d, e, m, n, q, q', Ar¹, and Ar² are as defined in formula (I). In preferred aspects, only W or R⁶ is covalently bonded to B, and each contains only one bond to B.

In another embodiment, the invention provides a process for preparing the conjugate of formula (I), wherein
A at each occurrence is independently a compound of formula (III), (IV), (V), or (VI);
Ar¹ is phenyl;
Nu is —N(SO₂R⁴)—, -phenyl-O—, —N(C(O)CF₃)—, —(NC)C(H)C(O)—, or —C(O)O—, wherein
R⁴ is —(C₁-C₆)alkyl, —(C₁-C₆)haloalkyl, or -aryl, wherein
the aryl is optionally substituted with 1 to 4 groups which are independently —NO₂, —CN, -halo, or —(Z¹)ₐMᵦ((Z²)𝒸R^Z);
L₄ is -D'_d E'_e F"_f'—, wherein
D' is —CH₂— or —C(O)—;
E' is —CH(R_e')—, —(C₃-C₁₆)alkyl-, or -aryl-, wherein
R_e' is —H or —NH(R^N);
F" is a bond or —CH(R_f')— provided that F" is covalently bonded to B, wherein
R_f' is —H, —(C₁-C₆)alkyl, —(C₁-C₆)haloalkyl, -aryl, or -heteroaryl,
wherein each aryl or heteroaryl is optionally substituted with one or more groups which are each independently —NO₂, —CN, -halo, or —(Z¹)ₐMᵦ((Z²)𝒸R^Z);
d' is 0 or 1;
e' is 0 or 1; and
f" is 0 or 1;
and D, E, F, G, L¹, L², M, P, R, R⁴, R^B, R^N, R^Z, R_e, R_f, R², R³, R⁶, R', W, X, Y, Z¹, Z², a, b, c, d, e, m, n, q, q', and Ar² are as defined in formula (I). In preferred aspects, only W or R⁶ is covalently bonded to B, and each contains only one bond to B.

In another embodiment, the invention provides a process for preparing the conjugate of formula (I), wherein
A at each occurrence is independently a compound of formula (III), (IV), (V), or (VI);
X is —S— or —CH₂—;
m is 1;
Ar¹ is phenyl;
Nu is —N(SO₂R⁴)—, -phenyl-O—, —N(C(O)CF₃)—, —(NC)C(H)C(O)—, or —C(O)O—, wherein
R⁴ is —(C₁-C₆)alkyl, —(C₁-C₆)haloalkyl, or -aryl, wherein
the aryl is optionally substituted with 1 to 4 groups which are independently —NO₂, —CN, -halo, or —(Z¹)ₐMᵦ((Z²)𝒸R^Z);
L₄ is -D'_d E'_e F"_f'—, wherein
D' is —CH₂— or —C(O)—;
E' is —CH(R_e')—, —(C₃-C₁₆)alkyl-, or -aryl-, wherein
R_e' is —H or —NH(R^N);
F" is a bond or —CH(R_f')— provided that F" is covalently bonded to B, wherein
R_f' is —H, —(C₁-C₆)alkyl, —(C₁-C₆)haloalkyl, -aryl, or -heteroaryl,
wherein each aryl or heteroaryl is optionally substituted with one or more groups which are each independently —NO₂, —CN, -halo, or —(Z¹)ₐMᵦ((Z²)𝒸R^Z);
d' is 0 or 1;
e' is 0 or 1; and
f" is 0 or 1;
and D, E, F, G, L¹, L², M, P, R, R⁴, R^B, R^N, R^Z, R_e, R_f, R², R³, R⁶, R", W, Y, Z¹, Z², a, b, c, d, e, n, q, q', and Ar² are as defined in formula (I). In preferred aspects, only W or R⁶ is covalently bonded to B, and each contains only one bond to B.

In another embodiment, the invention provides a process for preparing the conjugate of formula (I), wherein A at each occurrence is a compound of formula (VII),

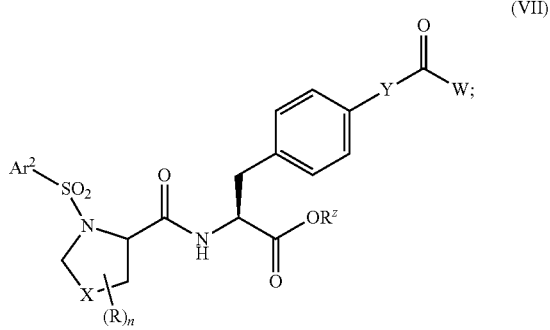

(VII)

X is —S— or —CH$_2$—;

Y is —O—;

W is -L$_1$-L$_2$-, wherein

L$_1$ is NR$^2$R$^3$, wherein

R$^2$ and R$^3$ together with the nitrogen atom bound thereto, form a heterocycle containing 0 to 4 additional heteroatoms independently selected from —O—, —S—, and —N(R$^N$); and L$_2$ is -D$_d$E$_e$F—;

Nu is —N(SO$_2$R$^4$)—, -phenyl-O—, —N(C(O)CF$_3$)—, —(NC)C(H)C(O)—, or —C(O)O—, wherein R$^4$ is —(C$_1$-C$_6$)alkyl, —(C$_1$-C$_6$)haloalkyl, or -aryl, wherein the aryl is optionally substituted with 1 to 4 groups which are independently —NO$_2$, —CN, -halo, or —(Z$^1$)$_a$M$_b$((Z$^2$)$_c$R$^Z$);

L$_4$ is -D'$_{d'}$E'$_{e'}$F''$_{f''}$—, wherein

D' is —CH$_2$— or —C(O)—;

E' is —CH(R$_{e'}$)—, —(C$_3$-C$_{16}$) alkyl-, or -aryl-, wherein

R$_{e'}$ is —H or —NH(R$^N$);

F'' is a bond or —CH(R$_{f'}$)— provided that F'' is covalently bonded to B, wherein R$_{f'}$ is —H, —(C$_1$-C$_6$)alkyl, —(C$_1$-C$_6$)haloalkyl, -aryl, or -heteroaryl, wherein each aryl or heteroaryl is optionally substituted with one or more groups which are each independently —NO$_2$, —CN, -halo, or —(Z$^1$)$_a$M$_b$((Z$^2$)$_c$R$^Z$)

d' is 0 or 1;

e' is 0 or 1; and f'' is 0 or 1;

and D, E, F, M, P, R, R$^N$, R$^Z$, R$_e$, R$_f$, R'', Z$^1$, Z$^2$, a, b, c, d, e, n, q, q', and Ar$^2$ are as defined in formula (I). In preferred aspects, only W is covalently bonded to B, and each W contains only one bond to B.

In another embodiment, the invention provides a process for preparing the conjugate of formula (I), wherein A at each occurrence is a compound of formula (VIII),

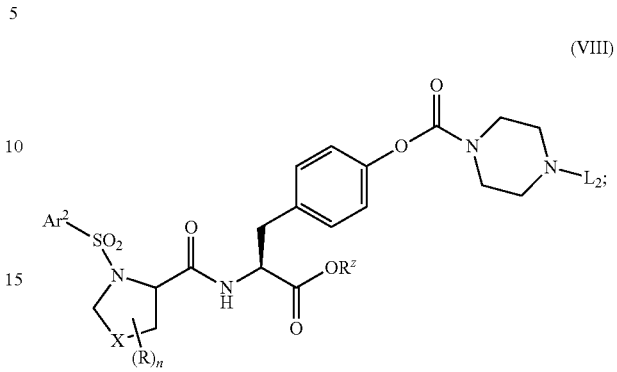

(VIII)

X is —S— or —CH$_2$—;

L$_2$ is -D$_d$E$_e$F—, wherein

D is —CH$_2$— or —C(O)—;

E is —CH(R$_e$)—, —(C$_3$-C$_{16}$)alkyl-, —(C$_1$-oxy-, —(C$_1$-C$_6$)haloalkyl-, —(C$_3$-C$_8$)cycloalkyl-, or -aryl-, wherein R$_e$ is —H or —NH(R$^N$);

F is a bond, —CH(R$_f$)—, or —CH$_2$CH(R$_f$)—, provided that F is covalently bonded to B, wherein R$_f$ is —H, —(C$_1$-C$_6$)alkyl, —(C$_1$-C$_6$)haloalkyl, -aryl, —(C$_1$-C$_6$)alkylaryl, —(C$_3$-C$_8$) cycloalkyl, -heterocycloalkyl, or -heteroaryl;

d is 0 or 1; and e is 0 or 1;

Nu is —N(SO$_2$R$^4$)—, -phenyl-O—, —N(C(O)CF$_3$)—, —(NC)C(H)C(O)—, or —C(O)O—, wherein R$^4$ is —(C$_1$-C$_6$)alkyl, —(C$_1$-C$_6$)haloalkyl, or -aryl, wherein the aryl is optionally substituted with 1 to 4 groups which are independently —NO$_2$, —CN, -halo, or —(Z$^1$)$_a$M$_b$((Z$^2$)$_c$R$^Z$);

L$_4$ is -D'$_{d'}$E'$_{e'}$F''$_{f''}$—, wherein

D' is —CH$_2$— or —C(O)—;

E' is —CH(R$_{e'}$)—, —(C$_3$-C$_{16}$)alkyl-, or -aryl-, wherein

R$_{e'}$ is —H or —NH(R$^N$);

F'' is a bond or —CH(R$_{f'}$)— provided that F'' is covalently bonded to B, wherein R$_{f'}$ is —H, —(C$_1$-C$_6$)alkyl, —(C$_1$-C$_6$)haloalkyl, -aryl, or -heteroaryl, wherein each aryl or heteroaryl is optionally substituted with one or more groups which are each independently —NO$_2$, —CN, -halo, or —(Z$^1$)$_a$M$_b$((Z$^2$)$_c$R$^Z$);

d' is 0 or 1;

e' is 0 or 1; and f'' is 0 or 1;

and M, P, R, R$^N$, R$^Z$, Z$^1$, Z$^2$, a, b, c, n, q, q', and Ar$^2$ are as defined in formula (I). In preferred aspects, only L$_2$ is covalently bonded to B, and each L$_2$ contains only one bond to B.

In another embodiment, the invention provides a process for preparing the conjugate of formula (I), wherein
A at each occurrence is a compound of formula (IX),

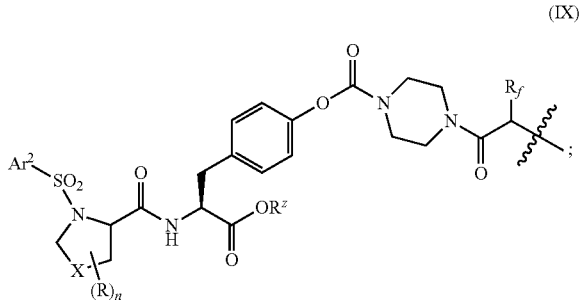

(IX)

X is —S— or —CH$_2$—;
R$_f$ is —H, (C$_1$-C$_6$)alkyl, —(C$_1$-C$_6$)haloalkyl, -aryl, —(C$_1$-C$_6$)alkylaryl, —(C$_3$-C$_8$)cycloalkyl, -heterocycloalkyl, or -heteroaryl;
Nu is —N(SO$_2$R$^4$)—, -phenyl-O—, —N(C(O)CF$_3$)—, —(NC)C(H)C(O)—, or —C(O)O—, wherein
  R$^4$ is —(C$_1$-C$_6$)alkyl, —(C$_1$-C$_6$)haloalkyl, or -aryl,
    wherein the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_d$E'$_e$F"$_{f''}$—, wherein
  D' is —CH$_2$— or —C(O)—;
  E' is —CH(R$_{e'}$)—, —(C$_3$-C$_{16}$)alkyl-, or -aryl-, wherein
    R$_{e'}$ is —H or —NH(R$^N$);
  F" is a bond or —CH(R$_{f'}$)— provided that F" is covalently bonded to B, wherein
    R$_{f'}$ is —H, —(C$_1$-C$_6$)alkyl, —(C$_1$-C$_6$)haloalkyl, -aryl, or -heteroaryl,
      wherein each aryl or heteroaryl is optionally substituted with one or more groups which are each independently —NO$_2$, —CN, -halo, or —(Z$^1$)$_a$M$_b$((Z$^2$)$_c$R$^Z$);
  d' is 0 or 1;
  e' is 0 or 1; and
  f" is 0 or 1;
and M, P, R, R$^N$, R$^Z$, Z$^1$, Z$^2$, a, b, c, n, q, q', and Ar$^2$ are as defined in formula (I).

In another embodiment, the invention provides a process for preparing the conjugate of formula (I), wherein
A at each occurrence is a compound of formula (IX);
R$^Z$ is —H or —(C$_1$-C$_6$)alkyl;
X is —S— or —CH$_2$—;
R$_f$ is —H, —(C$_1$-C$_6$)alkyl, —(C$_1$-C$_6$)haloalkyl, -aryl, —(C$_1$-C$_6$)alkylaryl, —(C$_3$-C$_8$)cycloalkyl, -heterocycloalkyl, or -heteroaryl;
Nu is —N(SO$_2$R$^4$)—, -phenyl-O—, —N(C(O)CF$_3$)—, —(NC)C(H)C(O)—, or —C(O)O—, wherein
  R$^4$ is —(C$_1$-C$_6$)alkyl, —(C$_1$-C$_6$)haloalkyl, or -aryl,
    wherein the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_d$E'$_e$F"$_{f''}$—, wherein
  D' is —CH$_2$— or —C(O)—;
  E' is —CH(R$_{e'}$)—, —(C$_3$-C$_{16}$)alkyl-, or -aryl-, wherein
    R$_{e'}$ is —H or —NH(R$^N$);
  F" is a bond or —CH(R$_{f'}$)— provided that F" is covalently bonded to B, wherein
    R$_{f'}$ is —H, —(C$_1$-C$_6$)alkyl, —(C$_1$-C$_6$)haloalkyl, -aryl, or -heteroaryl,
      wherein each aryl or heteroaryl is optionally substituted with one or more groups which are each independently —NO$_2$, —CN, -halo, or —(Z$^1$)$_a$M$_b$((Z$^2$)$_c$R$^Z$);
  d' is 0 or 1;
  e' is 0 or 1; and
  f" is 0 or 1;
and M, P, R, R$^N$, Z$^1$, Z$^2$, a, b, c, n, q, q', and Ar$^2$ are as defined in formula (I).

In another embodiment, the invention provides a process for preparing the conjugate of formula (I), wherein
A at each occurrence is a compound of formula (IX),
R$^Z$ is —H;
X is —S— or —CH$_2$—;
R$_f$ is —H, —(C$_1$-C$_6$)alkyl, —(C$_1$-C$_6$)haloalkyl, -aryl, —(C$_1$-C$_6$)alkylaryl, —(C$_3$-C$_8$)cycloalkyl, -heterocycloalkyl, or -heteroaryl;
Nu is —N(SO$_2$R$^4$)—, -phenyl-O—, —N(C(O)CF$_3$)—, —(NC)C(H)C(O)—, or —C(O)O—, wherein
  R$^4$ is —(C$_1$-C$_6$)alkyl, —(C$_1$-C$_6$)haloalkyl, or -aryl,
    wherein the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_d$E'$_e$F"$_{f''}$—, wherein
  D' is —CH$_2$— or —C(O)—;
  E' is —CH(R$_{e'}$)—, —(C$_3$-C$_{16}$)alkyl-, or -aryl-, wherein
    R$_{e'}$ is —H or —NH(R$^N$);
  F" is a bond or —CH(R$_{f'}$)— provided that F" is covalently bonded to B, wherein
    R$_{f'}$ is —H, —(C$_1$-C$_6$)alkyl, —(C$_1$-C$_6$)haloalkyl, -aryl, or -heteroaryl,
      wherein each aryl or heteroaryl is optionally substituted with one or more groups which are each independently —NO$_2$, —CN, -halo, or —(Z$^1$)$_a$M$_b$((Z$^2$)$_c$R$^Z$);
  d' is 0 or 1;
  e' is 0 or 1; and
  f" is 0 or 1;
and M, P, R, R$^N$, Z$^1$, Z$^2$, a, b, c, n, q, q', and Ar$^2$ are as defined in formula (I).

In another embodiment, the invention provides a process for preparing the conjugate of formula (I), wherein
A at each occurrence is a compound of formula (IX);
R$^Z$ is —H;
X is —CH$_2$—;
m is 1;
n is 0;
R$_f$ is —H, —(C$_1$-C$_6$)alkyl, —(C$_1$-C$_6$)haloalkyl, -aryl, —(C$_1$-C$_6$)alkylaryl, —(C$_3$-C$_8$)cycloalkyl, -heterocycloalkyl, or -heteroaryl;
Nu is —N(SO$_2$R$^4$)—, -phenyl-O—, —N(C(O)CF$_3$)—, —(NC)C(H)C(O)—, or —C(O)O—, wherein
  R$^4$ is —(C$_1$-C$_6$)alkyl, —(C$_1$-C$_6$)haloalkyl, or -aryl,
    wherein the aryl is optionally substituted with 1 to 4 groups which are independently —NO$_2$, —CN, -halo, or -(Z)$_a$M$_b$((Z$^2$)$_c$R$^Z$);
L$_4$ is -D'$_d$E'$_e$F"$_{f''}$—, wherein
  D' is —CH$_2$— or —C(O)—;
  E' is —CH(R$_{e'}$)—, —(C$_3$-C$_{16}$)alkyl-, or -aryl-, wherein
    R$_{e'}$ is —H or —NH(R$^N$);

F" is a bond or —CH($R_f$)— provided that F" is covalently bonded to B, wherein $R_f$ is —H, —($C_1$-$C_6$)alkyl, —($C_1$-$C_6$)haloalkyl, -aryl, or -heteroaryl, wherein each aryl or heteroaryl is optionally substituted with one or more groups which are each independently —$NO_2$, —CN, -halo, or —($Z^1$)$_a$$M_b$(($Z^2$)$_c$$R^Z$);

d' is 0 or 1;

e' is 0 or 1;

f" is 0 or 1;

and M, P, $R^N$, $Z^1$, $Z^2$, a, b, c, q, q', and $Ar^2$ are as defined in formula (I).

In another embodiment, the invention provides a process for preparing the conjugate of formula (I), wherein A at each occurrence is a compound of formula (X),

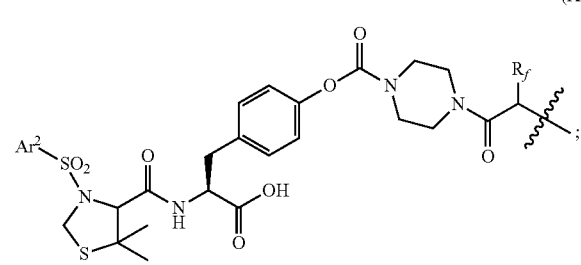

(X)

$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;

Nu is —N($SO_2R^4$)—, -phenyl-O—, —N(C(O)$CF_3$)—, —(NC)C(H)C(O)—, or —C(O)O—, wherein $R^4$ is —($C_1$-$C_6$)alkyl, —($C_1$-$C_6$)haloalkyl, or -aryl, wherein the aryl is optionally substituted with 1 to 4 groups which are independently —$NO_2$, —CN, -halo, or —($Z^1$)$_a$$M_b$(($Z^2$)$_c$$R^Z$);

$L_4$ is -D'$_d$·E'$_e$·F"$_{f''}$—, wherein

D' is —$CH_2$— or —C(O)—;

E' is —CH($R_{e'}$)—, —($C_3$-$C_{16}$)alkyl-, or -aryl-, wherein $R_{e'}$ is —H or —NH($R^N$);

F" is a bond or —CH($R_f$)— provided that F" is covalently bonded to B, wherein $R_f$ is —H, —($C_1$-$C_6$)alkyl, —($C_1$-$C_6$)haloalkyl, -aryl, or -heteroaryl, wherein each aryl or heteroaryl is optionally substituted with one or more groups which are each independently —$NO_2$, —CN, -halo, or —($Z^1$)$_a$$M_b$(($Z^2$)$_c$$R^Z$);

d' is 0 or 1;

e' is 0 or 1; and f" is 0 or 1;

and M, P, $R^N$, $Z^1$, $Z^2$, a, b, c, q, q', and $Ar^2$ are as defined in formula (I).

In another embodiment, the invention provides a process for preparing the conjugate of formula (I), wherein A at each occurrence is a compound of formula (XI),

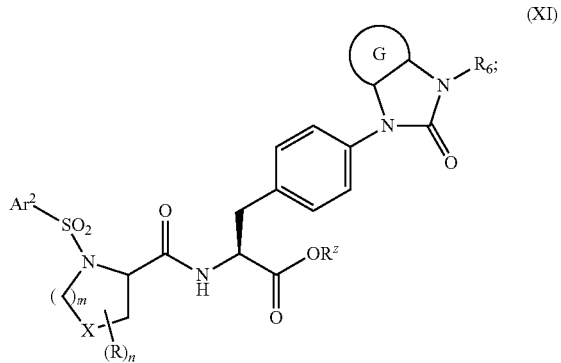

(XI)

X is —S— or —$CH_2$—;

m is 1;

Nu is —N($SO_2R^4$)—, -phenyl-O—, —N(C(O)$CF_3$)—, —(NC)C(H)C(O)—, or —C(O)O—, wherein $R^4$ is —($C_1$-$C_6$)alkyl, —($C_1$-$C_6$)haloalkyl, or -aryl, wherein the aryl is optionally substituted with 1 to 4 groups which are independently —$NO_2$, —CN, -halo, or —($Z^1$)$_a$$M_b$(($Z^2$)$_c$$R^Z$);

$L_4$ is -D'$_d$·E'$_e$·F"$_{f''}$—, wherein

D' is —$CH_2$— or —C(O)—;

E' is —CH($R_{e'}$)—, —($C_3$-$C_{16}$)alkyl-, or -aryl-, wherein $R_{e'}$ is —H or —NH($R^N$);

F" is a bond or —CH($R_f$)— provided that F" is covalently bonded to B, wherein $R_f$ is —H, —($C_1$-$C_6$)alkyl, —($C_1$-$C_6$)haloalkyl, -aryl, or -heteroaryl, wherein each aryl or heteroaryl is optionally substituted with one or more groups which are each independently —$NO_2$, —CN, -halo, or —($Z^1$)$_a$$M_b$(($Z^2$)$_c$$R^Z$);

d' is 0 or 1;

e' is 0 or 1; and f" is 0 or 1;

$R^6$ is -$D_d$$E_e$F—, wherein

D is —$CH_2$— or —C(O)—;

E is —CH($R_e$)—, —($C_3$-$C_{16}$)alkyl-, —($C_1$-$C_6$)alkoxy-, —($C_1$-$C_6$)haloalkyl-, —($C_3$-$C_8$)cycloalkyl-, or -aryl-, wherein $R_e$ is —H or —NH($R^N$);

F is a bond, —CH($R_f$)—, or —$CH_2$CH($R_f$)—, provided that F is covalently bonded to B, wherein $R_f$ is —H, —($C_1$-$C_6$)alkyl, —($C_1$-$C_6$)haloalkyl, -aryl, ($C_1$-$C_6$)alkylaryl, —($C_3$-$C_8$) cycloalkyl, heterocycloalkyl, or -heteroaryl;

d is 0 or 1; and e is 0 or 1;

and G, M, P, R, $R^N$, $R^Z$, $Z^1$, $Z^2$, a, b, c, n, q, q', and $Ar^2$ are as defined in formula (I). In preferred aspects, only -$D_d$$E_e$F— is covalently bonded to B, and each -$D_d$$E_e$F— contains only one bond to B.

In another embodiment, the invention provides a process for preparing the conjugate of formula (I), wherein
A at each occurrence is a compound of formula (XII),

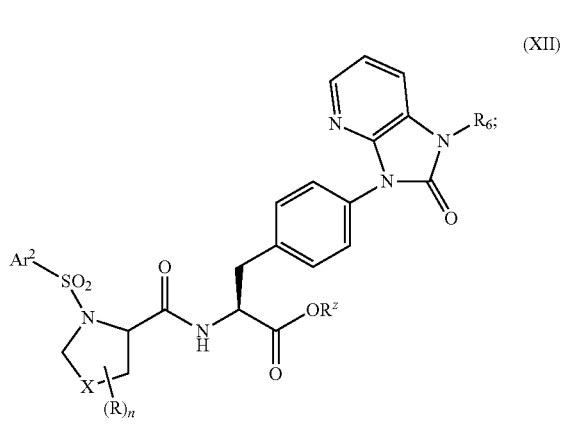

(XII)

X is —S— or —CH$_2$—;
Nu is —N(SO$_2$R$^4$)—, -phenyl-O—, —N(C(O)CF$_3$)—, —(NC)C(H)C(O)—, or —C(O)O—, wherein
    R$^4$ is —(C$_1$-C$_6$)alkyl, —(C$_1$-C$_6$)haloalkyl, or -aryl,
        wherein the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_{d'}$E'$_{e'}$F"$_{f''}$—, wherein
    D' is —CH$_2$— or —C(O)—;
    E' is —CH(R$_{e'}$)—, —(C$_3$-C$_{16}$)alkyl-, or -aryl-, wherein
        R$_{e'}$ is —H or —NH(R$^N$);
    F" is a bond or —CH(R$_{f'}$)— provided that F" is covalently bonded to B, wherein
        R$_{f'}$ is —H, —(C$_1$-C$_6$)alkyl, —(C$_1$-C$_6$)haloalkyl, -aryl, or -heteroaryl,
            wherein each aryl or heteroaryl is optionally substituted with one or more groups which are each independently —NO$_2$, —CN, -halo, or —(Z$^1$)$_a$M$_b$((Z$^2$)$_c$R$^Z$);
    d' is 0 or 1;
    e' is 0 or 1; and
    f" is 0 or 1;
R$^6$ is -D$_d$E$_e$F—, wherein
    D is —CH$_2$— or —C(O)—;
    E is —CH(R$_e$)—, —(C$_3$-C$_{16}$)alkyl-, —(C$_1$-C$_6$)alkoxy-, —(C$_1$-C$_6$)haloalkyl-, —(C$_3$-C$_8$)cycloalkyl-, or -aryl-, wherein
        R$_e$ is —H or —NH(R$^N$);
    F is a bond, —CH(R$_f$)—, or —CH$_2$CH(R$_f$)—, provided that F is covalently bonded to B, wherein
        R$_f$ is —H, —(C$_1$-C$_6$)alkyl, —(C$_1$-C$_6$)haloalkyl, -aryl, —(C$_1$-C$_6$)alkylaryl, —(C$_3$-C$_8$) cycloalkyl, heterocycloalkyl, or -heteroaryl;
    d is 0 or 1; and
    e is 0 or 1;
and M, P, R, R$^N$, R$^Z$, Z$^1$, Z$^2$, a, b, c, n, q, q', and Ar$^2$ are as defined in formula (I). In preferred aspects, only -D$_d$E$_e$F— is covalently bonded to B, and each -D$_d$E$_e$F— contains only one bond to B.

In another embodiment, the invention provides a process for preparing the conjugate of formula (I), wherein
A at each occurrence is a compound of formula (XIII),

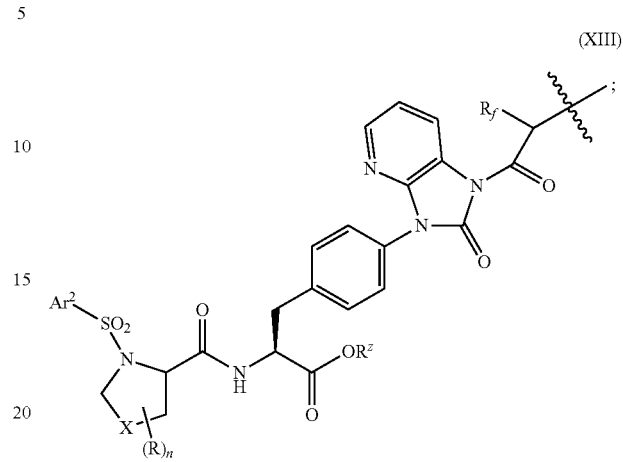

(XIII)

X is —S— or —CH$_2$—;
R$_f$ is —H, —(C$_1$-C$_6$)alkyl, —(C$_1$-C$_6$)haloalkyl, -aryl, —(C$_1$-C$_6$)alkylaryl, —(C$_3$-C$_8$) cycloalkyl, -heterocycloalkyl, or -heteroaryl;
Nu is —N(SO$_2$R$^4$)—, -phenyl-O—, —N(C(O)CF$_3$)—, —(NC)C(H)C(O)—, or —C(O)O—, wherein
    R$^4$ is —(C$_1$-C$_6$)alkyl, —(C$_1$-C$_6$)haloalkyl, or -aryl,
        wherein the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_{d'}$E'$_{e'}$F"$_{f''}$—, wherein
    D' is —CH$_2$— or —C(O)—;
    E' is —CH(R$_{e'}$)—, —(C$_3$-C$_{16}$)alkyl-, or -aryl-, wherein
        R$_{e'}$ is —H or —NH(R$^N$);
    F" is a bond or —CH(R$_{f'}$)— provided that F" is covalently bonded to B, wherein
        R$_{f'}$ is —H, —(C$_1$-C$_6$)alkyl, —(C$_1$-C$_6$)haloalkyl, -aryl, or -heteroaryl,
            wherein each aryl or heteroaryl is optionally substituted with one or more groups which are each independently —NO$_2$, —CN, -halo, or —(Z$^1$)$_a$M$_b$((Z$^2$)$_c$R$^Z$);
    d' is 0 or 1;
    e' is 0 or 1; and
    f" is 0 or 1;
and M, P, R, R$^N$, R$^Z$, Z$^1$, Z$^2$, a, b, c, n, q, q', and Ar$^2$ are as defined in formula (I).

In another embodiment, the invention provides a process for preparing the conjugate of formula (I), wherein
A at each occurrence is a compound of formula (XIII);
R$^Z$ is —H or —(C$_1$-C$_6$)alkyl;
X is —S— or —CH$_2$—;
R$_f$ is —H, —(C$_1$-C$_6$)alkyl, —(C$_1$-C$_6$)haloalkyl, -aryl, —(C$_1$-C$_6$)alkylaryl, —(C$_3$-C$_8$)cycloalkyl, -heterocycloalkyl, or -heteroaryl;
Nu is —N(SO$_2$R$^4$)—, -phenyl-O—, —N(C(O)CF$_3$)—, —(NC)C(H)C(O)—, or —C(O)O—, wherein
    R$^4$ is —(C$_1$-C$_6$)alkyl, —(C$_1$-C$_6$)haloalkyl, or -aryl, wherein
        the aryl is optionally substituted with 1 to 4 groups which are independently —NO$_2$, —CN, -halo, or —(Z$^1$)$_a$M$_b$((Z$^2$)$_c$R$^Z$);

$L_4$ is -$D'_d E'_e F''_{f'}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F'' is a bond or —CH($R_{f'}$)— provided that F'' is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —$(Z^1)_a M_b ((Z^2)_c R^Z)$;
    d' is 0 or 1;
    e' is 0 or 1; and
    f'' is 0 or 1;
and M, P, R, $R^N$, $Z^1$, $Z^2$, a, b, c, n, q, q', and $Ar^2$ are as defined in formula (I).

In another embodiment, the invention provides a process for preparing the conjugate of formula (I), wherein
A at each occurrence is a compound of formula (XIII),
$R^Z$ is —H;
X is —S— or —$CH_2$—;
$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;
Nu is —N($SO_2 R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl,
    wherein the aryl is optionally substituted with 1 to 4 groups which are independently —$NO_2$, —CN, -halo, or —$(Z^1)_a M_b ((Z^2)_c R^Z)$;
$L_4$ is -$D'_d E'_e F''_{f'}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F'' is a bond or —CH($R_{f'}$)— provided that F'' is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —$(Z^1)_a M_b ((Z^2)_c R^Z)$;
    d' is 0 or 1;
    e' is 0 or 1; and
    f'' is 0 or 1;
and M, P, R, $R^N$, $Z^1$, $Z^2$, a, b, c, n, q, q', and $Ar^2$ are as defined in formula (I).

In another embodiment, the invention provides a process for preparing the conjugate of formula (I), wherein
A at each occurrence is a compound of formula (XIII);
$R^Z$ is —H;
X is —$CH_2$—;
n is 0;
$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;
Nu is —N($SO_2 R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl,
    wherein the aryl is optionally substituted with 1 to 4 groups which are independently —$NO_2$, —CN, -halo, or —$(Z^1)_a M_b ((Z^2)_c R^Z)$;
$L_4$ is -$D'_d E'_e F''_{f'}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F'' is a bond or —CH($R_{f'}$)— provided that F'' is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —$(Z^1)_a M_b ((Z^2)_c R^Z)$;
    d' is 0 or 1;
    e' is 0 or 1; and
    f'' is 0 or 1;
and M, P, $R^N$, $Z^1$, $Z^2$, a, b, c, q, q', and $Ar^2$ are as defined in formula (I).

In another embodiment, the invention provides a process for preparing the conjugate of formula (I), wherein
A at each occurrence is a compound of formula (XIV), (XIV)

$R^Z$ is —H;
$R_f$ is —H, —($C_1$-$C_6$)alkyl, —($C_1$-$C_6$)haloalkyl, -aryl, —($C_1$-$C_6$)alkylaryl, —($C_3$-$C_8$) cycloalkyl, -heterocycloalkyl, or -heteroaryl;
Nu is —N($SO_2 R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl, wherein
    the aryl is optionally substituted with 1 to 4 groups which are independently —$NO_2$, —CN, -halo, or —$(Z^1)_a M_b ((Z^2)_c R^Z)$;
$L_4$ is -$D'_d E'_e F''_{f'}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F'' is a bond or —CH($R_{f'}$)— provided that F'' is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —$(Z^1)_a M_b ((Z^2)_c R^Z)$;
    d' is 0 or 1;
    e' is 0 or 1; and
    f'' is 0 or 1;
and M, P, $R^N$, $Z^1$, $Z^2$, a, b, c, q, q', and $Ar^2$ are as defined in formula (I).

In another embodiment, the invention provides a process for preparing the conjugate of formula (I), wherein A at each occurrence is a compound of formula (XV),

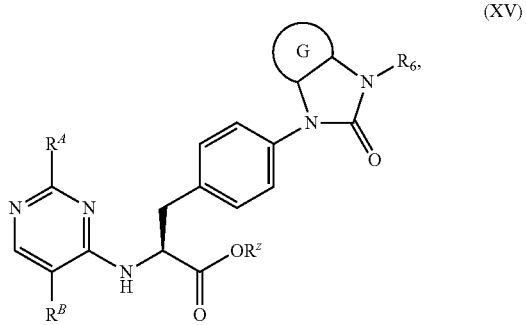

(XV)

wherein only $R^6$ is bonded to B and each $R^6$ contains only one bond to B;

Nu is —N(SO$_2$R$^4$)—, -phenyl-O—, —N(C(O)CF$_3$)—, —(NC)C(H)C(O)—, or —C(O)O—, wherein $R^4$ is —(C$_1$-C$_6$)alkyl, —(C$_1$-C$_6$)haloalkyl, or -aryl,
wherein the aryl is optionally substituted with 1 to 4 groups which are independently —NO$_2$, —CN, -halo, or —(Z$^1$)$_a$M$_b$((Z$^2$)$_c$R$^Z$);

L$_4$ is -D'$_{d'}$E'$_{e'}$F"$_{f''}$—, wherein

D' is —CH$_2$— or —C(O)—;

E' is —CH(R$_{e'}$)—, —(C$_3$-C$_{16}$)alkyl-, or -aryl-, wherein
R$_{e'}$ is —H or —NH(R$^N$);

F" is a bond or —CH(R$_{f'}$)— provided that F" is covalently bonded to B, wherein R$_{f'}$ is —H, —(C$_1$-C$_6$)alkyl, —(C$_1$-C$_6$)haloalkyl, -aryl, or -heteroaryl,
wherein each aryl or heteroaryl is optionally substituted with one or more groups which are each independently —NO$_2$, —CN, -halo, or —(Z$^1$)$_a$M$_b$((Z$^2$)$_c$R$^Z$);

d' is 0 or 1;

e' is 0 or 1; and f" is 0 or 1;

$R^6$ is -D$_d$E$_e$F—, wherein

D is —CH$_2$— or —C(O)—;

E is —CH(R$_e$)—, —(C$_3$-C$_{16}$)alkyl-, —(C$_1$-C$_6$)alkoxy-, —(C$_1$-C$_6$)haloalkyl-, —(C$_3$-C$_8$)cycloalkyl-, or -aryl-, wherein
R$_e$ is —H or —NH(R$^N$);

F is a bond, —CH(R$_f$)—, or —CH$_2$CH(R$_f$)—, provided that F is covalently bonded to B, wherein R$_f$ is —H, —(C$_1$-C$_6$)alkyl, —(C$_1$-C$_6$)haloalkyl, -aryl, (C$_1$-C$_6$)alkylaryl, —(C$_3$-C$_8$)cycloalkyl, heterocloalkyl, or -heteroaryl;

d is 0 or 1; and e is 0 or 1;

and G, M, P, $R^A$, $R^B$, $R^N$, $R^Z$, $Z^1$, $Z^2$, a, b, c, q, and q' are as defined in formula (I).

In another embodiment, the invention provides a process for preparing the conjugate of formula (I), wherein A at each occurrence is a compound of formula (XVI),

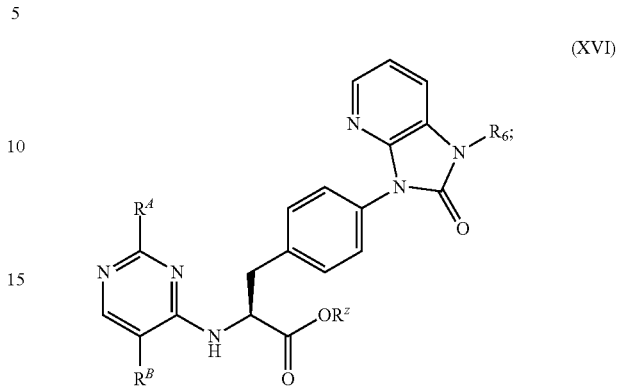

(XVI)

Nu is —N(SO$_2$R$^4$)—, -phenyl-O—, —N(C(O)CF$_3$)—, —(NC)C(H)C(O)—, or —C(O)O—, wherein $R^4$ is —(C$_1$-C$_6$)alkyl, —(C$_1$-C$_6$)haloalkyl, or -aryl, wherein
the aryl is optionally substituted with 1 to 4 groups which are independently —NO$_2$, —CN, -halo, or —(Z$^1$)$_a$M$_b$((Z$^2$)$_c$R$^Z$);

L$_4$ is -D'$_{d'}$E'$_{e'}$F"$_{f''}$—, wherein

D' is —CH$_2$— or —C(O)—;

E' is —CH(R$_{e'}$)—, —(C$_3$-C$_{16}$)alkyl-, or -aryl-, wherein
R$_{e'}$ is —H or —NH(R$^N$);

F" is a bond or —CH(R$_{f'}$)— provided that F" is covalently bonded to B, wherein R$_{f'}$ is —H, —(C$_1$-C$_6$)alkyl, —(C$_1$-C$_6$)haloalkyl, -aryl, or -heteroaryl,
wherein each aryl or heteroaryl is optionally substituted with one or more groups which are each independently —NO$_2$, —CN, -halo, or —(Z$^1$)$_a$M$_b$((Z$^2$)$_c$R$^Z$);

d' is 0 or 1;

e' is 0 or 1; and f" is 0 or 1;

$R^6$ is -D$_d$E$_e$F—, wherein

D is —CH$_2$— or —C(O)—;

E is —CH(R$_e$)—, —(C$_3$-C$_{16}$)alkyl-, —(C$_1$-C$_6$)alkoxy-, —(C$_1$-C$_6$)haloalkyl-, —(C$_3$-C$_8$)cycloalkyl-, or -aryl-, wherein
R$_e$ is —H or —NH(R$^N$);

F is a bond, —CH(R$_f$)—, or —CH$_2$CH(R$_f$)—, provided that F is covalently bonded to B, wherein R$_f$ is —H, —(C$_1$-C$_6$)alkyl, —(C$_1$-C$_6$)haloalkyl, -aryl, —(C$_1$-C$_6$)alkylaryl, —(C$_3$-C$_8$) cycloalkyl, heterocloalkyl, or -heteroaryl;

d is 0 or 1; and e is 0 or 1;

and M, P, $R^A$, $R^B$, $R^N$, $R^Z$, $Z^1$, $Z^2$, a, b, c, q, and q' are as defined in formula (I). In preferred aspects, only -D$_d$E$_e$F— is covalently bonded to B, and each -D$_d$E$_e$F— contains only one bond to B.

In another embodiment, the invention provides a process for preparing the conjugate of formula (I), wherein
A at each occurrence is a compound of formula (XVII),

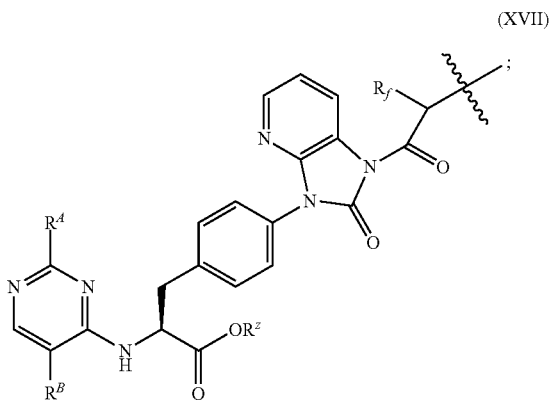

(XVII)

$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;

Nu is —N($SO_2R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl, wherein
    the aryl is optionally substituted with 1 to 4 groups which are independently —$NO_2$, —CN, -halo, or —($Z^1$)$_a$$M_b$(($Z^2$)$_c$$R^Z$);

$L_4$ is -D'$_d$E'$_e$F"$_{f'}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F" is a bond or —CH($R_{f'}$)— provided that F" is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —($Z^1$)$_a$$M_b$(($Z^2$)$_c$$R^Z$);
  d' is 0 or 1;
  e' is 0 or 1; and
  f" is 0 or 1;
and M, P, $R^A$, $R^B$, $R^N$, $R^Z$, $Z^1$, $Z^2$, a, b, c, q, and q' are as defined in formula (I).

In another embodiment, the invention provides a process for preparing the conjugate of formula (I), wherein
A at each occurrence is a compound of formula (XVII);
$R^Z$ is —H or —($C_1$-$C_6$)alkyl;
$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;

Nu is —N($SO_2R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl, wherein
    the aryl is optionally substituted with 1 to 4 groups which are independently —$NO_2$, —CN, -halo, or —($Z^1$)$_a$$M_b$(($Z^2$)$_c$$R^Z$);

$L_4$ is -D'$_d$E'$_e$F"$_{f'}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F" is a bond or —CH($R_{f'}$)— provided that F" is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —($Z^1$)$_a$$M_b$(($Z^2$)$_c$$R^Z$);
  d' is 0 or 1;
  e' is 0 or 1; and
  f" is 0 or 1;
and A, P, $R^A$, $R^B$, $R^N$, $Z^1$, $Z^2$, a, b, c, q, and q' are as defined in formula (I).

In another embodiment, the invention provides a process for preparing the conjugate of formula (I), wherein
A at each occurrence is a compound of formula (XVII);
$R^Z$ is —H;
$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;

Nu is —N($SO_2R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl, wherein
    the aryl is optionally substituted with 1 to 4 groups which are independently —$NO_2$, —CN, -halo, or —($Z^1$)$_a$$M_b$(($Z^2$)$_c$$R^Z$);

$L_4$ is -D'$_d$E'$_e$F"$_{f'}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F" is a bond or —CH($R_{f'}$)— provided that F" is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —($Z^1$)$_a$$M_b$(($Z^2$)$_c$$R^Z$);
  d' is 0 or 1;
  e' is 0 or 1; and
  f" is 0 or 1;
and M, P, $R^A$, $R^B$, $R^N$, $Z^1$, $Z^2$, a, b, c, q, and q' are as defined in formula (I).

In another embodiment, the invention provides a process for preparing the conjugate of formula (I), wherein
A at each occurrence is a compound of formula (XVIII),

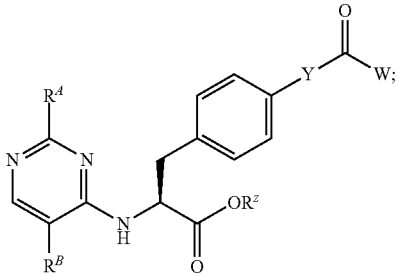

(XVIII)

Y is —O—;
W is -$L_1$-$L_2$-, wherein
  $L^2$, is $NR^3R^3$, wherein
    $R^2$ and $R^3$ together with the nitrogen atom bound thereto, form a heterocycle containing 0 to 4 additional heteroatoms independently selected from —O—, —S—, and —N($R^N$); and
  $L_2$ is -$D_d E_e F$—;

Nu is —N(SO$_2$R$^4$)—, -phenyl-O—, —N(C(O)CF$_3$)—, —(NC)C(H)C(O)—, or —C(O)O—, wherein
R$^4$ is —(C$_1$-C$_6$)alkyl, —(C$_1$-C$_6$)haloalkyl, or -aryl, wherein
the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_{d'}$E'$_{e'}$F"$_{f''}$—, wherein
D' is —CH$_2$— or —C(O)—;
E' is —CH(R$_{e'}$)—, —(C$_3$-C$_{16}$)alkyl-, or -aryl-, wherein
R$_{e'}$ is —H or —NH(R$^N$);
F" is a bond or —CH(R$_{f'}$)— provided that F" is covalently bonded to B, wherein
R$_{f'}$ is —H, —(C$_1$-C$_6$)alkyl, —(C$_1$-C$_6$)haloalkyl, -aryl, or -heteroaryl,
wherein each aryl or heteroaryl is optionally substituted with one or more groups which are each independently —NO$_2$, —CN, -halo, or —(Z$^1$)$_a$M$_b$((Z$^2$)$_c$R$^Z$);
d' is 0 or 1;
e' is 0 or 1; and
f" is 0 or 1;
and D, E, F, M, P, R$^A$, R$^B$, R$^N$, R$^Z$, R$_e$, R$_f$, R", Z$^1$, Z$^2$, a, b, c, d, e, q and q' are as defined in formula (I). In preferred aspects, only W is covalently bonded to B, and each W contains only one bond to B.

In another embodiment, the invention provides a process for preparing the conjugate of formula (I), wherein
A at each occurrence is a compound of formula (XIX),

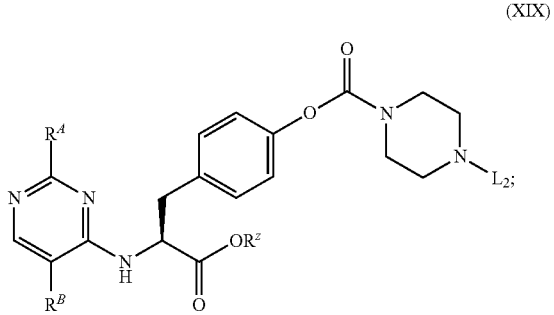

(XIX)

Y is —O—;
W is -L$_1$-L$_2$-, wherein
L$_1$ is NR$^2$R$^3$, wherein
R$^2$ and R$^3$ together with the nitrogen atom bound thereto, form a heterocycle containing 0 to 4 additional heteroatoms independently selected from —O—, —S—, and —N(R$^N$); and
L$_2$ is -D$_d$E$_e$F—, wherein
D is —CH$_2$— or —C(O)—;
E is —CH(R$_e$)—, —(C$_3$-C$_{16}$)alkyl-, —(C$_1$-C$_6$)alkoxy-, —(C$_1$-C$_6$)haloalkyl-, —(C$_3$-C$_8$)cycloalkyl-, or -aryl-, wherein
R$_e$ is —H or —NH(R$^N$);
F is a bond, —CH(R$_f$)—, or —CH$_2$CH(R$_f$)—, provided that F is covalently bonded to B, wherein
R$_f$ is —H, —(C$_1$-C$_6$)alkyl, —(C$_1$-C$_6$)haloalkyl, -aryl, —(C$_1$-C$_6$)alkylaryl, —(C$_3$-C$_8$) cycloalkyl, -heterocycloalkyl, or -heteroaryl;
d is 0 or 1; and
e is 0 or 1;
Nu is —N(SO$_2$R$^4$)—, -phenyl-O—, —N(C(O)CF$_3$)—, —(NC)C(H)C(O)—, or —C(O)O—, wherein
R$^4$ is —(C$_1$-C$_6$)alkyl, —(C$_1$-C$_6$)haloalkyl, or -aryl, wherein
the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_{d'}$E'$_{e'}$F"$_{f''}$—, wherein
D' is —CH$_2$— or —C(O)—;
E' is —CH(R$_{e'}$)—, —(C$_3$-C$_{16}$)alkyl-, or -aryl-, wherein
R$_{e'}$ is —H or —NH(R$^N$);
F" is a bond or —CH(R$_{f'}$)— provided that F" is covalently bonded to B, wherein
R$_{f'}$ is —H, —(C$_1$-C$_6$)alkyl, —(C$_1$-C$_6$)haloalkyl, -aryl, or -heteroaryl,
wherein each aryl or heteroaryl is optionally substituted with one or more groups which are each independently —NO$_2$, —CN, -halo, or —(Z$^1$)$_a$M$_b$((Z$^2$)$_c$R$^Z$);
d' is 0 or 1;
e' is 0 or 1; and
f" is 0 or 1;
and M, P, R$^A$, R$^B$, R$^N$, R$^Z$, Z$^1$, Z$^2$, a, b, c, q, and q' are as defined in formula (I). In preferred aspects, only L$_2$ is covalently bonded to B, and each L$_2$ contains only one bond to B.

In another embodiment, the invention provides a process for preparing the conjugate of formula (I), wherein
A at each occurrence is a compound of formula (XX),

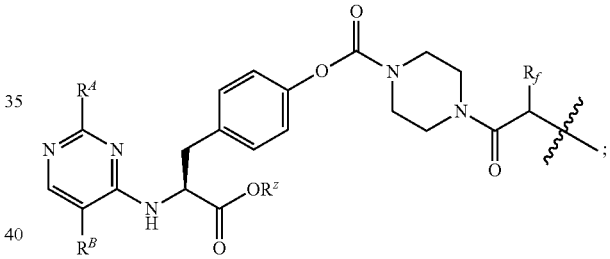

(XX)

R$_f$ is —H, —(C$_1$-C$_6$)alkyl, —(C$_1$-C$_6$)haloalkyl, -aryl, —(C$_1$-C$_6$)alkylaryl, —(C$_3$-C$_8$)cycloalkyl, -heterocycloalkyl, or -heteroaryl;
Nu is —N(SO$_2$R$^4$)—, -phenyl-O—, —N(C(O)CF$_3$)—, —(NC)C(H)C(O)—, or —C(O)O—, wherein
R$^4$ is —(C$_1$-C$_6$)alkyl, —(C$_1$-C$_6$)haloalkyl, or -aryl, wherein
the aryl is optionally substituted with 1 to 4 groups which are independently —NO$_2$, —CN, -halo, or —(Z$^1$)$_a$M$_b$((Z$^2$)$_c$R$^Z$);
L$_4$ is -D'$_{d'}$E'$_{e'}$F"$_{f''}$—, wherein
D' is —CH$_2$— or —C(O)—;
E' is —CH(R$_{e'}$)—, —(C$_3$-C$_{16}$)alkyl-, or -aryl-, wherein
R$_{e'}$ is —H or —NH(R$^N$);
F" is a bond or —CH(R$_{f'}$)— provided that F" is covalently bonded to B, wherein
R$_{f'}$ is —H, —(C$_1$-C$_6$)alkyl, —(C$_1$-C$_6$)haloalkyl, -aryl, or -heteroaryl,
wherein each aryl or heteroaryl is optionally substituted with one or more groups which are each independently —NO$_2$, —CN, -halo, or —(Z$^1$)$_a$M$_b$((Z$^2$)$_c$R$^Z$);
d' is 0 or 1;
e' is 0 or 1; and
f" is 0 or 1;

and M, P, $R^A$, $R^B$, $R^N$, $R^Z$, $Z^1$, $Z^2$, a, b, c, q, and q' are as defined in formula (I).

In another embodiment, the invention provides a process for preparing the conjugate of formula (I), wherein
A at each occurrence is a compound of formula (XX);
$R^Z$ is —H or —($C_1$-$C_6$)alkyl;
$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;
Nu is —N($SO_2R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl, wherein
    the aryl is optionally substituted with 1 to 4 groups which are independently —$NO_2$, —CN, -halo, or —($Z^1$)$_a$$M_b$(($Z^2$)$_c$$R^Z$);
$L_4$ is -$D'_d$$E'_e$$F''_{f''}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F'' is a bond or —CH($R_{f'}$)— provided that F'' is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —($Z^1$)$_a$$M_b$(($Z^2$)$_c$$R^Z$);
  d' is 0 or 1;
  e' is 0 or 1; and
  f'' is 0 or 1;
and M, P, $R^A$, $R^B$, $R^N$, $R^Z$, $Z^1$, $Z^2$, a, b, c, q, and q' are as defined in formula (I).

In another embodiment, the invention provides a process for preparing the conjugate of formula (I), wherein
A at each occurrence is a compound of formula (XX);
$R^Z$ is —H;
$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;
Nu is —N($SO_2R^4$)—, -phenyl-O—, —N(C(O)$CF_3$)—, —(NC)C(H)C(O)—, or —C(O)O—, wherein
  $R^4$ is —($C_1$-$C_6$)alkyl, —($C_1$-$C_6$)haloalkyl, or -aryl, wherein
    the aryl is optionally substituted with 1 to 4 groups which are independently —$NO_2$, —CN, -halo, or —($Z^1$)$_a$$M_b$(($Z^2$)$_c$$R^Z$);
$L_4$ is -$D'_d$$E'_e$$F''_{f''}$—, wherein
  D' is —$CH_2$— or —C(O)—;
  E' is —CH($R_{e'}$)—, —($C_3$-$C_{16}$)alkyl-, or -aryl-, wherein
    $R_{e'}$ is —H or —NH($R^N$);
  F'' is a bond or —CH($R_{f'}$)— provided that F'' is covalently bonded to B, wherein
    $R_{f'}$ is —H, —($C_1$-$C_6$)alkyl, —($C_1$-$C_6$)haloalkyl, -aryl, or -heteroaryl,
      wherein each aryl or heteroaryl is optionally substituted with one or more groups which are each independently —$NO_2$, —CN, -halo, or —($Z^1$)$_a$$M_b$(($Z^2$)$_c$$R^Z$)
  d' is 0 or 1;
  e' is 0 or 1; and
  f'' is 0 or 1;
and M, P, $R^A$, $R^B$, $R^N$, $Z^1$, $Z^2$, a, b, c, q, and q' are as defined in formula (I).

In preferred embodiments, only J, $Ar^1$, and T are covalently bonded to B, and each contains one bond to B.

In preferred processes of the invention, the azodicarbonyl compound is diethyl azocarboxylate, diisopropyl azodicarboxylate, di-tert-butyl azodicarboxylate, 4-methyl-3H-1,2,4-triazole-3,5(4H)-dione, N,N,N',N'-tetramethyl azodicarboxamide, or 1,1'-(azodicarbonyl)bis(piperidine).

In preferred processes of the invention, the solvent is an aromatic solvent, a chlorinated solvent, or an ether solvent. In particularly preferred processes of the invention, the solvent is a dichloromethane or tetrahydrofuran.

In preferred processes of the invention, the azodicarbonyl compound is dimethyl azodicarboxylate, diethyl azocarboxylate, diisopropyl azodicarboxylate, di-tert-butyl azodicarboxylate, dibenzyl azodicarboxylate, bis(2,2,2-trichloroethyl)azodicarboxylate, diphenyl azodicarboxylate, 4-methyl-3H-1,2,4-triazole-3,5(4H)-dione, N,N,N',N'-tetramethyl azodicarboxamide, 4,7-dimethyl-3,5,7-hexahydro-1,2,4,7-tetrazocin-3,8-dione, 1,1'-(azodicarbonyl)bis(piperidine), 1,1'-(azodicarbonyl)bis(4-methylpiperazine), 4,4'-(azodicarbonyl)bis(morpholine), or N,N'-bis(2-(t-butoxy)-2-oxoethyl) azodicarboxamide. In particularly preferred processes of the invention, the azodicarbonyl compound is diethyl azocarboxylate, diisopropyl azodicarboxylate, di-tert-butyl azodicarboxylate, 1,1'-(azodicarbonyl)bis(piperidine), 4-methyl-3H-1,2,4-triazole-3,5(4H)-dione, or N,N,N',N'-tetramethyl azodicarboxamide.

In preferred processes of the invention, the optional tertiary amine additive is triethylamine, N-ethyldiisopropylamine, or 4-dimethylaminopyridine.

In preferred processes of the invention, the trivalentphosphine is triphenylphosphine or tri(n-butyl)phosphine.

In preferred processes of the invention, q is from 1 to 64.
In other preferred processes of the invention, q is 1 to 32.
In still other preferred processes of the invention, q is from 1 to 16.
In yet other preferred processes of the invention, q is from 1 to 8.
The value of "q" can be an integer or any non-zero number falling within the above ranges.

Thus, in the processes of the invention, the amounts of the active compound carrying a hydroxyl group and the polymer containing nucleophilic substituents will be adjusted to achieve reaction stoichiometry appropriate to producing a product with the desired number, on average, of active drug groups per polymer molecule.

In another embodiment, the invention provides a process for preparing the conjugates of formula (I), wherein the azodicarbonyl compound is dimethyl azodicarboxylate, diethyl azocarboxylate, diisopropyl azodicarboxylate, di-tert-butyl azodicarboxylate, dibenzyl azodicarboxylate, bis(2,2,2-trichloroethyl)azodicarboxylate, diphenyl azodicarboxylate, 4-methyl-3H-1,2,4-triazole-3,5(4H)-dione, N,N,N',N'-tetramethyl azodicarboxamide, 4,7-dimethyl-3,5,7-hexahydro-1,2,4,7-tetrazocin-3,8-dione, 1,1'-(azodicarbonyl)bis(piperidine), 1,1'-(azodicarbonyl)bis(4-methylpiperazine), 4,4'-(azodicarbonyl)bis(morpholine), N,N'-bis(2-(t-butoxy)-2-oxoethyl)azodicarboxamide, bis(5-norbornen-2-ylmethyl)azodicarboxylate, bis(1H, 1H, 2H, 2H-perfluorodecyl)azodicarboxylate, bis(1H, 1H, 2H, 2H-perfluorooctyl)azodicarboxylate, bis(1H, 1H, 2H, 2H, 3H, 3H-perfluorononyl)azodicarboxylate, or a polymer supported azodicarbonyl compound.

In another embodiment, the invention provides a process for preparing the conjugate of formula (I), wherein the azodicarbonyl compound is diethyl azodicarboxylate, diisopropyl azodicarboxylate, di-tert-butyl azodicarboxylate, 4-methyl-3H-1,2,4-triazole-3,5(4H)-dione, N,N,N',N'-tetramethyl azodicarboxamide, or 1,1'-(azodicarbonyl)bis(piperidine).

In another embodiment, the invention provides a process for preparing the conjugate of formula (I), wherein related conditions are cyanomethylenetrimethylphosphorane, cyanomethylenetributylphosphorane, bis(triphenylphosphonio) oxide bis(trifluoromethanesulfonate), 3,3-dimethyl-5-(triphenylphosphonio)-1,2,5-thiadiazolidin-2-ide 1,1-dioxide, dimethyl tributylphosphoranylidenemalonate, or any of the previously listed on a polymer support.

In another embodiment, the invention provides a process for preparing the conjugate of formula (I), wherein the optional tertiary amine additive is trimethylamine, triethylamine, tri(n-propyl)amine, triisopropylamine, N-ethyldiisopropylamine, triphenylamine, tri(p-tolyl)amine, tetramethylethylenediamine, N-methylmorpholine, N-methylpiperidine, N,N-dimethylpiperazine, 4-dimethylaminopyridine, N,N-dimethylaniline, N,N-diethylaniline, N,N-diisopropylaniline, N-methylpyrrolidine, pyridine, pyrazine, pyrimidine, 1-methylimidazole, 1,8-diazabicyclo[5.4.0]undec-7-ene, 1,5-diazabicyclo[4.3.0]non-5-ene, 1,4-diazabicyclo[2.2.2]octane, or 6-(dibutylamino)-1,8-diazabicyclo[5.4.0]undec-7-ene.

In another embodiment, the invention provides a process for preparing the conjugate of formula (I), wherein the trivalentphosphine is triphenylphosphine, trimethylphosphine, triethylphosphine, tri(n-propyl)phosphine, triisopropylphosphine, tri(n-butyl)phosphine, methyl(diphenyl)phosphine, dimethyl(phenyl)phosphine, 1,2-bis-(diphenylphosphino)ethane, 1,3-bis-(diphenylphosphino)propane, 1,4-bis-(diphenylphosphino)butane, 1,5-bis-(diphenylphosphino)pentane, 1,6-bis-(diphenylphosphino)hexane, (p-dimethylaminophenyl)diphenylphosphine, diphenyl(2-pyridyl)phosphine, tris(p-dimethylaminophenyl)phosphine, t-butyl 3-(diphenylphosphino)propanoate, 2-(trimethylsilyl)ethyl 4-(diphenylphosphino)benzoate, 1-(diphenylphosphino)-4-(1H,1H,2H,2H-perfluorodecyl)benzene, di(4-(1H,1H,2H,2H-perfluorooctyl)phenyl)phosphinobenzene, or any of the previously listed on a polymer support.

In another embodiment, the invention provides a process for preparing the conjugate of formula (I), wherein the solvent is an aromatic solvent, chlorinated solvent, or an ether solvent.

In another embodiment, the invention provides a process for preparing the conjugate of formula (I), wherein the solvent is benzene, toluene, chlorobenzene, 1,2-dichlorobenzene, dichloromethane, 1,2-dichloroethane, 1,1,2,2-tetrachloroethane, diethyl ether, bis(2-methoxyethyl)ether, bis(2-ethoxyethyl)ether, 1,2-dimethoxyethane, 1,2-bis(2-methoxyethoxy)ethane, dioxane, tetrahydropyran, or tetrahydrofuran.

In another embodiment, the invention provides a process for preparing the conjugate of formula (I), wherein the solvent is benzene, toluene, dichloromethane, diethyl ether, or tetrahydrofuran.

In a preferred embodiment, the invention provides a process for preparing the conjugate of formula (I), wherein the solvent is dichloromethane or tetrahydrofuran.

In another embodiment, the invention provides a process for preparing the conjugate of formula (I), wherein the azodicarbonyl compound is dimethyl azodicarboxylate, diethyl azocarboxylate, diisopropyl azodicarboxylate, di-tert-butyl azodicarboxylate, dibenzyl azodicarboxylate, bis(2,2,2-trichloroethyl)azodicarboxylate, diphenyl azodicarboxylate, 4-methyl-3H-1,2,4-triazole-3,5(4H)-dione, N,N,N',N'-tetramethyl azodicarboxamide, 4,7-dimethyl-3,5,7-hexahydro-1,2,4,7-tetrazocin-3,8-dione, 1,1'-(azodicarbonyl)bis(piperidine), 1,1'-(azodicarbonyl)bis(4-methylpiperazine), 4,4'-(azodicarbonyl)bis(morpholine), or N,N'-bis(2-(t-butoxy)-2-oxoethyl)azodicarboxamide.

In another embodiment, the invention provides a process for preparing the conjugate of formula (I), wherein the azodicarbonyl compound is diethyl azocarboxylate, diisopropyl azodicarboxylate, di-tert-butyl azodicarboxylate, 1,1'-(azodicarbonyl)bis(piperidine), 4-methyl-3H-1,2,4-triazole-3,5(4H)-dione, or N,N,N',N'-tetramethyl azodicarboxamide.

In preferred embodiment, the invention provides a process for preparing the conjugate of formula (I), wherein the optional tertiary amine additive triethylamine, N-ethyldiisopropylamine, or 4-dimethylaminopyridine.

In another embodiment, the invention comprises the process for preparing the conjugate of formula (I), wherein the trivalentphosphine is triphenylphosphine or tri(n-butyl)phosphine.

In another embodiment, the invention provides a process for preparing the conjugate of formula (I), wherein q is 1 to 64.

In another embodiment, the invention provides a process for preparing the conjugate of formula (I), wherein q is 1 to 32.

In another embodiment, the invention provides a process for preparing the conjugate of formula (I), wherein q is 1 to 16.

In another embodiment, the invention provides a process for preparing the conjugate of formula (I), wherein q is 1 to 8.

In another embodiment, the invention provides a process for preparing the conjugate of formula (I), wherein q is 1 to 4.

As noted above, this invention provides processes for the preparation of conjugates of agricultural, therapeutic, and food additive compounds. The conjugates comprise one or more active compounds covalently attached to a polymer at one or multiple sites, where the resulting conjugates have the same type of activity as the active compound. For example, if the attached active compound itself is a VLA-4 antagonist, then the conjugate is also a VLA-4 antagonist.

In one aspect, the active compounds and resulting conjugates are compounds that inhibit leukocyte adhesion and, in particular, leukocyte adhesion mediated, at least in part, by $\alpha_4$ integrins.

The process of the instant invention employs the "Mitsunobu" reaction, a condensation reaction of alcohols with a nucleophile in the presence of a trivalentphosphine, an appropriate azodicarboxylate, and an optional tertiary amine additive.

In preferred reactions, a primary or secondary alcohol substituent of at least one active compound reacts with polymeric nucleophiles in the presence of a trivalentphosphine, azodicarbonyl reagent, and an optional tertiary amine additive, in at least one solvent, to afford the conjugates. The type of bond that may be formed by reacting a primary or secondary alcohol substituent of an active compound with a polymeric nucleophile are diverse; for example, carbon-oxygen bonds, carbon-nitrogen bonds, carbon-sulfur bonds, and carbon-carbon bonds all may be formed by reaction with the appropriate nucleophile as recognized by one skilled in the art.

Nucleophilic functional groups that react with primary or secondary alcohol substituents of active compounds include, for example, carboxylic acids, phenols, $\beta$-ketoesters, sulfonamides, trifluoroacetamides, arylthiols, $\alpha$-cyanoacetates, and the like. Other examples of nucleophiles that can be utilized in the process of the invention can be found in Organic Reactions, 1992, 42, 335-656, which is incorporated herein by reference in its entirety.

Examples of trivalentphosphines include, but are not limited to, triphenylphosphine, trimethylphosphine, triethylphosphine, tri(n-propyl)phosphine, triisopropylphosphine, tri(n-butyl)phosphine, methyl(diphenyl)phosphine, dimethyl(phenyl)phosphine, 1,2-bis-(diphenylphosphino)ethane, 1,3-bis-(diphenylphosphino)propane, 1,4-bis-(diphenylphosphino)butane, 1,5-bis-(diphenylphosphino)pentane, 1,6-bis-(diphenylphosphino)hexane, (p-dimethylaminophenyl)diphenylphosphine, diphenyl(2-pyridyl)phosphine, tris(p-dimethylaminophenyl)phosphine, t-butyl 3-(diphenylphosphino)propanoate, 2-(trimethylsilyl)ethyl 4-(diphenylphosphino)benzoate, 1-(diphenylphosphino)-4-(1H,1H,2H,2H-perfluorodecyl)benzene, di(4-(1H,1H,2H,2H-perfluorooctyl)phenyl)phosphinobenzene, and any of the previously listed phosphines covalently bonded to a polymer support. A preferred trivalentphosphines are triphenylphosphine and tri(n-butyl)phosphine.

The azodicarbonyl reagents are generally esters or amides of azodicarboxylic acids, and include, but are not limited to, dimethyl azodicarboxylate, diethyl azocarboxylate, diisopropyl azodicarboxylate, di-tert-butyl azodicarboxylate, dibenzyl azodicarboxylate, bis(2,2,2-trichloroethyl)azodicarboxylate, diphenyl azodicarboxylate, 4-methyl-3H-1,2,4-triazole-3,5(4H)-dione, N,N,N',N'-tetramethyl azodicarboxamide, 4,7-dimethyl-3,5,7-hexahydro-1,2,4,7-tetrazocin-3,8-dione, 1,1'-(azodicarbonyl)bis(piperidine), 1,1'-(azodicarbonyl)bis(4-methylpiperazine), 4,4'-(azodicarbonyl)bis(morpholine), N,N'-bis(2-(t-butoxy)-2-oxoethyl)azodicarboxamide, bis(5-norbornen-2-ylmethyl)azodicarboxylate, bis(1H, 1H, 2H, 2H-perfluorodecyl)azodicarboxylate, bis(1H, 1H, 2H, 2H-perfluorooctyl)azodicarboxylate, bis(1H, 1H, 2H, 2H, 3H, 3H-perfluorononyl)azodicarboxylate, and any of the previously listed azodicarbonyl compounds covalently bonded to a polymer support.

Preparation of Conjugates of the Invention Utilizing related reaction conditions include use of reagents which activate primary and secondary alcohols toward reaction with nucleophiles through the proposed formation of an alkoxyphosphonium intermediate which is common to all of these methods. Such reagents include cyanomethylenetrimethylphosphorane and cyanomethylenetributylphosphorane (Tsunoda et al., Tetrahedron Lett., 1994, 35, 5081-2; Tsunoda et al., Tetrahedron Lett., 1996, 37, 2459-62; Sakamoto et al., Chem. Pharm. Bull., 2003, 51, 474-6), bis(triphenylphosphonio)oxide bis(trifluoromethanesulfonate) (Elson et al., Org. Biomol. Chem., 2003, 1, 2958-65), 3,3-dimethyl-5-(triphenylphosphonio)-1,2,5-thiadiazolidin-2-ide 1,1-dioxide (Castro et al., J. Org. Chem., 1994, 59, 2289-91), dimethyl tributylphosphoranylidenemalonate (McNulty et al., J. Org. Chem., 2003, 68, 1597-600), and any of the previously listed on a polymer support.

DEFINITIONS

The term "active compound" as used herein, means any therapeutic, agricultural, or food additive compound that exhibits a beneficial pharmacodynamic effect when administered to a human or animal. Examples of active compounds include VLA-4 antagonists as defined herein.

The term "aliphatic" as used herein, means any group containing an alkyl, alkenyl, or alkynyl group as defined herein.

The term "alkanoyl" as used herein, means an alkyl group, as defined herein, appended to the parent molecular moiety through a carbonyl group, as defined herein. Representative examples of alkanoyl include, but are not limited to, acetyl, 1-oxopropyl, 2,2-dimethyl-1-oxopropyl, 1-oxobutyl, and 1-oxopentyl.

The term "alkenyl" as used herein, means a straight or branched chain hydrocarbon containing at least one carbon-carbon double bond. Representative examples of alkenyl include, but are not limited to, ethenyl, 2-propenyl, 2-methyl-2-propenyl, 3-butenyl, 4-pentenyl, and 5-hexenyl.

The term "alkoxy" as used herein, means an alkyl group, as defined herein, appended to the parent molecular moiety through an oxygen atom. Representative examples of alkoxy include, but are not limited to, methoxy, ethoxy, n-propoxy, 2-propoxy, n-butoxy, tert-butoxy, n-pentyloxy, and n-hexyloxy.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl" as used herein, means a straight or branched chain hydrocarbon. Representative examples of alkyl include, but are not limited to, methyl, ethyl, n-propyl, iso-propyl, n-butyl, sec-butyl, iso-butyl, tert-butyl, n-pentyl, isopentyl, and neopentyl.

The term "alkylaryl" as used herein, means an alkyl group, as defined here, covalently bonded to the parent molecular moiety through an aryl group, as defined herein.

The term "alkylene oxide" as used herein, means a heterocycle, as defined herein, wherein only one oxygen is present. The heterocycle may be saturated or unsaturated, but not aromatic. Examples of alkylene oxides include, but are not limited to, ethylene oxide, propylene oxide, 2-butyloxirane, 2,3-diethyloxirane, oxetane, 2-methyloxetane, tetrahydrofuran, 2,3-dihydropyran, and tetrahydropyran.

The term "alkylene glycol" as used herein, means an alkyl diol. Examples of alkylene glycols include, but are not limited to, ethylene glycol, propylene glycol, 1,4-butanediol, 1,5-pentanediol, 1,6-hexanediol, and 1,2-hexanediol.

The term "alkynyl" as used herein, means a straight or branched chain hydrocarbon group containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "antagonist" as used here in, means a compound capable of eliciting a pharmacodynamic effect, in vivo or in vitro, through inhibition of the normal physiological function of a biological receptor in a competitive or non-competitive fashion.

The term "aroyl" as used herein, means an aryl group, as defined herein, appended to the parent molecular moiety through a carbonyl group, as defined herein. Representative examples of aroyl include, but are not limited to, benzoyl and naphthoyl.

The term "aryl," as used herein, means phenyl or a "bicyclic aryl" or a "tricyclic aryl". The "bicyclic aryl" is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The "tricyclic aryl" is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, dihydroanthracenyl, fluorenyl, and tetrahydrophenanthrenyl.

The term "arylalkoxy" as used herein, means an aryl group, as defined herein, appended to the parent molecular moiety through an alkoxy group, as defined herein. The aryl group is bonded to the alkoxy group through any carbon in the alkyoxy group and the parent molecule is bonded to the substituent through the oxygen terminus. Examples of arylalkoxy groups include, but are not limited to, benzyloxy, naphth-2-ylmethoxy, and 9-Fluorenylmethoxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl, naphth-2-ylmethoxycarbonyl and 9-fluorenylmethoxycarbonyl.

The term "carbonyl" as used herein, means a —C(O)— group.

The term "cyclic" as used herein, means any aryl, heteroaryl, cycloalkyl, and heterocycle as defined herein.

The term "cycloalkanoyl" as used herein, means cycloalkyl group, as defined herein, appended to the parent molecular moiety through a carbonyl group, as defined herein. Representative examples of cycloalkanoyl include, but are not limited to, cyclopropylcarbonyl, 2-cyclobutylcarbonyl, and cyclohexylcarbonyl.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1] heptyl, and adamantyl.

The term "end group" as used herein, means the entity covalently bonded at the termini of a polymer, as defined herein.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, 2,2,2-trifluoroethyl, pentafluoroethyl, and 2-chloro-3-fluoropentyl.

The term "heteroaroyl" as used herein, means a heteroaryl group, as defined herein, appended to the parent molecular moiety through a carbonyl group, as defined herein. Representative examples of heteroaroyl include, but are not limited to, fur-3-ylcarbonyl, 1H-imidazol-2-ylcarbonyl, 1H-imidazol-4-ylcarbonyl, pyridin-3-ylcarbonyl, pyridin-4-ylcarbonyl, pyrimidin-5-ylcarbonyl, pyrimidin-2-ylcarbonyl, thien-2-ylcarbonyl, and thien-3-ylcarbonyl.

The term "heteroaryl," as used herein, means a "monocyclic heteroaryl" or a "bicyclic heteroaryl." The "monocyclic heteroaryl" is a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The "bicyclic heteroaryl" consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "heterocycle" or "heterocyclic" as used herein, means a "monocyclic heterocycle" or a "bicyclic heterocycle" or a "tricyclic heterocycle." The "monocyclic heterocycle" is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The "bicyclic heterocycle" is a monocyclic heterocycle fused to a phenyl group, or a monocyclic heterocycle fused to a cycloalkyl, or a monocyclic heterocycle fused to a cycloalkenyl, or a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle, or a bicyclic heterocycle fused to a monocyclic heteroaryl. The "tricyclic heterocycle" is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9, 9a-hexahydrodibenzo[b,d]thienyl.

The term "heterocycloyl" as used herein, means a heterocycle, as defined herein, appended to the parent molecular moiety through a carbonyl group, as defined herein. The heterocycle may be bonded to the carbonyl at any carbon or heteroatom contained in the heterocycle.

The term "hub molecule" used herein, means a molecule that covalently bonds two polymer, oligomer, and/or monomer portions to them. Non-limiting examples of such hub molecules are ethylene glycol, propylene glycol, α,ω-alkyl diols, phthalic acid, isophthalic acid, terephthalic acid, succinic acid, malonic acid, maleic acid, adipic acid, α,ω-alkyl dioic acids, acetylene dicarboxylic acid. Further encompassed are "branched-arm hub molecules" wherein included are molecules that covalently bond three or more polymer, oligomer, and/or monomer portions to them. Example of branched-arm hubs molecules include, but are not limited to, glycerol (1,2,3-propanetriol), pentaerythritol, 1,2,4-benzenetriol, glucose (in its pyranose form), ethylenediamine tetraacetic acid, amino acids, 3- or 4-aminosalicylic acid, 1,3,5-benzene tricarboxylic acid, 1,3-diamino-2-hydroxypropane, glucosamine, sialic acid, and dendrimers, as defined herein.

The term "monomer" as used herein, means any individual molecule that may be used in the preparation of a polymer that becomes part of the polymer repeating unit. Examples of monomers include, but are not limited to, methyl methacrylate, methyl acrylate, acrylonitrile, acrylic acid, N,N-dimethylacrylamide, styrene, maleic anhydride, epichlorohydrin, vinyl chloride, vinyl acetate, caprolactone, caprolactam, ethylene glycol, ethylene oxide, propylene glycol, propylene oxide, tetrahydrofuran, 1,6-diaminohexane, 1,6-hexanedioic acid, 1,6-hexanedioyl chloride, 2-ethyl-1,3-oxazole, ethylenediamine, hydroquinone, 1,4-diacetoxybenzene, 1,4-diiodobenzene, 1,4-diethynylbenzene, phthalic anhydride, terephthalic acid, isophthalic acid, terephthaloyl chloride, perfluorobiphenyl, and norbornene.

The term "nucleophile" as used herein, means a reagent which brings a pair of electrons to a substrate.

The term "nucleophilic" as used herein, means either a reaction wherein a reagent brings a pair of electrons to a substrate or a reagent or functional group capable as reacting as a nucleophile, as defined herein.

The term "PEG" as used herein, refers to poly(ethylene glycol).

The term "mPEG" or "m-PEG" as used herein, refers to poly(ethylene glycol) mono methyl ether.

The term "oligomer" as used herein, means a macromolecule composed of monomers, as defined herein, wherein fewer than 10 monomers comprise the macromolecule.

The term "polymer" as used herein, refers to biocompatible, water-soluble, substantially non-immunogenic macromolecules formed from multiple monomers, typically, greater than 10 monomers, as defined herein. Preferably, the polymer is non-ionic and biocompatible as measured by lack of toxicity at the molecular weights and dosages used. Examples of suitable polymers include, but are not limited to, poly(ethylene glycol), poly(vinyl alcohol), poly(allyl amine), poly(4-hydroxystyrene), dextran, cellulose, poly(L-aspartic acid), poly(L-lysine), poly(L-glutamic acid), and poly(N-(2-hydroxypropyl)methacrylamide). Further encompassed in the term "polymer" are "co-polymers," "graft-" or "comb-polymers," "star polymers," "hyperbranched polymers," and "dendritic polymers" or "dendrimers." A polymer may be composed from only one type of monomer or a combination of two or more monomers. In the former case, the polymer may be atactic, syndiotactic, or isotactic. In the latter case, a "co-polymer" is formed, which may be a random, alternating, "block", or "multi-block co-polymer". A "block co-polymer" consists of one terminus of each of two individual polymers covalently bonded to one another; the two polymers may alternatively be joined by covalent bonding through a hub molecule, as defined herein. A "multi-block co-polymer" consists of individual polymers connected at their termini in series directly to one another, or through a hub molecule, so as to form a linear macromolecule; each individual polymer may be the same or different. In the case of block- and multi-block co-polymers, each individual polymer therein may be atactic, syndiotactic, or atactic. Examples of co-polymers and block co-polymer include the commercially available poly(styrene-co-maleic anhydride), poly(divinylether-co-maleic anhydride), bis[poly(ethylene glycol)]adipate diol, bis[poly(ethylene glycol)]phthalate diol, and the like. Another class of polymer encompassed herein are "graft-" or "comb-polymers," wherein one or more polymer is covalently bonded to a second polymer at one or more locations along the first polymer chain, as are familiar to those skilled in the art. For example, poly(poly(ethylene glycol mono methyl ether) methacrylate) is a graft- or comb-polymer, wherein poly(ethylene glycol mono methyl ether) polymers are covalently bonded to a poly(methacrylic acid) polymer. The term also encompasses "star polymers," wherein 3 or more polymers are connected to a branched-arm hub molecule, as defined herein; each polymer of the star polymer may be the same or different. Example of star polymers include, but are not limited to, glycerol tris[poly(ethylene glycol)]ether, pentaerythriol tetrakis[poly(ethylene glycol)]ether, and hexaglycerol hexakis[poly(ethylene glycol)]ether. The term also encompasses "dendritic polymers" or "dendrimers" which are polymers prepared through iterative chemical reactions starting from a branched-arm hub or hub molecule as defined herein. Alternatively, dendrimers may be moieties prepared though covalent bonding of individual dendrimers to a branched-arm hub or hub molecule; in this case, the same or one or more different dendrimers may be used. Examples of appropriate dendrimers include, but are not limited to, PAMAM (polyamido amine) and poly(propyleneimine) dendrimers. Further included are "hyperbranched polymers," wherein multiple, random branch points exist in a polymer, due to 3 or more reactive sites present in one or more monomer used in their preparation. For example, addition of 1,3,5-benzenetricarboxylic acid in the preparation of a poly(ester) will result in formation of a hyperbranched poly(ester).

The term "poly(oxyalkylene) s" as used herein, means polymers, as defined herein, composed from alkylene oxide or alkylene glycol monomers, as defined herein. Examples of poly(oxyalkylene)s include, but are not limited to poly(ethylene glycol), poly(propylene glycol), poly(isopropylene glycol), poly(tetrahydrofuran), poly(ethylene oxide), poly (propylene oxide), and the like.

The term "polymeric nucleophile" as used herein, means a polymer, as defined herein, containing nucleophiles, as defined herein, as either part of the polymer backbone, part of a side group, end group, or any combination of the preceding, as defined herein. Examples of polymeric nucleophiles include PEG bis-N-(p-tolyl)sulfonamide, PEG bis(succinamic acid), poly(4-hydroxystyrene), and poly(acrylic acid).

The term "PPG" as used herein, means poly(propylene glycol).

The term "primary alcohol" as used herein, means any compound containing an —OH functional group, wherein the carbon atom, to which the oxygen is bonded, itself is singly bonded to only one other substituent that is not hydrogen. Examples of primary alcohols include, but are not limited to, methanol, ethanol, n-propanol, benzyl alcohol, tetrahydrofurfuryl alcohol, cyclopropylmethanol, 2-thiophenemethanol, 2-methyl-1-propanol, and 2,2-dimethyl-1-propanol.

The term "primary amine" as used herein, means any compound containing an —NH$_2$ functional group. Examples of primary amines include, but are not limited to, methylamine, n-propylamine, cyclohexylamine, aniline, isopropylamine, and 2-aminopyridine.

The term "secondary alcohol" as used herein, means any compound containing an —OH functional group, wherein the carbon atom, to which the oxygen is bonded, itself is singly bonded to only two other substituents that are not hydrogen. The carbon to which the oxygen is bonded may be part of a cycloalkyl or heterocycloalkyl, as defined herein. Examples of secondary alcohols include isopropanol, 2-butanol, 2-pentanol, 3-pentanol, cyclopropanol, cyclohexanol, 4-hydroxy-1-methylpiperidine, 1-phenylethanol, and 1-(2-naphthyl)ethanol.

The term "side group" as used herein, refers to any chemical entity covalently bonded via a single bond to a polymer chain.

The term "tertiary amine" as used herein, means any compound containing nitrogen, wherein the nitrogen itself makes only three single bonds to substituents that are not hydrogen. The nitrogen may endo- or exocyclic, but not part of an amide, imide, sulfonamide, or sulfinamide. Examples of tertiary amines include triethylamine, N-ethyldiisopropylamine, tricyclohexylamine, N-methylmorpholine, N-methylpiperidine, pyridine, pyrazine, pyrimidine, triethanolamine, and N,N-dimethylaniline.

Conjugate Preparation

For clarity, the following schemes for preparation of polymeric nucleophiles and active compound conjugates are illustrated using m-PEG and m-PEG-NH$_2$ as starting materials. Those skilled in the art will recognize that any —OH or —NH$_2$ containing polymer may be utilized in place of m-PEG-OH or m-PEG-NH$_2$. In addition, those skilled in the art will recognize that multiple functional groups may be present in any polymer which may be used according to the methods of the invention.

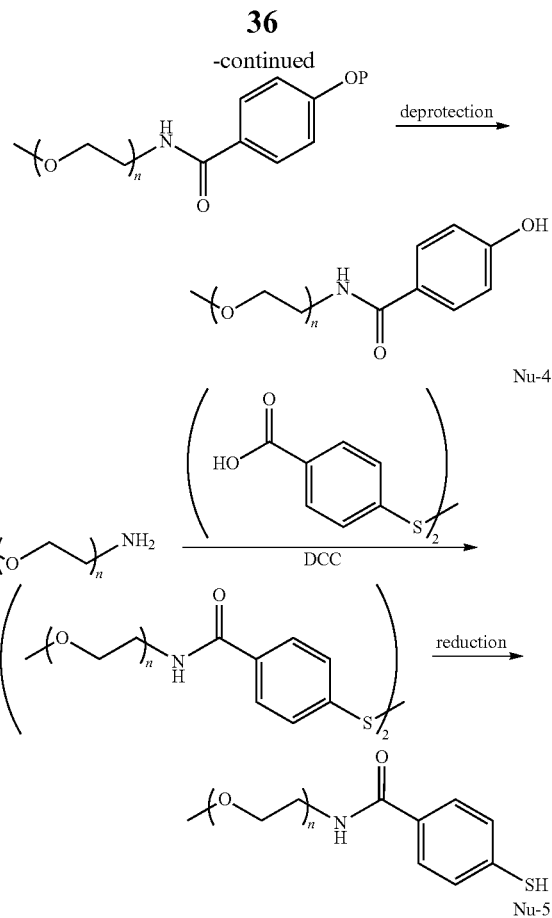

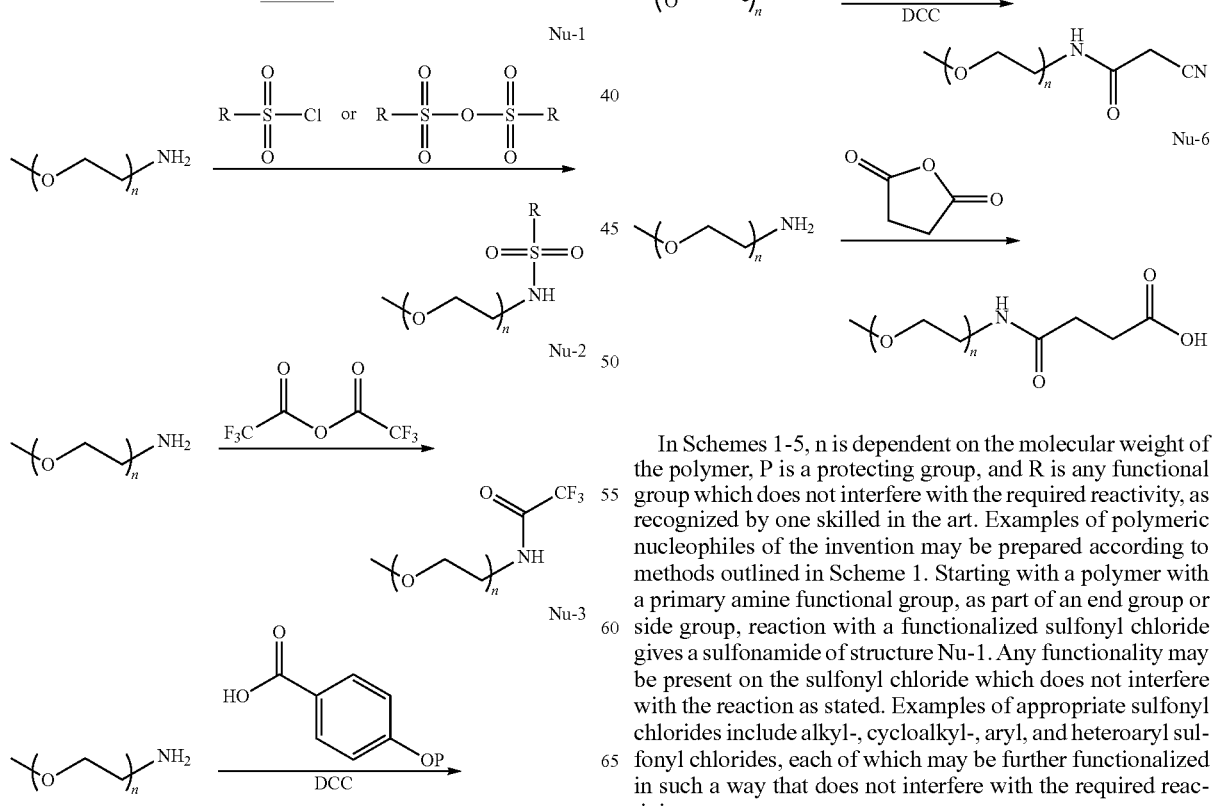

In Schemes 1-5, n is dependent on the molecular weight of the polymer, P is a protecting group, and R is any functional group which does not interfere with the required reactivity, as recognized by one skilled in the art. Examples of polymeric nucleophiles of the invention may be prepared according to methods outlined in Scheme 1. Starting with a polymer with a primary amine functional group, as part of an end group or side group, reaction with a functionalized sulfonyl chloride gives a sulfonamide of structure Nu-1. Any functionality may be present on the sulfonyl chloride which does not interfere with the reaction as stated. Examples of appropriate sulfonyl chlorides include alkyl-, cycloalkyl-, aryl, and heteroaryl sulfonyl chlorides, each of which may be further functionalized in such a way that does not interfere with the required reactivity.

Examples of alkylsulfonyl chlorides which may be used according to the invention include 1-butanesulfonyl chloride, 1-hexanesulfonyl chloride, 1-Propanesulfonyl chloride, 2,2,2-trifluoroethanesulfonyl chloride, isobutanesulfonyl chloride, 2-propanesulfonyl chloride, 3-[2,5-bis(bromomethyl)-4-methoxyphenoxy]-1-propanesulfonyl chloride, 3-(4-methoxyphenoxy)-1-propanesulfonyl chloride, phenylmethanesulfonyl chloride, ethanesulfonyl chloride, methanesulfonyl chloride, nonafluoro-1-butanesulfonyl chloride, trichloromethanesulfonyl chloride, and trifluoromethanesulfonyl chloride.

Examples of cycloalkylsulfonyl chlorides which may be used according to the invention include cyclopropanesulfonyl chloride, and 10-camphorsulfonyl chloride.

Examples of arylsulfonyl chlorides suitable for use in this invention include, but are not limited to, benzenesulfonyl chloride, 1-naphthalenesulfonyl chloride, 2-naphthalenesulfonyl chloride, p-toluenesulfonyl chloride, o-toluenesulfonyl chloride, 4-acetamidobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-di(trifluoromethyl)benzenesulfonyl chloride, 4-fluorobenzenesulfonyl chloride, 4-methoxybenzenesulfonyl chloride, 2-methoxycarbonyl-benzenesulfonyl chloride, 4-methylamidobenzenesulfonyl chloride, 4-nitrobenzenesulfonyl chloride, 4-trifluoromethyl-benzenesulfonyl chloride, 4-trifluoromethoxybenzenesulfonyl chloride, 2,4,6-trimethylbenzenesulfonyl chloride, Examples of heteroaryl sulfonyl chlorides which may be used according to the invention include 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide, or sulfonic acid anhydride may be used in place of the sulfonyl chloride in the above reaction.

Scheme 2

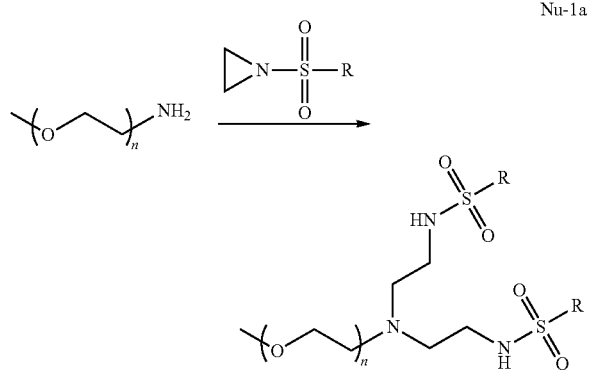

The number of nucleophiles attached to a polymer can be amplified by reaction of a primary amine end group or side group with a N-sulfonyl aziridine, as illustrated in Scheme 2. The amine can react with two equivalents of the N-sulfonyl aziridine to yield up to a two-fold increase in available N-sulfonamide nucleophiles for reaction with active compounds.

Examples of appropriate N-sulfonyl aziridines include, but are not limited to, 1-(benzylsulfonyl)aziridine, 1-(p-tosyl)aziridine, 1-(phenylsulfonyl)aziridine, methylsulfonylaziridine, 1-(n-butylsulfonyl)aziridine, and the like.

Polymeric nucleophiles containing N-trifluoroacetyl groups, such as Nu-2 in Scheme 1, may be prepared by treating an amine functionalized polymer with trifluoroacetic anhydride or trifluoroacetyl chloride.

Polymeric nucleophiles containing phenol groups, such as Nu-3 in Scheme 1 may be prepared by a coupling an amine functionalized polymer with a protected hydroxybenzoic acid under dehydrating conditions using coupling agents such as dicyclohexylcarbodiimide (DCC), diisopropylcarbodiimide (DIC), N-(3-dimethylaminopropyl)-N'-ethylcarbodiimide (EDC), N-cyclohexyl-N'-(2-morpholinoethyl)carbodiimide metho-p-toluenesulfonate (CMC), diethylazodicarboxylate (DEAD) and triphenylphosphine, benzotriazol-1-yloxy)tris(dimethylamino)phosphonium hexafluorophosphate (BOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(benzotriazol-1-yl)-N,N,N',N'-bis(tetramethylene)uronium hexafluorophosphate (HBPyU), (benzotriazol-1-yloxy)dipiperidinocarbenium hexafluorophosphate (HBPipU), bromotripyrrolidinophosphonium hexafluorophosphate (PyBroP), O-(3,4-dihydro-4-oxo-1,2,3-benzotriazin-3-yl)-N,N,N',N'-tetramethyluronium tetrafluoroborate (TDBTU), O-(2-oxo-1(2H)pyridyl)-N,N,N',N'-tetramethyluronium tetrafluoroborate (TPTU), O-(1,2-dihydro-2-oxo-1-pyridyl)-N,N,N',N'-bis(tetramethylene)uronium hexafluorophosphate (HPPyU), O-[ethoxycarbonyl)cyanomethylenamino]-N,N,N',N'-tetramethyluronium tetrafluoroborate (TOTU), bromotris(dimethylamino)phosphonium hexafluorophosphate (BroP), chlorotripyrrolidinophosphonium hexafluorophosphate (PyCloP), chlorodipyrrolidinocarbenium hexafluorophosphate (PyClU), chloro-dipiperidinocarbenium hexafluorophosphate (PipClU), chloro-N,N,N',N'-bis(tetramethylene)formamidinium tetrafluoroborate, 2-chloro-1,3-dimethylimidazolidinium hexafluorophosphate, 2-chloro-1,3-imidazolidinium tetrafluoroborate, S-(1-oxido-2-pyridyl)-N,N,N'N'-tetramethylthiuronium tetrafluoroborate (TOTT), 1-hydroxybenzotriazole (HOBt), 1-hydroxy-7-azabenzotriazole (HOAt), and the like, in the presence of a tertiary amine, to form the amide. Useful tertiary amines include, but are not limited to, triethylamine, ethyldiisopropylamine, and N,N-dimethylaminopyridine. Appropriate protecting groups include, but are not limited to, t-butyl and benzyl. Removal of the alcohol protecting group under conditions familiar to those skilled in the art, yields the nucleophilic polymer containing phenol groups, as illustrated by Nu-3 in Scheme 1.

Analogously, polymeric nucleophiles containing thiophenol groups, such as Nu-4 in Scheme 1, may be prepared by a coupling an amine functionalized polymer with a protected mercaptobenzoic acid under dehydrating conditions to form the amide. As shown in Scheme 1, 4,4'-dithiodibenzoic acid may be used, wherein the dithio linkage acts as a protecting group for the thiophenol. Alternatively, a protected mercaptobenzoic acid may be used, for example, 4-(tert-butylthio)benzoic acid. Removal of the thiol protecting group, under conditions familiar to those skilled in the art, or reduction of the dithio intermediate with dithiothreitol (DTT), dithioerythreitol (DET), 2-metcaptoethanol, reduced glutathione (GSH), tris(2-carboxyethyl)phosphine, tributylphosphine, 2,3-dihydrolipoic acid, 2,3-dimercaptopropanol (British anti-Lewisite, BAL), 2,3-dimercapto-1-propanesulfonate, sodium borohydride, or the like, yields the nucleophilic polymer containing thiophenol groups, as illustrated by Nu-4 in Scheme 1.

Polymeric nucleophiles containing N-(alpha-cyano acetyl) groups, such as Nu-5 in Scheme 1, may be prepared by a coupling an amine functionalized polymer with cyanoacetic acid under dehydrating conditions to form the amide.

Polymeric nucleophiles containing carboxylic acid groups, such as Nu-6 in Scheme 1, may be prepared by reaction of a cyclic anhydride with an amine functionalized polymer, to yield carboxamic acid groups. Appropriate cyclic anydrides include, but are not limited to, succinic anhydride, 3-oxabicyclo[3.1.0]hexane-2,4-dione, 3,3-tetramethyleneglutaric anhydride, 1,2-cyclohexanedicarboxylic anhydride, diglycolic anhydride, (±)-camphoric acid anhydride, 1-cyclopentene-1,2-dicarboxylic anhydride, 2,2-dimethylglutaric anhydride, 2,2-dimethylsuccinic anhydride, 2,3-dichloromaleic anhydride, 2,3-diethylmaleic anhydride, 2,3-diphenylmaleic anhydride, maleic anhydride, bicyclo[2.2.1]hept-5-ene-2,3-dicarboxylic anhydride, 1,2-cyclohexanedicarboxylic anhydride, glutaric anhydride, and hexafluoroglutaric anhydride.

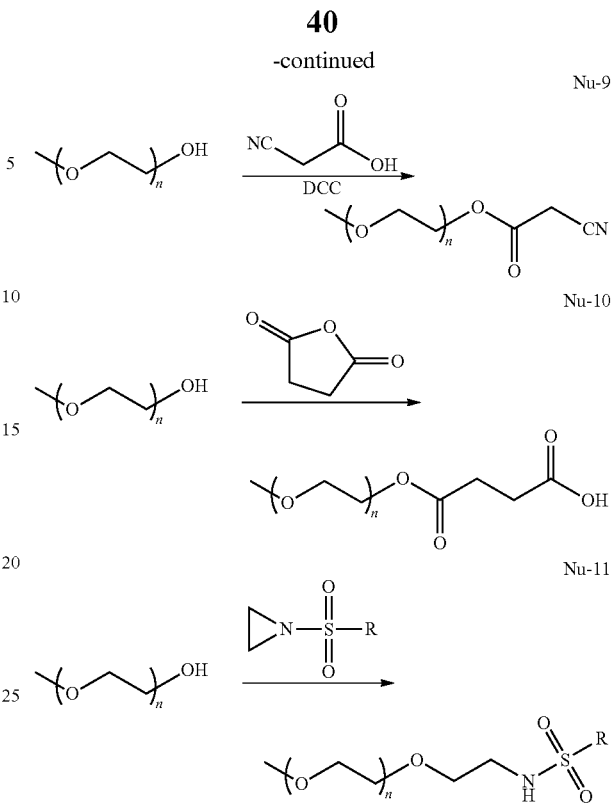

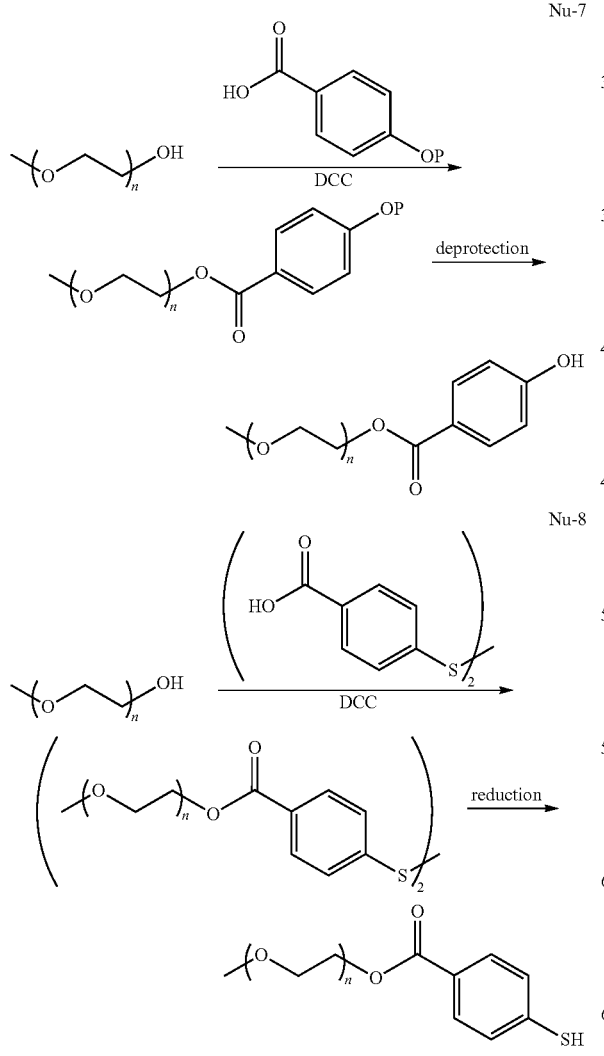

As illustrated in Scheme 3, polymeric nucleophiles of the invention may also be prepared starting with an alcohol functionalized polymer, such as mPEG or poly(vinyl alcohol). According to conditions similar to those described in Scheme 1 for the preparation of Nu-3 through Nu-6, analogous polymeric nucleophiles Nu-7 through Nu-10 may be prepared, to yield ester linkages to the polymer rather than amides. Nu-11, in Scheme 3, may be prepared with an alcohol and N-sulfonyl aziridine to introduce a N-sulfonamide nucleophile. Unlike the example of Nu-1a in Scheme 2, the alcohol can only react with one equivalent of N-sulfonyl aziridine, therefore, no nucleophile amplification is possible.

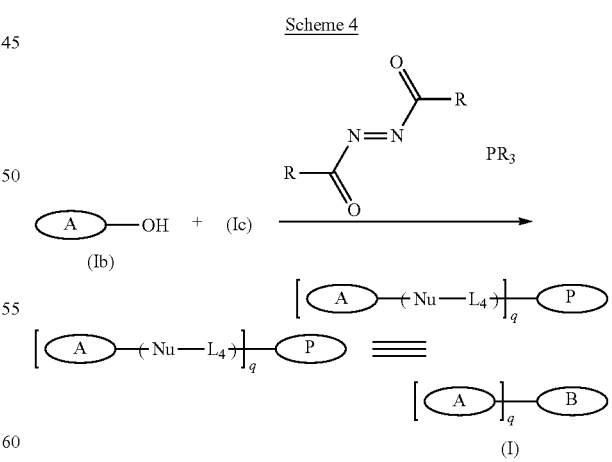

Conjugation of primary or secondary alcohol of active compounds of formula (Ib) with polymeric nucleophiles of formula (Ic) is ultimately accomplished through the utilization of "Mitsunobu" or related conditions, as are familiar those who are skilled in the art, as illustrated in Scheme 4. "Mitsunobu" reaction conditions comprise a trivalentphosphine, azodicarbonyl compound, and optionally, a tertiary amine, to accomplish a dehydrative bond forming reaction. The nucleophile, such as (Ic), used in a "Mitsunobu" reaction must contain a hydrogen whose pKa is less than 13 to be active under the reaction conditions. Preferably, the pKa of the hydrogen is less than 11. Through use of "Mitsunobu" conditions, conjugates of formula (I) are prepared.

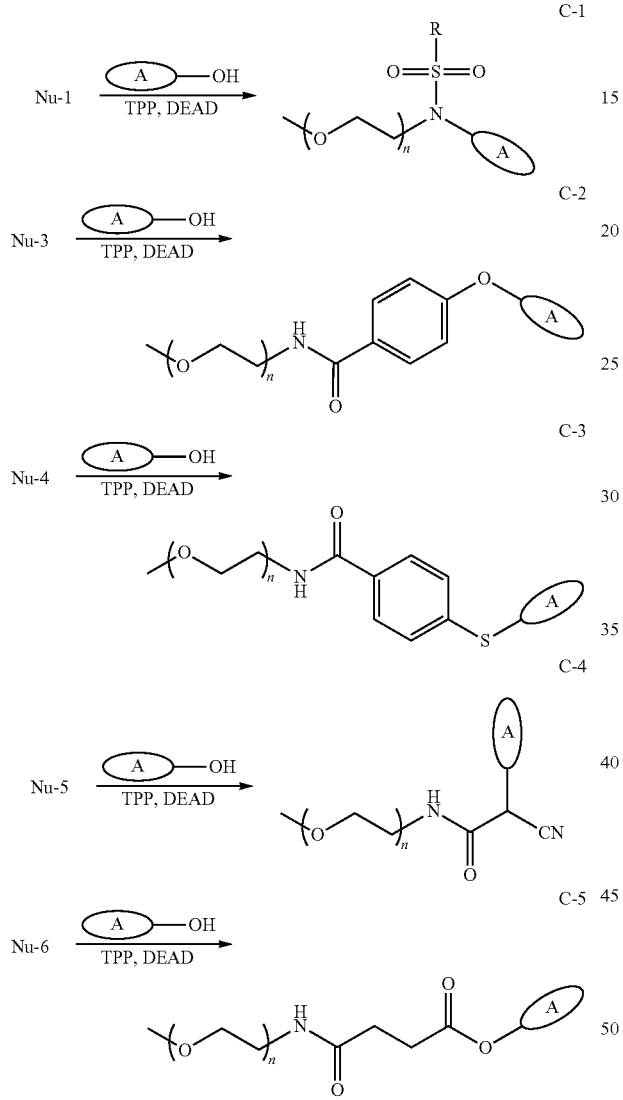

As illustrated in Scheme 5, any of a variety of bond may be formed using the "Mitsunobu" reaction a polymeric nucleophile, and an alcohol substituent of an active compound, A. Using the polymeric nucleophile Nu-1 and Nu-3 through Nu-6 the conjugates C-1 through C-5 are prepared. In the example of conjugate C-1, the N-sulfonyl amide nucleophile, Nu-1, reacts to form a C—N bond. In the example of C-2, a C—O bond is formed between the phenol nucleophile, Nu-3, and the active compound, in this case, producing an ether-linked conjugate. Analogously, a C—S bond is formed between the thiophenol nucleophile, Nu-4, and the active compound to yield conjugate C-3. A C—C bond is formed by the alpha-cyano acetamide nucleophile, Nu-5, to yield C-4. Finally, an ester linkage between the polymer nucleophile Nu-6 and the active compound is formed on reaction of the carboxylic acid nucleophile with the active compound, to produce conjugate C-5.

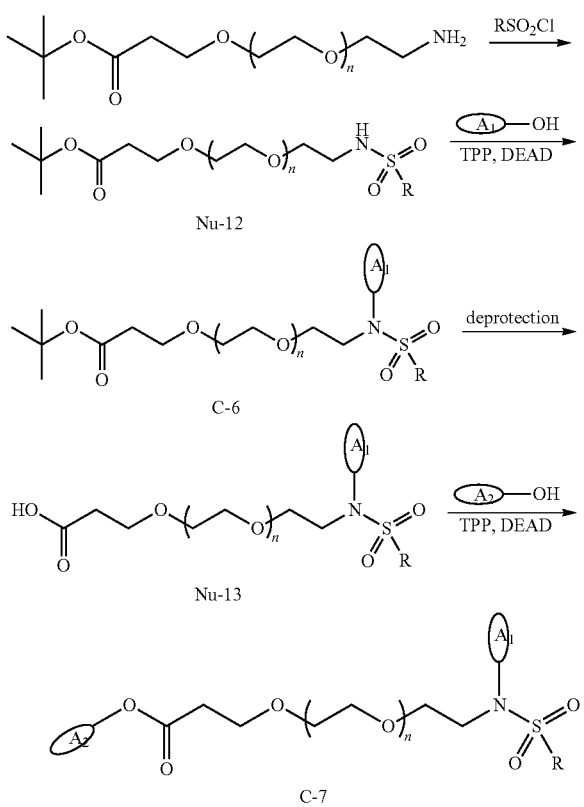

Optionally, a heterofunctional polymer may be used in conjugate preparation which contains two or more distinctly different end or side groups, at least one of which is suitably protected. An example would be as illustrated in Scheme 6, a PEG with one amino end group and one t-butyl ester protected carboxylic acid end group. By protecting one end of the polymer chain, two different active compounds may be attached. For example, reacting the amino end group with a sulfonyl chloride, yields the nucleophile, Nu-12. Further reaction with an active compound, $A_1$-OH, under conditions as previously discussed, yields the conjugate C-6. Next, deprotection of the remaining end group, under conditions familiar to those skilled in the art, yields the carboxylic acid nucleophile, Nu-13, which may be coupled with a second active compound, $A_2$-OH, to ultimately yield the conjugate, C-7, where the active compounds attached at either end are different. Appropriate protected end groups include, but are not limited to, t-butyl esters, t-butoxycarbonyl (BOC), benzyloxycarbonyl (CBZ), and 9-fluorenylmethoxycarbonyl (Fmoc).

As discussed previously, preferred active compounds of the invention are. Appropriate VLA-4 antagonists for use in the processes of this invention can be prepared from readily available starting materials using known procedures and readily available starting materials or, where the starting material is not known or commercially available, such materials can readily be prepared using literature procedures. Detailed processes for preparation of the VLA-4 antagonists have been previously described in U.S. patent application Ser. No. 11/177,748, filed Jul. 8, 2005, and is incorporated herein by reference.

However, it may be necessary to append a short linking group to one of the previous VLA-4 antagonists to introduce an alcohol substituent appropriate for reaction under "Mitsunobu" conditions.

Scheme 7

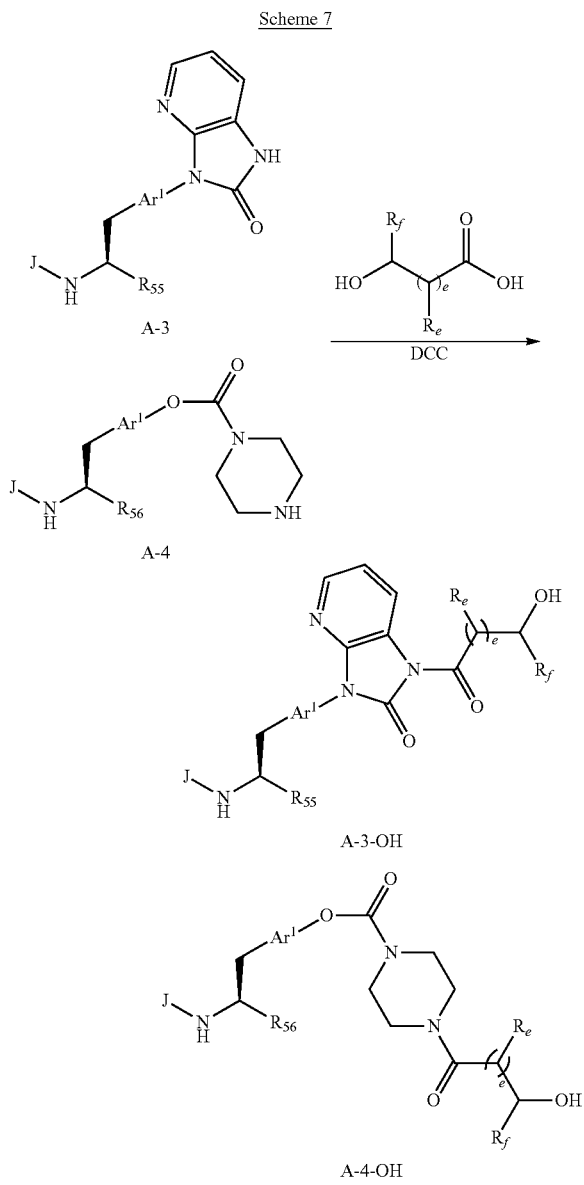

As illustrated in Scheme 7, VLA-4 antagonists prepared according to the methods of the previous reference, represented by A-3 and A-4, which contain 1,3-dihydro-2H-imidazo[4,5-b]pyridin-2-one and piperazine groups respectively, may be coupled to an appropriate linker, terminating in a primary or secondary alcohol for use in the methods of the invention. As an example, an optionally substituted hydroxy acid is reacted with either A-3 or A-4 under dehydrative bond forming conditions, such as treatment with DCC, as discussed previously, to yield the esters A-3-OH and A-4-OH respectively. Appropriate optionally substituted hydroxy acids, include, but are not limited to, glycolic acid, 3-phenylacetic acid, mandelic acid, lactic acid, 2-hydroxyhexanoic acid, 2-hydroxyisocaprolic acid, 2-hydroxy-3-methylbutyric acid, (4-trifluoromethyl)mandelic acid, (4-methoxy)mandelic acid, hexahydromandelic acid, 2-hydroxy-3,3-dimethylbutyric acid, 2-hydroxy-4-phenylbutyric acid, trifluorolactic acid, 4-bromomandelic acid, 2-hydroxyoctanoic acid, 4-fluoromandelic acid, 2-chloromandelic acid, 4-chloromandelic acid, 2-hydroxytetradecanoic acid, 16-hydroxyhexadecanoic acid, 15-hydroxypentadecanoic acid, 12-hydroxydodecanoic acid, 11-hydroxyundecanoic acid, 10-hydroxydecanoic acid, N—BOC-L-serine, N—BOC-L-threonine, N—BOC-L-homoserine, N—BOC-L-homothreonine, trans-4-hydroxy-L-proline, tropic acid, 3-hydroxybutyric acid, and 4-(hydroxymethyl)benzoic acid.

As a final, optional, preparative step, after formation of the conjugate, any protecting groups necessary for the "Mitsunobu" step, or carried along from earlier in the synthesis, may be removed according to methods familiar to those skilled in the art. For example, any carboxylic acids present in the active compound must be protected as, for example, the t-butyl ester, for the "Mitsunobu" coupling to avoid unwanted side products. In a final step, after formation of the polymer conjugate via a "Mitsunobu" reaction, deprotection of t-butyl esters with trifluoroacetic acid or 96% formic acid, yields the free carboxylic acids as part of the conjugate.

Representative conjugates that may be prepared by the process of the instant invention, including pharmaceutically acceptable salts thereof, are set forth in the following table, where m is 0 or 1, q is as defined in formula (I), n depends on the number of groups that H may covalently bond, and n' and n" depend on the molecular weight of the polymer:

TABLE 1

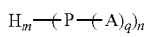

$H_m$—(P—(A)$_q$)$_n$

| Hub/Branched Arm Hub (H) | Polymer (P) |
|---|---|

TABLE 1-continued
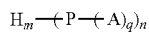
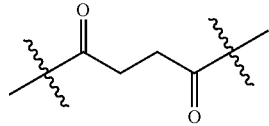 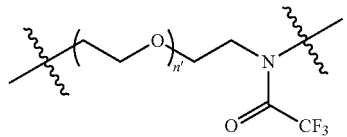
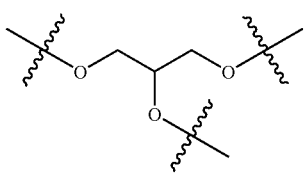 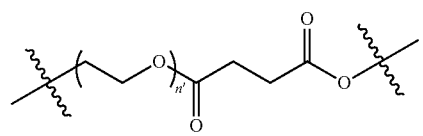
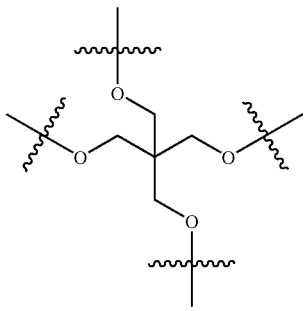 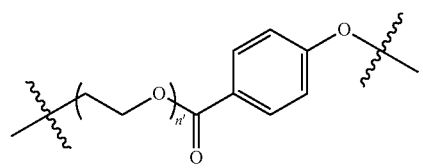
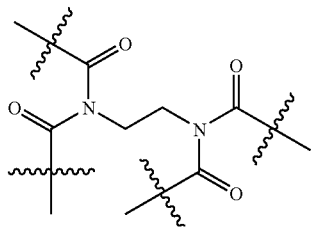 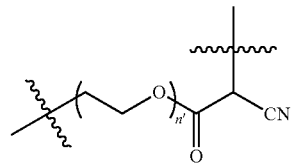
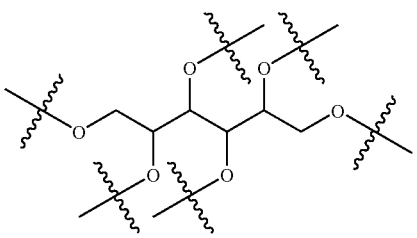 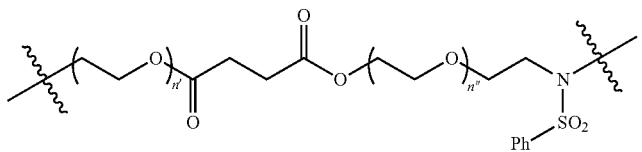

TABLE 1-continued
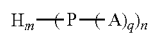
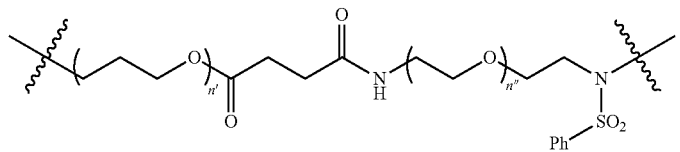
Active Compound (A)
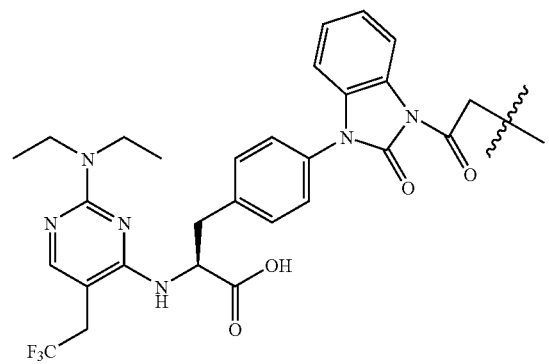
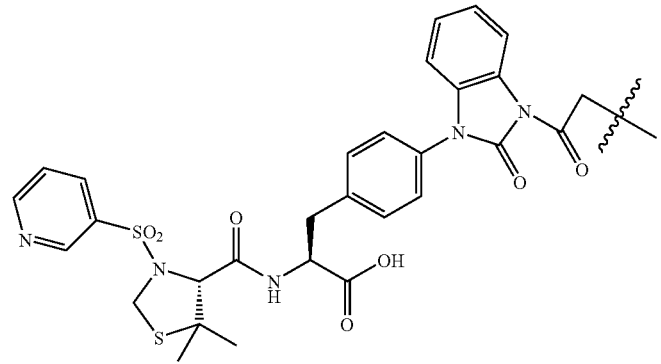
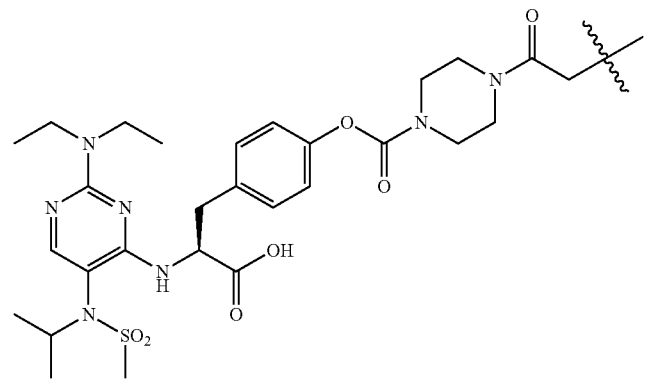

TABLE 1-continued

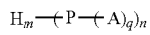

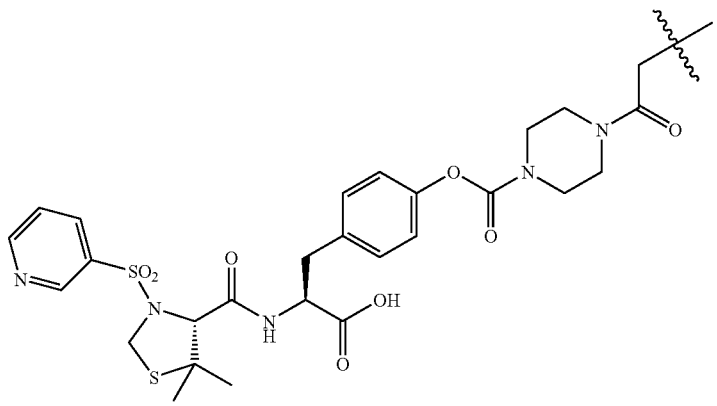

The "Mitsunobu" reaction is preferably carried out in at least one suitable solvent. Examples include halogenated solvents such as dichloromethane, 1,2-dichloroethane, or 1,1,2,2-tetrachloroethane, aromatic solvents such as benzene or toluene, or ether solvents such as diethyl ether, bis(2-methoxyethyl)ether, bis(2-ethoxyethyl)ether, 1,2-dimethoxyethane, 1,2-bis(2-methoxyethoxy)ethane, dioxane, tetrahydropyran, or tetrahydrofuran. Most preferably, a chlorinated solvent or an ether solvent is employed. In a most preferred embodiment, the solvent is dichloromethane or tetrahydrofuran.

Reaction temperature is typically in the range of about −100 to 100° C., preferably in the range of about −20 to 50° C. In a more preferred embodiment, reaction temperatures are from between about −10 to 10° C.

The reaction time is in the range of about 5 minutes to about 100 hours, preferably in the range of from between about 30 minutes to about 50 hours. More preferably, the reaction proceeds to completion of from between about 45 minutes to about 10 hours.

As mentioned above, examples of trivalentphosphines include triphenylphosphine, trimethylphosphine, triethylphosphine, tri(n-propyl)phosphine, triisopropylphosphine, tri(n-butyl)phosphine, methyl(diphenyl)phosphine, dimethyl(phenyl)phosphine, 1,2-bis-(diphenylphosphino)ethane, 1,3-bis-(diphenylphosphino)propane, 1,4-bis-(diphenylphosphino)butane, 1,5-bis-(diphenylphosphino)pentane, 1,6-bis-(diphenylphosphino)hexane, (p-dimethylaminophenyl)diphenylphosphine, diphenyl(2-pyridyl)phosphine, tris(p-dimethylaminophenyl)phosphine, t-butyl 3-(diphenylphosphino)propanoate, 2-(trimethylsilyl)ethyl 4-(diphenylphosphino)benzoate, 1-(diphenylphosphino)-4-(1H,1H,2H,2H-perfluorodecyl)benzene, di(4-(1H,1H,2H,2H-perfluorooctyl)phenyl)phosphinobenzene, a polymer bound phosphines, and water soluble phosphines. A preferred trivalentphosphine is triphenylphosphine.

Examples of azo compounds are dimethyl azodicarboxylate, diethyl azocarboxylate, diisopropyl azodicarboxylate, di-tert-butyl azodicarboxylate, dibenzyl azodicarboxylate, bis(2,2,2-trichloroethyl)azodicarboxylate, diphenyl azodicarboxylate, 4-methyl-3H-1,2,4-triazole-3,5(4H)-dione, N,N,N',N'-tetramethyl azodicarboxamide, 4,7-dimethyl-3,5,7-hexahydro-1,2,4,7-tetrazocin-3,8-dione, 1,1'-(azodicarbonyl)bis(piperidine), 1,1'-(azodicarbonyl)bis(4-methylpiperazine), 4,4'-(azodicarbonyl)bis(morpholine), N,N'-bis(2-(t-butoxy)-2-oxoethyl)azodicarboxamide, bis(5-norbornen-2-ylmethyl)azodicarboxylate, bis(1H, 1H, 2H, 2H-perfluorodecyl)azodicarboxylate, bis(1H, 1H, 2H, 2H-perfluorooctyl)azodicarboxylate, bis(1H, 1H, 2H, 2H, 3H, 3H-perfluorononyl)azodicarboxylate, and any of the previously listed azodicarbonyl compounds on a polymer support.

Polymers suitable for conjugation to a compound of formula (II) include, but are not limited to, linear, branched, brush (or comb) polymers prepared from monomers including, N-vinylpyrrolidone, acrylamide, N,N-dimethylacrylamide, vinyl acetate, dextran, L-glutamic acid, L-aspartic acid, L-lysine, L-threonine, L-tyrosine, D-glutamic acid, D-aspartic acid, D-lysine, D-threonine, D-tyrosine, styrene, maleic anhydride, N-(2-hydroxypropyl)methacrylamide, N-(2-hydroxyethyl)methacryalte, N-(2-hydroxyethyl)methacrylamide, ethylene glycol, ethylene oxide, propylene glycol, propylene oxide, tetrahydrofuran, butylene glycol, tetrahydropyran, ethyl vinyl ether, and copolymers of the previous, including random, alternating, block, multi-block linear copolymers, and star polymers. The polymers may be isotactic, syndiotactic, or atactic as appropriate. Methods for synthesis of biopolymers and for conjugating them to biological materials are well known in the art (see, for example, published U.S. Patent Application 20040043030; U.S. Pat. No. 5,177,059; U.S. Pat. No. 6,716,821; U.S. Pat. No. 5,824,701; U.S. Pat. No. 6,664,331; U.S. Pat. No. 5,880,131; Kameda, Y. et al., Biomaterials 25: 3259-3266, 2004; Thanou, M. et al, Current Opinion in Investigational Drugs 4(6): 701-709, 2003; Veronese, F. M., et al., Il Farmaco 54: 497-516, 1999, all of which are incorporated herein in their entireties).

In addition, dendritic polymers may be used for preparation of conjugates of the invention. Appropriate dendrimers include, but are not limited to, polyamido amine (PAMAM) (Gunatillake et al., Macromolecules, 1988, 21, 1556; U.S. Pat. No. 4,507,466), polyethyleneimine (U.S. Pat. No. 4,631,337), polypropyleneimine (U.S. Pat. No. 5,530,092), and Fréchet-type dendrimers (U.S. Pat. No. 5,041,516; Hawker et al., J. Am. Chem. Soc., 1991, 113, 4583) terminated with amines, alcohols, or carboxylic acid surface groups. A recent review on dendrimer synthesis is Tomalia et al., J. Polym. Sci., Part A: Polym. Chem., 2002, 40, 2719. A recent review on biomedical applications of dendrimers, including bio-compatibility and toxicity, is Boas et al., Chem. Soc. Rev., 2004, 33, 43-63. Specific examples are included in the following table of commercially available polymers.

Commercially available polymers suitable for use in the invention include, but are not limited to:

| Nektar Therapeutics (San Carlos, CA) | |
| --- | --- |
| Cat. No. | Polymer |
| 2M2U0H01 | mPEG-NH$_2$, M$_w$ ~5 kDa |
| 2M2U0L01 | mPEG-NH$_2$, M$_w$ ~10 kDa |
| 2M2U0P01 | mPEG-NH$_2$, M$_w$ ~20 kDa |
| 2M000B01 | mPEG-OH, M$_w$ ~1 kDa |
| 2M000D01 | mPEG-OH, M$_w$ ~2 kDa |
| 2M000E01 | mPEG-OH, M$_w$ ~3 kDa |
| 2M000H01 | mPEG-OH, M$_w$ ~5 kDa |
| 2M000L01 | mPEG-OH, M$_w$ ~10 kDa |
| 2M000M01 | mPEG-OH, M$_w$ ~12 kDa |
| 2M000P01 | mPEG-OH, M$_w$ ~20 kDa |
| 00000P02 | PEG-diol, M$_w$ ~20 kDa |
| 0J000L03 | 3-arm PEG-triol, M$_w$ ~10 kDa, glycerol core |
| 0J000N03 | 3-arm PEG-triol, M$_w$ ~15 kDa, glycerol core |
| 0J000P03 | 3-arm PEG-triol, M$_w$ ~20 kDa, glycerol core |
| 0J000D04 | 4-arm PEG-tetrol, M$_w$ ~2 kDa, pentaerythritol core |
| 0J000L04 | 4-arm PEG-tetrol, M$_w$ ~10 kDa, pentaerythritol core |
| 0J000N04 | 4-arm PEG-tetrol, M$_w$ ~15 kDa, pentaerythritol core |
| 0J000P04 | 4-arm PEG-tetrol, M$_w$ ~20 kDa, pentaerythritol core |
| 0J000D08 | 8-arm PEG-octol, M$_w$ ~2 kDa, hexaglycerine core |
| 0J000L08 | 8-arm PEG-octol, M$_w$ ~10 kDa, hexaglycerine core |
| 0J000N08 | 8-arm PEG-octol, M$_w$ ~15 kDa, hexaglycerine core |
| 0J000P08 | 8-arm PEG-octol, M$_w$ ~20 kDa, hexaglycerine core |
| 0J000T08 | 8-arm PEG-octol, M$_w$ ~40 kDa, hexaglycerine core |

| NOF Corporation (Tokyo, Japan) | |
| --- | --- |
| Product Name (SUNBRIGHT) | Polymer |
| MEH-20H | mPEG-OH, M$_w$ ~2 kDa |
| MEH-50H | mPEG-OH, M$_w$ ~5 kDa |
| MEH-12T | mPEG-OH, M$_w$ ~12 kDa |
| MEH-20T | mPEG-OH, M$_w$ ~20 kDa |
| DKT-34H | PEG-diol, M$_w$ ~3.4 kDa |
| DKT-10T | PEG-diol, M$_w$ ~10 kDa |
| DKT-20T | PEG-diol, M$_w$ ~20 kDa |
| PTE-10000 | 4-arm PEG-tetrol, M$_w$ ~10 kDa, pentaerythritol core |
| PTE-20000 | 4-arm PEG-tetrol, M$_w$ ~20 kDa, pentaerythritol core |
| HGEO-10000 | 8-arm PEG-octol, M$_w$ ~10 kDa, hexaglycerine core |
| HGEO-20000 | 8-arm PEG-octol, M$_w$ ~20 kDa, hexaglycerine core |
| HGEO-40000 | 8-arm PEG-octol, M$_w$ ~40 kDa, hexaglycerine core |
| MEPA-20H | mPEG-NH$_2$, M$_w$ ~2 kDa |
| MEPA-50H | mPEG-NH$_2$, M$_w$ ~5 kDa |
| MEPA-12T | mPEG-NH$_2$, M$_w$ ~12 kDa |
| MEPA-20T | mPEG-NH$_2$, M$_w$ ~20 kDa |
| MEPA-30T | mPEG-NH$_2$, M$_w$ ~30 kDa |
| DE-034PA | PEG-di(CH$_2$CH$_2$NH$_2$), M$_w$ ~3.4 kDa |
| DE-050PA | PEG-di(CH$_2$CH$_2$NH$_2$), M$_w$ ~5 kDa |
| DE-100PA | PEG-di(CH$_2$CH$_2$NH$_2$), M$_w$ ~10 kDa |
| DE-200PA | PEG-di(CH$_2$CH$_2$NH$_2$), M$_w$ ~20 kDa |
| DE-300PA | PEG-di(CH$_2$CH$_2$NH$_2$), M$_w$ ~30 kDa |
| PTE-100PA | 4-arm PEG-tetra(CH$_2$CH$_2$NH$_2$), M$_w$ ~10 kDa, pentaerythritol core |
| PTE-200PA | 4-arm PEG-tetra(CH$_2$CH$_2$NH$_2$), M$_w$ ~20 kDa, pentaerythritol core |

| SunBio (S. Korea) | |
| --- | --- |
| Cat. No. | Polymer |
| P1AM-2 | mPEG-NH$_2$, M$_w$ ~2 kDa |
| P1AM-5 | mPEG-NH$_2$, M$_w$ ~5 kDa |
| P1AM-10 | mPEG-NH$_2$, M$_w$ ~10 kDa |
| P1AM-12 | mPEG-NH$_2$, M$_w$ ~12 kDa |
| P1AM-20 | mPEG-NH$_2$, M$_w$ ~20 kDa |
| P1AM-30 | mPEG-NH$_2$, M$_w$ ~30 kDa |
| P2AM-2 | PEG-diamine, M$_w$ ~2 kDa |
| P2AM-3 | PEG-diamine, M$_w$ ~3.4 kDa |
| P2AM-6 | PEG-diamine, M$_w$ ~6 kDa |
| P2AM-8 | PEG-diamine, M$_w$ ~8 kDa |
| P2AM-10 | PEG-diamine, M$_w$ ~10 kDa |
| P4OH-10 | 4-arm PEG-tetrol, M$_w$ ~10 kDa, pentaerythritol core |
| P4OH-13 | 4-arm PEG-tetrol, M$_w$ ~13 kDa, pentaerythritol core |
| P4OH-15 | 4-arm PEG-tetrol, M$_w$ ~15 kDa, pentaerythritol core |
| P4OH-17 | 4-arm PEG-tetrol, M$_w$ ~17 kDa, pentaerythritol core |
| P4OH-20 | 4-arm PEG-tetrol, M$_w$ ~20 kDa, pentaerythritol core |
| P4AM-10 | 4-arm PEG-tetraamine, M$_w$ ~10 kDa, pentaerythritol core |
| P4AM-13 | 4-arm PEG-tetraamine, M$_w$ ~13 kDa, pentaerythritol core |
| P4AM-15 | 4-arm PEG-tetraamine, M$_w$ ~15 kDa, pentaerythritol core |
| P4AM-17 | 4-arm PEG-tetraamine, M$_w$ ~17 kDa, pentaerythritol core |
| P4AM-20 | 4-arm PEG-tetraamine, M$_w$ ~20 kDa, pentaerythritol core |
| P1OH-1 | mPEG-OH, M$_w$ ~1 kDa |
| P1OH-2 | mPEG-OH, M$_w$ ~2 kDa |
| P1OH-5 | mPEG-OH, M$_w$ ~5 kDa |
| P1OH-10 | mPEG-OH, M$_w$ ~10 kDa |
| P1OH-20 | mPEG-OH, M$_w$ ~20 kDa |
| P6OH-10 | 6-arm PEG-hexol, M$_w$ ~10 kDa, sorbitol core |
| P6OH-15 | 6-arm PEG-hexol, M$_w$ ~15 kDa, sorbitol core |
| P6OH-20 | 6-arm PEG-hexol, M$_w$ ~20 kDa, sorbitol core |
| P6AM-10 | 6-arm PEG-hexaamine, M$_w$ ~10 kDa, sorbitol core |
| P6AM-15 | 6-arm PEG-hexaamine, M$_w$ ~15 kDa, sorbitol core |
| P6AM-20 | 6-arm PEG-hexaamine, M$_w$ ~20 kDa, sorbitol core |

| Polysciences (Warrington, PA) | |
| --- | --- |
| Cat. No. | Polymer |
| | Poly(acrylic acid), M$_w$ ~50 kDa |
| | Poly(1-glycerol methacrylate) |
| | Poly(acrylamide-co-acrylic acid) |
| | Poly(ethylene oxide-block-propylene oxide) |
| | Poly(L-lysine) hydrobromide |
| | Poly(styrenesulfonic acid) |
| | Poly(vinyl alcohol) |
| | Poly(vinyl amine) hydrochloride |
| | poly(caprolactone) diol |

| Cat. No. | Polymer |
|---|---|
| | Sigma-Aldrich (Milwaukee, WI), includes Dendritech products (Midland, MI) |
| 94704 | O,O'-bis(2-carboxyethyl)dodecaethylene glycol |
| 479136 | Poly(allyl amine) |
| 444464 | Poly(antholesulfonic acid, sodium salt) |
| 200387 | Poly(caprolactone) triol 1,1,1-tris(hydroxymethyl)propane core |
| 460818 | Poly(di(ethylene glycol) phthalate) diol |
| 458406 | Poly(di(ethylene glycol)/trimethylolpropane-alt-adipic acid), polyol |
| 452572 | PEG-bis(3-aminopropyl) terminated |
| 406996 | PEG-bis(carboxymethyl) ether, $M_n$ ~250 Da |
| 407038 | PEG-bis(carboxymethyl) ether, $M_n$ ~600 Da |
| 435406 | PEG-block-PPG-block-PEG diol $M_n$ ~1,100 Da |
| 435414 | PEG-block-PPG-block-PEG diol $M_n$ ~1,900 Da |
| 435422 | PEG-block-PPG-block-PEG diol $M_n$ ~2,000 Da |
| 435430 | PEG-block-PPG-block-PEG diol $M_n$ ~2,800 Da |
| 435449 | PEG-block-PPG-block-PEG diol $M_n$ ~2,900 Da |
| 435457 | PEG-block-PPG-block-PEG diol $M_n$ ~4,400 Da |
| 435465 | PEG-block-PPG-block-PEG diol $M_n$ ~5,800 Da |
| 412325 | PEG-block-PPG-block-PEG diol $M_n$ ~8,400 Da |
| 542342 | PEG-block-PPG-block-PEG diol $M_n$ ~14,600 Da |
| 438197 | PEG-ran-PPG diol $M_n$ ~2,500 Da |
| 438200 | PEG-ran-PPG diol $M_n$ ~12,000 Da |
| 438162 | PEG-ran-PPG monobutyl ether $M_n$ ~970 Da |
| 438170 | PEG-ran-PPG monobutyl ether $M_n$ ~1,700 Da |
| 438189 | PEG-ran-PPG monobutyl ether $M_n$ ~3,900 Da |
| 309524 | PEG-tetrahydrofurfuryl ether |
| 182133 | Poly(2-hydroxyethyl methacrylate) |
| 14501 | Polyoxyethylene bis(amine) $M_w$ ~2,000 Da |
| 14509 | Polyoxyethylene bis(amine) $M_w$ ~20,000 Da |
| 202304 | PPG diol $M_n$ ~425 Da |
| 202312 | PPG diol $M_n$ ~725 Da |
| 202320 | PPG diol $M_n$ ~1,000 Da |
| 202339 | PPG diol $M_n$ ~2,000 Da |
| 202347 | PPG diol $M_n$ ~2,700 Da |
| 202355 | PPG diol $M_n$ ~3,500 Da |
| 406651 | PPG-bis(2-aminopropyl) terminated $M_n$ ~230 Da |
| 406678 | PPG-bis(2-aminopropyl) terminated $M_n$ ~400 Da |
| 406686 | PPG-bis(2-aminopropyl) terminated $M_n$ ~2,000 Da |
| 406694 | PPG-bis(2-aminopropyl) terminated $M_n$ ~4,000 Da |
| 435473 | PPG-block-PEG-block-PPG diol $M_n$ ~2,000 Da |
| 435481 | PPG-block-PEG-block-PPG diol $M_n$ ~2,700 Da |
| 435503 | PPG-block-PEG-block-PPG diol $M_n$ ~3,300 Da |
| 406643 | PPG-block-PEG-block-PPG bis(2-aminopropyl) terminated $M_n$ ~600 Da |
| 406627 | PPG-block-PEG-block-PPG bis(2-aminopropyl) terminated $M_n$ ~900 Da |
| 406635 | PPG-block-PEG-block-PPG bis(2-aminopropyl) terminated $M_n$ ~2,000 Da |
| 345261 | Poly(tetrahydrofuran) $M_n$ ~250 Da |
| 345288 | Poly(tetrahydrofuran) $M_n$ ~650 Da |
| 345296 | Poly(tetrahydrofuran) $M_n$ ~1,000 Da |
| 420999 | Poly(tetrahydrofuran) $M_n$ ~1,400 Da |
| 345326 | Poly(tetrahydrofuran) $M_n$ ~2,000 Da |
| 345334 | Poly(tetrahydrofuran) $M_n$ ~2,900 Da |
| 436577 | Poly(tetrahydrofuran) bis(3-aminopropyl) terminated $M_n$ ~1,100 Da |
| P0171 | Poly(DL-lysine) hydrobromide $M_w$ ~1,000-4,000 Da |
| P9011 | Poly(DL-lysine) hydrobromide $M_w$ ~30,000-70,000 Da |
| P8954 | Poly(L-lysine) hydrobromide $M_w$ ~500-2,000 Da |
| P0879 | Poly(L-lysine) hydrobromide $M_w$ ~1,000-4,000 Da |
| P6516 | Poly(L-lysine) hydrobromide $M_w$ ~4,000-15,000 Da |
| P7890 | Poly(L-lysine) hydrobromide $M_w$ ~15,000-30,000 Da |
| P2636 | Poly(L-lysine) hydrobromide $M_w$ ~30,000-70,000 Da |
| P0296 | Poly(D-lysine) hydrobromide $M_w$ ~1,000-4,000 Da |
| P6403 | Poly(D-lysine) hydrobromide $M_w$ ~4,000-15,000 Da |
| P4408 | Poly(D-lysine) hydrobromide $M_w$ ~15,000-30,000 Da |
| P7886 | Poly(D-lysine) hydrobromide $M_w$ ~30,000-70,000 Da |
| P1800 | Poly(L-tyrosine) $M_w$ ~10,000-40,000 Da |
| P5887 | Poly(L-serine) $M_w$ ~5,000-10,000 Da |
| P8077 | Poly(L-threonine) $M_w$ ~5,000-15,000 Da |
| 412368 | PAMAM Dendrimer G(0)-$NH_2$, ethylenediamine core (surface groups: 4) |
| 412384 | PAMAM Dendrimer G(1)-$NH_2$, ethylenediamine core (surface groups: 8) |
| 412406 | PAMAM Dendrimer G(2)-$NH_2$, ethylenediamine core (surface groups: 16) |
| 412422 | PAMAM Dendrimer G(3)-$NH_2$, ethylenediamine core (surface groups: 32) |
| 412449 | PAMAM Dendrimer G(4)-$NH_2$, ethylenediamine core (surface groups: 64) |
| 477834 | PAMAM Dendrimer G(2)-OH, ethylenediamine core (surface groups: 16) |
| 477842 | PAMAM Dendrimer G(3)-OH, ethylenediamine core (surface groups: 32) |
| 477850 | PAMAM Dendrimer G(4)-OH, ethylenediamine core (surface groups: 64) |
| 460699 | DAB-AM-4, polypropyleneimine tetraamine dendrimer (surface groups: 4) |
| 460729 | DAB-AM-8, polypropyleneimine octaamine dendrimer (surface groups: 8) |
| 469076 | DAB-AM-16, polypropyleneimine hexadecaamine dendrimer (surface groups: 16) |
| 469084 | DAB-AM-32, polypropyleneimine dotriacontaamine dendrimer (surface groups: 32) |
| 469092 | DAB-AM-64, polypropyleneimine tetrahexacontaamine dendrimer (surface groups: 64) |
| 597694 | PAMAM-tris(hydroxymethyl)amidomethane dendrimer, Generation 2, ethylenediamine core (surface groups: 48) |
| 597589 | PAMAM-tris(hydroxymethyl)amidomethane dendrimer, Generation 3, ethylenediamine core (surface groups: 96) |
| 592307 | PAMAM-succinamic acid dendrimer, ethylenediamine core, Generation 2 (surface groups: 16) |
| 592196 | PAMAM-succinamic acid dendrimer, ethylenediamine core, Generation 3 (surface groups: 32) |
| 598127 | PAMAM-succinamic acid dendrimer, ethylenediamine core, Generation 4 (surface groups: 64) |
| 595764 | PAMAM Dendrimer G(0)-$NH_2$, 1,4-diaminobutane core (surface groups: 4) |
| 595861 | PAMAM Dendrimer G(1)-$NH_2$, 1,4-diaminobutane core (surface groups: 8) |
| 595985 | PAMAM Dendrimer G(2)-$NH_2$, 1,4-diaminobutane core (surface groups: 16) |
| 596094 | PAMAM Dendrimer G(3)-$NH_2$, 1,4-diaminobutane core (surface groups: 32) |
| 596191 | PAMAM Dendrimer G(4)-$NH_2$, 1,4-diaminobutane core (surface groups: 64) |
| 635189 | PAMAM Dendrimer G(2)-OH, 1,4-diaminobutane core (surface groups: 16) |
| 635197 | PAMAM Dendrimer G(3)-OH, 1,4-diaminobutane core (surface groups: 32) |
| 635200 | PAMAM Dendrimer G(4)-OH, 1,4-diaminobutane e core (surface groups: 64) |
| 635340 | PAMAM-tris(hydroxymethyl)amidomethane dendrimer, Generation 2, 1,4-diaminobutane core (surface groups: 48) |
| 635359 | PAMAM-tris(hydroxymethyl)amidomethane dendrimer, Generation 3, 1,4-diaminobutane core (surface groups: 96) |
| 635855 | PAMAM-succinamic acid dendrimer, 1,4-diaminobutane core, Generation 2 (surface groups: 16) |
| 635863 | PAMAM-succinamic acid dendrimer, 1,4-diaminobutane core, Generation 3 (surface groups: 32) |
| 635871 | PAMAM-succinamic acid dendrimer, 1,4-diaminobutane core, Generation 4 (surface groups: 64) |
| 596523 | PAMAM Dendrimer G(0)-$NH_2$, 1,6-diaminohexane core (surface groups: 4) |
| 596639 | PAMAM Dendrimer G(1)-$NH_2$, 1,6-diaminohexane core (surface groups: 8) |
| 596752 | PAMAM Dendrimer G(2)-$NH_2$, 1,6-diaminohexane core (surface groups: 16) |
| 596868 | PAMAM Dendrimer G(3)-$NH_2$, 1,6-diaminohexane core (surface groups: 32) |
| 596965 | PAMAM Dendrimer G(4)-$NH_2$, 1,6-diaminohexane core (surface groups: 64) |
| 635235 | PAMAM Dendrimer G(2)-OH, 1,6-diaminohexane core (surface groups: 16) |
| 635243 | PAMAM Dendrimer G(3)-OH, 1,6-diaminohexane core (surface groups: 32) |

-continued

| Cat. No. | Polymer |
|---|---|
| 635251 | PAMAM Dendrimer G(4)-OH, 1,6-diaminohexane core (surface groups: 64) |
| 635383 | PAMAM-tris(hydroxymethyl)amidomethane dendrimer, Generation 2, 1,6-diaminohexane core (surface groups: 48) |
| 535375 | PAMAM-tris(hydroxymethyl)amidomethane dendrimer, Generation 3, 1,6-diaminohexane core (surface groups: 96) |
| 636053 | PAMAM-succinamic acid dendrimer, 1,6-diaminohexane core, Generation 2 (surface groups: 16) |
| 636061 | PAMAM-succinamic acid dendrimer, 1,6-diaminohexane core, Generation 3 (surface groups: 32) |
| 636088 | PAMAM-succinamic acid dendrimer, 1,6-diaminohexane core, Generation 4 (surface groups: 64) |
| 597309 | PAMAM Dendrimer G(0)-$NH_2$, 1,12-diaminododecane core (surface groups: 4) |
| 597414 | PAMAM Dendrimer G(1)-$NH_2$, 1,12-diaminododecane core (surface groups: 8) |
| 597635 | PAMAM Dendrimer G(2)-$NH_2$, 1,12-diaminododecane core (surface groups: 16) |
| 597740 | PAMAM Dendrimer G(3)-$NH_2$, 1,12-diaminododecane core (surface groups: 32) |
| 597856 | PAMAM Dendrimer G(4)-$NH_2$, 1,12-diaminododecane core (surface groups: 64) |
| 635294 | PAMAM Dendrimer G(2)-OH, 1,12-diaminododecane core (surface groups: 16) |
| 635308 | PAMAM Dendrimer G(3)-OH, 1,12-diaminododecane core (surface groups: 32) |
| 635316 | PAMAM Dendrimer G(4)-OH, 1,12-diaminododecane core (surface groups: 64) |
| 635456 | PAMAM-tris(hydroxymethyl)amidomethane dendrimer, Generation 2, 1,12-diaminododecane core (surface groups: 48) |
| 635448 | PAMAM-tris(hydroxymethyl)amidomethane dendrimer, Generation 3, 1,12-diaminododecane core (surface groups: 96) |
| 636126 | PAMAM-succinamic acid dendrimer, 1,12-diaminododecane core, Generation 2 (surface groups: 16) |
| 636142 | PAMAM-succinamic acid dendrimer, 1,12-diaminododecane core, Generation 3 (surface groups: 32) |
| 636134 | PAMAM-succinamic acid dendrimer, 1,12-diaminododecane core, Generation 4 (surface groups: 64) |
| Quanta Biodesign, Ltd. (Powell, OH) | |
| 10264 | Amino-$dPEG_2$™ t-butyl ester |
| 10221 | Amino-$dPEG_4$™ t-butyl ester |
| 10271 | Amino-$dPEG_8$™ t-butyl ester |
| 10281 | Amino-$dPEG_{12}$™ t-butyl ester |
| 10311 | Amino-$dPEG_{24}$™ t-butyl ester |
| 10175 | m-$dPEG_4$™ amine |
| 10288 | m-$dPEG_{12}$™ amine |
| 10318 | m-$dPEG_{24}$™ amine |
| 10223 | Hydroxy-$dPEG_4$™ t-butyl ester |
| 10185 | Hydroxy-$dPEG_8$™ t-butyl ester |
| 10252 | m-$dPEG_{11}$™ alcohol |
| 10261 | $dPEG_{12}$™ diol |
| 10225 | Mono-N-t-boc-amido-$dPEG_3$™-amine |
| 10172 | Mono-N-t-boc-amido-$dPEG_{11}$™-amine |
| 10269 | Mono-N-t-CBZ-amido-$dPEG_3$™-amine |
| 10250 | N-t-boc-amido-$dPEG_4$™ alcohol |
| 10171 | N-t-boc-amido-$dPEG_{12}$™ alcohol |
| 10230 | Bis-$dPEG_5$™ acid |
| 10236 | Bis-$dPEG_7$™ acid |
| 10238 | Bis-$dPEG_5$™ half benzyl half acid |
| 10168 | Bis-$dPEG_9$™ half benzyl half acid |
| 10243 | N-Fmoc-amido-$dPEG_2$™ acid |
| 10213 | N-Fmoc-amido-$dPEG_4$™ acid |
| 10273 | N-Fmoc-amido-$dPEG_8$™ acid |
| 10283 | N-Fmoc-amido-$dPEG_{12}$™ acid |
| 10313 | N-Fmoc-amido-$dPEG_{24}$™ acid |
| 10268 | N-CBZ-amido-$dPEG_4$™-acid |
| 10276 | N-CBZ-amido-$dPEG_8$™-acid |
| 10286 | N-CBZ-amido-$dPEG_{12}$™-acid |
| 10316 | N-CBZ-amido-$dPEG_{24}$™-acid |
| 10220 | N-t-boc-amido-$dPEG_4$™-acid |

Pharmaceutical Formulations

When employed as pharmaceuticals, the conjugates of this invention are usually administered in the form of pharmaceutical compositions. These conjugates can be administered by a variety of routes including oral, rectal, transdermal, subcutaneous, intravenous, intramuscular, sublingual, ophthalmic, or inhalation including administration by nasal or oral inhalation. Preferred administration routes include subcutaneous, intravenous, and inhalation. Such compositions are prepared in a manner well known in the pharmaceutical art and comprise at least one conjugate.

The invention also provides pharmaceutical compositions comprising a conjugate according to the invention, e.g., a conjugate of Formula (I), in combination with a separate compound which is an $\alpha_4\beta_7$ inhibitor. Such compositions also comprise a pharmaceutically acceptable carrier or excipient and may be administered as discussed elsewhere herein.

This invention also includes pharmaceutical compositions which contain, as the active ingredient, one or more of the conjugate of formula (I) together with pharmaceutically acceptable carriers. In making the compositions of this invention, the active ingredient is usually mixed with an excipient, diluted by an excipient or enclosed within such a carrier which can be in, sterile injectable solutions, and sterile packaged powders. For subcutaneous administration, a simple carrier may comprise a sterile solution of water, $Na_2HPO_4$, $NaH_2PO_4$, and NaCl, in proportions that provide an isotonic and physiologically acceptable pH, also know as PBS or phosphate-buffered saline. Other options are known to those of skill in the art and include mixed solvent systems that can affect the rate of absorption and total exposure. These options include mixed solvent systems containing glycerin, Polyethylene glycol 400, and cottonseed oil. Also of potential use are ethanol, N,N'-dimethylacetamide, propylene glycol and benzyl alcohol all of which may be used to manipulate permeability enhancement and hypertonicity.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by subcutaneous or intravenous formulation is well known in the pharmaceutical industry. A subcutaneous or intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the invention as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer: alendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

A useful buffer in the invention is sodium citrate/citric acid in the range of 5 to 50 mg per ml of sodium citrate to 1 to 15 mg per ml of citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The conjugate is effective over a wide dosage range and is generally administered in a pharmaceutically effective amount. It, will be understood, however, that the amount of the conjugate actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the invention.

The tablets or pills of the invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner. For inhalation or insufflation administration, it is preferred that the total molecular weight of the conjugate is between about 10,000 Daltons and 70,000 Daltons, more preferably between about 20,000 Daltons and 45,000 Daltons.

Polymer Conjugates

Compounds of this invention as formulated and administered are polymer conjugates. Polymer conjugates are anticipated to provide benefits over non-conjugated polymers, such as improved solubility and in vivo stability.

As such, single polymer molecules may be employed for conjugation with the compounds of the invention, although it is also contemplated that more than one polymer molecule can be attached as well, typically through a carrier. The conjugated compounds of the invention may find utility in both in vivo as well as ex vivo applications. Additionally, it will be recognized that the conjugating polymer may utilize any other groups, moieties, or other conjugated species, as appropriate to the end use application. As an example, it may be advantageous in some applications to functionalize the polymer to render it reactive and enable it to conjugate to a compound of formula II and to enhance various properties or characteristics of the overall conjugated material. Accordingly, the polymer may contain any functionality, repeating groups, linkages, or other constituent structures which do not preclude the efficacy of the conjugated compounds of the invention for its intended purpose.

Illustrative polymers that are usefully employed to achieve these desirable characteristics are described supra, as well as in PCT WO 01/54690 (to Zheng et al.) incorporated by reference herein in its entirety. The polymer may be coupled to the compounds of the invention to form stable bonds that are not significantly cleavable by human enzymes. Generally, for a bond to be not 'significantly' cleavable requires that no more than about 20% of the bonds connecting the polymer and the compounds of the invention to which the polymer is linked, are cleaved within a 24 hour period, as measured by standard techniques in the art including, but not limited to, high pressure liquid chromatography (HPLC).

Generally, the compounds of this invention contain at least about 2 compounds of formula II bound to a polymer. The final amount is a balance between maximizing the extent of the reaction while minimizing non-specific modifications of the product and, at the same time, defining chemistries that will maintain optimum activity, while at the same time optimizing the half-life of the compounds of the invention. Preferably, at least about 50% of the biological activity of the compounds of the invention is retained, and most preferably 100% is retained.

As noted above in the preferred practice of the invention, polyalkylene glycol residues of $C_2$-$C_4$ alkyl polyalkylene glycols, preferably polyethylene glycol (PEG), or poly(oxy) alkylene glycol residues of such glycols are advantageously incorporated in the polymer systems of interest. Thus, the polymer to which the compounds of the invention are attached may be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained.

Examples of polyoxyethylated polyols include, but are not limited to, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

Those of ordinary skill in the art will recognize that the foregoing list is merely illustrative and that all polymer materials having the qualities described herein are contemplated. The polymer need not have any particular molecular weight, but it is preferred that the molecular weight be between about 100 and 100,000, preferably from about 10,000 to 80,000; more preferably from about 20,000 to about 70,000. In particular, sizes of 20,000 or more are most effective at preventing loss of the product due to filtration in the kidneys.

By PEG derivative is meant a polyethylene glycol polymer in which one or both of the hydroxyl end groups has been modified. Examples of suitable modifications include replacing one or both hydroxyl group(s) with alternative functional groups, which may be protected or unprotected, with low molecular weight ligands, or with another macromolecule or polymer. Modification of the hydroxyl end groups of PEG may be achieved by reaction of PEG with compounds comprising complementary reactive functional groups, including functional groups which are able to undergo a reaction with the hydroxyl groups in polyethylene glycol. The PEG derivatives of the compounds of this invention may contain one or more PEG substituents covalently attached thereto by a linking group.

Another preferred formulation employed in the methods of the invention employs transdermal delivery devices ("patches"). Such transdermal patches may be used to provide continuous or discontinuous infusion of the compounds of the invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the invention can be found in Remington's Pharmaceutical Sciences, Mace Publishing Company, Philadelphia, Pa., 17th ed. (1985).

As noted above, the compounds described herein are suitable for use in a variety of drug delivery systems. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Utility

The conjugates of this invention are VLA-4 antagonists. Some also have at least a partial affinity for $\alpha_4\beta_7$ integrins. The conjugates provide enhanced in vivo retention as compared to the non-conjugated compounds. The improved retention of the conjugate within the body results in lower required dosages of the drug, which in turn results in fewer side effects and reduced likelihood of toxicity. In addition, the drug formulation may be administered less frequently to the patient while achieving a similar or improved therapeutic effect.

The conjugates of this invention have improved inhibition, in vivo, of adhesion of leukocytes to endothelial cells mediated by inhibition of $\alpha_4\beta_1$ or $\alpha_4\beta_7$ binding to cellular receptors such as VCAM-1. fibronectin and MadCAM. Preferably, the conjugates of this invention can be used, e.g., by infusion, or by subcutaneous injection or oral administration, for the treatment of diseases mediated by $\alpha_4\beta_1$ or $\alpha_4\beta_7$ or, in general terms, leucocyte adhesion. The conjugates of the invention can be used to treat a variety of inflammatory brain disorders, especially central nervous system disorders in which the endothelium/leukocyte adhesion mechanism results in destruction to otherwise healthy brain tissue. Thus, the conjugates of the invention can be used for, e.g., the treatment of experimental autoimmune encephalomyelitis (EAE), multiple sclerosis (MS), meningitis, and encephalitis.

The conjugates of the invention can also be used to treat disorders and diseases due to tissue damage in other organ systems, i.e., where tissue damage also occurs via an adhesion mechanism resulting in migration or activation of leukocytes. Examples of such diseases in mammalian patients are inflammatory diseases such as asthma, Alzheimer's disease, atherosclerosis, AIDS dementia, diabetes (including acute juvenile onset diabetes), inflammatory bowel disease (including ulcerative colitis and Crohn's disease), rheumatoid arthritis, tissue transplantation rejection, tumor metastasis, stroke, and other cerebral traumas, nephritis, retinitis, atopic dermatitis, psoriasis, myocardial ischemia and acute leukocyte-mediated lung injury such as that which occurs in adult respiratory distress syndrome.

Still other disease conditions which may be treated using conjugates of the invention include erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

The invention also provides methods for treating a disease state caused or exacerbated at least in part by $\alpha_4$ integrin-mediated lekocyte binding in a patient, which methods comprise co-administration of an effective amount of a conjugate of the invention, e.g., a conjugate of Formula (I), and an effective amount of a separate compound which is an $\alpha_4\beta_7$ inhibitor. The co-administration can be carried out simultaneously or sequentially. For example, administration of the conjugate of the invention can precede administration of the $\alpha_4\beta_7$ inhibitor by minutes or hours. Alternatively, the $\alpha_4\beta_7$ inhibitor can be administered prior to the conjugate of the invention.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha_4$ integrins.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, Immunology (3d ed., Raven Press, 1993).

Another indication for the conjugates of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8$^+$ cells, CD4 cells and monocytes are all involved in the rejection of transplant tissues. Conjugates of this invention which bind to alpha-4 integrin are useful, inter alia, to block alloantigen-induced immune responses in the donee thereby preventing such cells from participating in the destruction of the transplanted tissue or organ. See, e.g., Paul et al., Transplant International 9, 420-425 (1996); Georczynski et al., Immunology 87, 573-580 (1996); Georcyznski et al., Transplant. Immunol. 3, 55-61 (1995); Yang et al., Transplantation 60, 71-76 (1995); Anderson et al., APMIS 102, 23-27 (1994).

A related use for conjugates of this invention which bind to VLA-4 is in modulating the immune response involved in "graft versus host" disease (GVHD). See e.g., Schlegel et al., J. Immunol. 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the invention are used, inter alia, to block activation of the donor T-cells thereby interfering with their ability to lyse target cells in the host.

The formulations of the invention are especially useful in the treatment of multiple sclerosis, rheumatoid arthritis and asthma.

A further use of the conjugates of this invention is inhibiting tumor metastasis. Several tumor cells have been reported to express VLA-4 and compounds which bind VLA-4 block adhesion of such cells to endothelial cells. Steinback et al., Urol. Res. 23, 175-83 (1995); Orosz et al., Int. J. Cancer 60, 867-71 (1995); Freedman et al., Leuk. Lymphoma 13, 47-52 (1994); Okahara et al., Cancer Res. 54, 3233-6 (1994).

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

A further use of the conjugates of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

The therapeutic dosage of the conjugates of the invention will vary according to, for example, the particular use for which the treatment is made, the manner of administration of the conjugate, the health and condition of the patient, and the judgment of the prescribing physician. For example, for intravenous administration, the dose will typically be in the range of about 20 µg to about 2000 µg per kilogram body weight, preferably about 20 µg to about 500 µg, more preferably about 100 µg to about 300 µg per kilogram body weight. Suitable dosage ranges for intranasal administration are generally about 0.1 µg to 1 mg per kilogram body weight. Effective doses can be extrapolated from dose-response curves derived from in vitro or animal model test systems.

Conjugates of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, conjugates of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\beta_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., J. Exp. Med. 1998, 188(11) 2187-2191. Compounds that bind $\alpha_e\beta_7$ integrin are also useful for the treatment of systemic lupus erythematosus (see, for example, M. Pang et al., Arthritis Rheum. 1998, 41(8), 1456-1463); Crohn's disease, ulcerative colitis and inflammatory bowel disease (IBD) (see, for example, D. Elewaut et al., Scand J. Gastroenterol 1998, 33(7) 743-748); Sjogren's syndrome (see, for example, U. Kroneld et al., Scand J. Gastroenterol 1998, 27(3), 215-218); and rheumatoid arthritis (see, for example, Scand J. Gastroenterol 1996, 44(3), 293-298). And compounds that bind ($\alpha_6\beta_1$) may be useful in preventing fertilization (see, for example, H. Chen et al., Chem. Biol. 1999, 6, 1-10).

In another aspect of the invention, the conjugates and compositions described herein can be used to inhibit immune cell migration from the bloodstream to the central nervous system in the instance of, for example, multiple sclerosis, or to areas which result in inflammatory-induced destruction of the myelin. Preferably, these reagents inhibit immune cell migration in a manner that inhibits demyelination and that further may promote remyelination. The reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

Inflammatory diseases that are included for treatment by the compositions, conjugates and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination. Additional diseases or conditions contemplated for treatment include meningitis, encephalitis, and spinal cord injuries and conditions generally which induce demyelination as a result of an inflammatory response. The conjugates, compositions and methods disclosed herein are not directed towards diseases and conditions wherein there is, for example, a genetic defect leading to improper myelin formation, e.g., dysmyelination.

The compositions, conjugates and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria, Tay-Sachs disease, Niemann-Pick disease, Gaucher's disease, Hurler's syndrome, Krabbe's disease and other leukodystrophies), neuropathies with abnormal myelination (e.g., Guillain Barré, chronic immune demyelinating polyneuropathy (CIDP), multifocal CIDP, anti-MAG syndrome, GALOP syndrome, anti-sulfatide antibody syndrome, anti-GM2 antibody syndrome, POEMS syndrome, perineuritis, IgM anti-GD1b antibody syndrome), drug related demyelination (e.g., caused by the administration of chloroquine, FK506, perhexyline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis or spinal cord injury) or diseases.

There are various disease models that can be used to study these diseases in vivo. For example, animal models include but are not limited to:

TABLE 2

| Disease Model | Species |
| --- | --- |
| EAE | Mouse, rat, guinea pig |
| Myelin-oligodendrocyte glycoprotein (MOG) induced EAE | Rat |
| TNF-α transgenic model of demyelination | Mouse |

Multiple Sclerosis

The most common demyelinating disease is multiple sclerosis, but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

The cause of MS is yet to be determined. MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high- but not low-frequency trains of impulses or complete conduction block. Positive conduction abnormalities include ectopic impulse generation, spontaneously or following mechanical stress and abnormal "cross-talk" between demyelinated exons.

T cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include: (1) treatment aimed at modification of the disease course, including treatment of acute exacerbation and directed to long-term suppression of the disease; (2) treatment of the symptoms of MS; (3) prevention and treatment of medical complications; and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather then in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-1b, interferon beta-1a, and Copaxone® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

Congenital Metabolic Disorders

Congenital metabolic disorders include phenylketonuria (PKU) and other aminoacidurias, Tay-Sachs disease, Niemann-Pick disease, Gaucher's disease, Hurler's syndrome, Krabbe's disease and other leukodystrophies that impact the developing sheath as described more fully below.

PKU is an inherited error of metabolism caused by a deficiency in the enzyme phenylalanine hydroxylase. Loss of this enzyme results in mental retardation, organ damage, unusual posture and can, in cases of maternal PKU, severely compromise pregnancy. A model for studying PKU has been discovered in mice. Preferably infants identified with PKU are sustained on a phenylalanine free or lowered diet. An aspect of the invention would be to combine such diets with the conjugates and compositions disclosed herein to prevent demyelination and remyelinate cells damaged due to PKU.

Classical Tay-Sachs disease appears in the subject at about age 6 months and will eventually result in the death of the subject by age 5 years. The disease is due to the lack of the enzyme, hexoaminidase A (hex A), which is necessary for degrading certain fatty substances in the brain and nerve cells. The substances in the absence of the enzyme accumulate and lead to the destruction of nerve cells. Another form of hex A enzyme deficiency occurs later in life and is referred to as juvenile, chronic and adult onset forms of hex A deficiency. Symptoms are similar to those that characterize classical Tay-Sachs disease. There is also an adult onset form of the enzyme deficiency. Currently there is no cure or treatment for the disease/deficiency, only the preventative measure of in utero testing of the fetus for the disease. Thus, the conjugates and compositions disclosed herein may be useful in ameliorating or preventing the destruction of nerve cells in such patients.

Niemann-Pick disease falls into three categories: the acute infantile form, Type B is a less common, chronic, non-neurological form, and Type C is a biochemically and genetically distinct form of the disease. In a normal individual, cellular cholesterol is imported into lysosomes for processing, after which it is released. Cells taken from subjects with Niemann-Pick have been shown to be defective in releasing cholesterol from lysosomes. This leads to an excessive build-up of cholesterol inside lysosomes, causing processing errors. NPC1 was found to have known sterol-sensing regions similar to those in other proteins, which suggests it plays a role in regulating cholesterol traffic. No successful therapies have been identified for Types A and C forms of Neumann-Pick. For Type C, patients are recommended to follow a low-cholesterol diet. Thus, the conjugates and compositions disclosed herein may be useful in ameliorating or preventing the destruction of the cells.

Gaucher's disease is an inherited illness caused by a gene mutation. Normally, this gene is responsible for an enzyme called glucocerebrosidase that the body needs to break down the fat, glucocerebroside. In patients with Gaucher's disease, the body is not able to properly produce this enzyme and the fat cannot be broken down. Like Tay-Sachs disease, Gaucher's disease is considerably more common in the descendants of Jewish people from Eastern Europe (Ashkenazi), although individuals from any ethnic group may be affected. Among the Ashkenazi Jewish population, Gaucher's disease is the most common genetic disorder, with an incidence of approximately 1 in 450 persons. In the general public, Gaucher's disease affects approximately 1 in 100,000 persons.

In 1991, enzyme replacement therapy became available as the first effective treatment for Gaucher's disease. The treatment consists of a modified form of the glucocerebrosidase enzyme given intravenously. It is contemplated that the compositions and conjugates disclosed herein can be used alone or more preferably in combination with glycocerebrosidase administration to treat the disease in an afflicted subject.

Hurler's syndrome, also known as mucopolysaccharidosis type I, is a class of overlapping diseases. These genetic diseases share in common the cellular accumulation of mucopolysaccharides in fibroblasts. The diseases are genetically distinguishable. Fibroblast and bone marrow transplantation does not seem to be helpful, thus conjugates and compositions useful in ameliorating disease severity and progression are needed. The conjugates and compositions disclosed herein may be administered to a subject to ameliorate disease progression and/or severity.

Krabbe's disease (also known as Globoid cell leukodystrophy) is an autosomal recessive condition resulting from galactosylceramidase (or galactocerebrosidase) deficiency, a lysosomal enzyme that catabolises a major lipid component of myelin. Incidence in France is an estimated 1:150,000 births. The disease leads to demyelination of the central and peripheral nervous system. Onset generally occurs during the first year of life and the condition is rapidly progressive, but juvenile, adolescent or adult onset forms have also been reported, with a more variable rate of progression. Diagnosis is established from enzyme assay (galactosylceramidase deficiency). There are several natural animal models (mouse, dog, monkey). Krabbe's disease, like all leukodystrophies, has no known cures or effective treatments. One embodiment of the instant invention is to use the compositions and conjugates disclosed herein to treat or ameliorate Krabbe's disease and other leukodystrophies.

Leukodystrophies are a group of genetically determined progressive disorders that affect the brain, spinal cord and peripheral nerves. They include adrenoleukodystrophy (ALD), adrenomyeloneuropathy (AMN), Aicardi-Goutiers syndrome, Alexander's disease, CACH (i.e., childhood ataxia with central nervous system hypomyelination or vanishing white matter disease), CADASIL (i.e., cerebral autosomal dominant arteriopathy with subcortical infarcts and leukoencephalopathy), Canavan disease (spongy degeneration), Cerebrotendinous Xanthomatosis (CTX), Krabbe's disease (discussed above), metachromatic leukodystrophy (MLD), neonatal adrenoleukodystrophy, ovarioleukodystrophy syndrome, Pelizaeus-Merzbacher disease (X-linked spastic paraglegia), Refsum disease, van der Knaap syndrome (vaculating leukodystrophy with subcortical cysts) and Zellweger syndrome. None of the diseases have effective treatments let alone cures. Consequently, means of treating or ameliorating the symptoms of the disease, such as by using the compositions and conjugates disclosed herein, is needed.

Neuropathies with Abnormal Myelination

A variety of chronic immune polyneuropathies exist which result in demyelination in the patient. The age of onset for the conditions varies by condition. Standard treatments for these diseases exist and could be combined with the compositions and conjugates disclosed herein. Alternatively, the compositions and conjugates disclosed can be used alone. Existing standard therapies include the following:

TABLE 3

| Neuropathy | Clinical Features | Treatment |
| --- | --- | --- |
| Chronic Immune Demyelinating Polyneuropathy (CIDP) | Onset between 1-80 years. Characterized by weakness, sensory loss, and nerve hypertrophy. | T-cell immunosuppression with prednisone, cyclosporine A or methotrexate, HIG, plasma exchange |
| Multifocal CIDP | Onset between 28 to 58 years and characterized by asymmetric weakness, sensory loss with a course that is slowly progressive or relapsing-remitting. | T cell immunosuppression with prednisone Human immunoglobulin (HIG) |
| Multifocal Motor Neuropathy (MMN) | Onset ranges from 25 to 70 years, with twice as many men as women. Features include weakness, muscle atrophy, fasciculations, and cramps which are progressive over 1-30 years. | HIG B cell immunosuppression with plasma exchange cyclophosphamide, Rituxan |
| Neuropathy with IgM binding to Myelin-Associated Glycoprotein (MAG) | Onset is usually over age 50 and is characterized by sensory loss (100%), weakness, gain disorder, tremor which is all slowly progressive. | B-cell immunosuppression plasma exchange cyclophosphamide Rituxan α-interferon cladribine or fludarabine prednisone |
| GALOP Syndrome (Gait disorder, Autoantibody, Late-age, Onset, Polyneuropathy) | A gait disorder with polyneuropathy | HIG Plasma exchange cyclophosphamide |
| POEMS Syndrome (Polyneuropathy, Organomegaly, Endocrinopathy, M-Protein and Skin changes) also known as Crow-Fukase Syndrome and Takatsuki disease | Onset occurs between 27 and 80 years with weakness, sensory loss, reduced or absent tendon reflexes, skin disorders and other features. | Osteosclerotic lesions are treated with irradiation. Widespread lesions with chemotherapy (Melphalan and prednisone). |

Drug and Radiation Induced Demyelination

Certain drugs and radiation can induce demyelination in subjects. Drugs that are responsible for demyelination include but are not limited to chloroquine, FK506, perhexyline, procainamide, and zimeldine.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of certain cancers. See for review Belka et al., 2001 *Br. J. Cancer* 85: 1233-9. However, radiation exposure may also be an issue for astronauts (Hopewell, 1994 *Adv. Space Res.* 14: 433-42) as well as in the event of exposure to radioactive substances.

Patients who have received drugs or been exposed accidentally or intentionally to radiation may experience a benefit by administered one of the conjugates or compositions disclosed herein to prevent demyelination or to promote remyelination.

Conditions Involving Demyelination

Additional inherited syndromes/diseases that result in demyelination include Cockayne's syndrome, congenital hypomyelinating, Farber's disease, metachromatic leukodystrophy, Peliszaeus-Merzbacher disease, Refsum, prion related conditions and Salla disease.

Cockayne's syndrome (CS) is a rare inherited disorder in which people are sensitive to sunlight, have short stature and have the appearance of premature aging. In the classical form of Cockayne's syndrome (Type I), the symptoms are progressive and typically become apparent after the age of one year. An early onset or congenital form of Cockayne's syndrome (Type II) is apparent at birth. Interestingly, unlike other DNA repair diseases, Cockayne's syndrome is not linked to cancer. CS is a multi-system disorder that causes both profound growth failure of the soma and brain and progressive cachexia, retinal, cochlear, and neurologic degeneration, with a leukodystrophy and demyelinating neuropathy without an increase in cancer. After exposure to UV (e.g., sunlight), subjects with Cockayne's syndrome can no longer perform transcription-coupled repair. Two genes defective in Cockayne's syndrome, CSA and CSB, have been identified so far. The CSA gene is found on chromosome 5. Both genes code for proteins that interacts with components of the transcriptional machinery and with DNA repair proteins.

To date, no cures or effective treatments for patients with this disease have been identified. Thus, one aspect of the invention is treatment of this disease with the conjugates and compositions disclosed herein.

Congenital hypomyelination has several names including congenital dysmyelinating neuropathy, congenital hypomyelinating polyneuropathy, congenital hypomyelination (Onion Bulb) polyneuropathy, congenital hypomyelination neuropathy, congenital neuropathy caused by hypomyelination, hypomyelination neuropathy and CHN. Hereditary peripheral neuropathies, among the most common genetic disorders in humans, are a complex, clinically and genetically heterogeneous group of disorders that produce progressive deterioration of the peripheral nerves. Congenital hypomyelination is one of a group of disorders. This group includes hereditary neuropathy with liability to pressure palsies, Charcot-Marie-Tooth disease, Dejerine-Sottas syndrome, and congenital hypomyelinating neuropathy. There are no known cures or effective treatments for any of these disorders.

Farber's disease has several names including: Farber lipogranulomatosis, ceremidase deficiency, acid ceramidase deficiency, AC deficiency, N-laurylsphingosine deacylase deficiency, and N-acylsphingosine amidohydrolase. As certain names reveal, the disease occurs due to a deficiency of acid ceramidase (also known as N-acylsphingosine amidohydrolase, ASAH). The lack of the enzyme results in an accumulation of non-sulfonated acid mucopolysaccharide in the neurons and glial cells. Patients with the disease usually die before the age of 2 years.

Metachromatic leukodystrophy (MLD) is a genetic disorder caused by a deficiency of the enzyme arylsulfatase A. It is one of a group of genetic disorders called the leukodystrophies that affect growth of the myelin sheath. There are three forms of MLD: late infantile, juvenile, and adult. In the late infantile form, which is the most common, onset of symptoms begins between ages 6 months and 2 years. The infant is usually normal at birth, but eventually loses previously gained abilities. Symptoms include hypotonia (low muscle tone), speech abnormalities, loss of mental abilities, blindness, rigidity (i.e., uncontrolled muscle tightness), convulsions, impaired swallowing, paralysis, and dementia. Symptoms of the juvenile form begin between ages 4 and 14, and include impaired school performance, mental deterioration, ataxia, seizures, and dementia. In the adult form, symptoms, which begin after age 16, may include impaired concentration, depression, psychiatric disturbances, ataxia, tremor, and dementia. Seizures may occur in the adult form, but are less common than in the other forms. In all three forms mental deterioration is usually the first sign.

Pelizaeus-Merzbacher disease (also known as perinatal sudanophilic leukodystrophy) is an X-linked genetic disorder that causes an abnormality of a proteolipid protein. The abnormality results in an infant's death typically before the age of one year. There are no known treatments or cures for the disease.

Refsum disease (also referred to as phytanic acid oxidase deficiency, heredopathia atactica polyneuritiformis or hereditary motor and sensory neuropathy IV, HMSN IV) is caused by mutations in the gene, which encodes phytanoyl-CoA hydroxylase (PAHX or PHYH). The major clinical features are retinitis pigmentosa, chronic polyneuropathy and cerebellar signs. Phytanic acid, an unusual branched chain fatty acid (3,7,11,15-tetramethyl-hexadecanoic acid) accumulates in the tissues and body fluids of patients with the disease and is unable to be metabolised due to the lack of PAHX. Plasmapheresis performed once or twice monthly effectively removes the acid from the body and permits liberalization of dietary restrictions limiting phytanic acid intake.

Prion related conditions include Gerstmann-Straussler disease (GSD), Creutzfeldt-Jakob disease (CJD), familial fatal insomnia and aberrant isoforms of the prion protein can act as infectious agents in these disorders as well as in kuru and scrapie (a disease found in sheep). The term prion derives from "protein infectious agent" (Prusiner, *Science* 216: 136-44, 1982). There is a proteolytic cleavage of the prion related protein (PRP) which results in an amyloidogenic peptide that polymerises into insoluble fibrils.

Salla disease and other types of sialurias are diseases involving problems with sialic acid storage. They are autosomal recessive neurodegenerative disorders that may present as a severe infantile form (i.e., ISSD) or as a slowly progressive adult form that is prevalent in Finland (i.e., Salla disease). The main symptoms are hypotonia, cerebellar ataxia and mental retardation. These conditions and diseases are also contemplated for palliative or ameliorating treatments.

Other conditions that result in demyelination include post-infectious encephalitis (also known as acute disseminated encephalomyelitis, ADEM), meningitis and injuries to the spinal cord. The compositions and conjugates disclosed herein are also contemplated for use in treating these other demyelinating conditions.

The following synthetic and biological examples are offered to illustrate this invention and are not to be construed in any way as limiting the scope of this invention. Unless otherwise stated, all temperatures are in degrees Celsius.

What is claimed is:
1. A process for preparing a conjugate of formula (I),

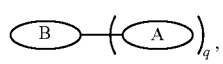
(I)

wherein
q is from 1 to 100;
A, at each occurrence, is independently an active compound of formula (II),

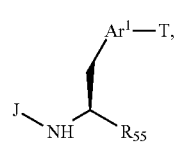
(II)

or a pharmaceutically acceptable salt thereof, wherein
$Ar^1$ is aryl or heteroaryl, wherein
the aryl or heteroaryl is optionally substituted with one or more groups which are each independently —$NO_2$, —CN, -halo, —$(Z^1)_aM_b((Z^2)_cR^Z)$, or -$D_dE_eF$—, wherein,
M is —C(O)—, —C(S)—, —S(O)—, or —S(O)$_2$—, provided when M is —S(O) or —S(O)$_2$, either a or c is zero;
$Z^1$ is —O—, —S—, or —N($R^N$)—, wherein
$R^N$ is —H, —($C_1$-$C_6$)alkyl, —($C_1$-$C_6$)alkenyl, —($C_1$-$C_6$)alkynyl, —($C_1$-$C_6$)haloalkyl, —($C_1$-$C_6$)alkanoyl, —($C_3$-$C_8$)cycloalkyl, -heterocycle, -aryl, -heteroaryl, —($C_3$-$C_8$)cycloalkanoyl, -heterocycloyl, -aroyl, -heteroaroyl, —($C_1$-$C_6$)alkoxycarbonyl, or -aryl($C_1$-$C_6$)alkoxycarbonyl, wherein
the aryl or heteroaryl is optionally substituted with one or more groups which are independently -halo, —$NO_2$, —CN, —($C_1$-$C_6$)alkyl, —($C_1$-$C_6$)haloalkyl, —($C_1$-$C_6$)alkanoyl, or -aroyl;
$Z^2$ is —O—, —S—, or —N($R^N$)—;
a, b and c are independently 0 or 1, provided when b is zero, a is zero, and when b is one, a is 0 or 1;
$R^Z$ is —H, —($C_1$-$C_6$)alkyl, —($C_1$-$C_6$)alkenyl, —($C_1$-$C_6$)alkynyl, —($C_1$-$C_6$)haloalkyl, —($C_3$-$C_8$)cycloalkyl, —($C_1$-$C_6$)alkylaryl, -heterocycle, -aryl, or -heteroaryl;
D is —$CH_2$—, —$OCH_2$—, —$CH_2O$—, —C(O)—, —O(O)$_2$—, —C(O)(NR$^N$)—, —S(O)$_2$—, —C(S)—, or —C(S)$_2$—;
E is —CH($R_e$)—, —CH($R_e$)$CH_2$—, —($C_3$-$C_{16}$) alkyl-, —($C_1$-$C_6$)alkoxy-, —($C_1$-$C_6$)alkenyl-, —($C_1$-$C_6$)alkynyl, —($C_1$-$C_6$)haloalkyl-, —($C_3$-$C_8$)cycloalkyl-, -heterocycle-, -aryl-, or -heteroaryl-, wherein
$R_e$ is —H or —N(R")($R^N$); and
R" is —H or together with $R_f$ form a heterocycloalkyl;
F is a bond, —CH($R_f$)—, or —$CH_2CH(R_f)$—, provided that F is covalently bonded to B, wherein
$R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, -heteroaryl, or together with R" form a heterocycloalkyl, wherein
each aryl or heteroaryl is optionally substituted with one or more groups which are each independently —$NO_2$, —CN, -halo, or —$(Z)_aM_b((Z)_cR^Z)$;
d is 0 or 1; and
e is 0 or 1, provided when E is —($C_1$-$C_8$)alkoxy-, e is 1 to 250;
J is:
a) a group of formula (a),

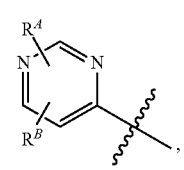
(a)

wherein $R^A$ is $-(Z^1)_a M_b((Z^2)_c R^Z)$; and $R^B$ is $-H$, $-NO_2$, $-(C_1-C_6)$alkyl, $-(C_3-C_8)$cycloalkyl, -aryl, -heteroaryl, $-(C_1-C_6)$haloalkyl, or $-(N(R^{A1}))M_b((Z^2)_c R^Z)$, provided that when b is zero, c is also zero, wherein each aryl or heteroaryl is optionally substituted with one or more groups which are each independently $-CN$, $-NO_2$, -halo, or $-(Z^1)_a M_b((Z^2)_c R^Z)$;

or b) a group of formula (b),

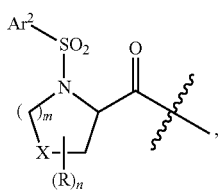

(b)

wherein $Ar^2$ is $Ar^1$;

m is 0, 1, or 2;

n is 0, 1, or 2;

each R is independently $-(Z^1)_a M_b((Z^2)_c R^Z)$ or $-D_d E_e F-$; and

X is $-N(R^N)-$, $-O-$, $-S-$, $-S(O)-$, $-S(O)_2-$, or $-C(R)_2-$;

T is a) a group of formula (c),

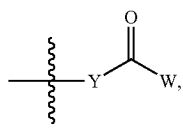

(c)

wherein

Y is $-O-$ or $-N(R^N)-$; and

W is $-L_1-L_2-$, wherein $L_1$ is $NR^2R^3$, wherein $R^2$ and $R^3$ are independently $-H$ or $-(C_1-C_6)$alkyl, or together with the nitrogen atom bound thereto, form a heterocycle containing 0 to 4 additional heteroatoms independently selected from $-O-$, $-S-$, and $-N(R^N)$; and $L_2$ is absent, $R^N$, or $-D_d E_e F-$;

or b) a group of formula (d)

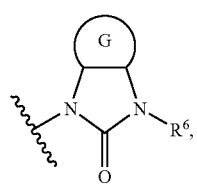

(d)

wherein

G is aryl or a monocyclic heteroaryl containing 1 to 3 nitrogens; and $R^6$ is $R^N$ or $-D_d E_e F-$; and $R^{55}$ is $-M(Z^2 R^Z)$;

and

B is a group of formula Ia, which is a polymer functionalized with nucleophilic active moieties,

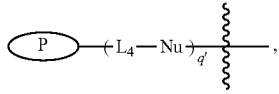

(Ia)

wherein

P is a polymer;

q' is greater than or equal to q, as defined in formula (I);

$L_4$ is $-D_d E_e F'_f-$, wherein

F' is F or $-C(O)-$; and f' is 0 or 1; and

Nu is $-N(SO_2R^4)-$, $-[S(O)_2]N(R^N)-$, -aryl-O—, -aryl-S—, $-N(C(O)CF_3)-$, $-(NC)C(H)C(O)-$, $-(NC)C(H)S(O)_2-$, $-[R^4S(O)_2]C(H)[S(O)_2]-$, $-[R^4S(O)_2]C(H)C(O)-$, or $-C(O)O-$, wherein the aryl is optionally substituted with one or more groups that are each independently $-NO_2$, $-ON$, $-S(O)_2R^5$, $-C(O)OR^5$, or $-C(O)R^5$, wherein $R^5$ is each independently $-H$, $-(C_1-C_6)$alkyl, $-(C_1-C_6)$alkenyl, $-(C_1-C_6)$alkynyl, $-(C_1-C_6)$haloalkyl, $-(C_3-C_8)$cycloalkyl, -heterocycle, -aryl, -heteroaryl, wherein the aryl or heteroaryl is optionally substituted with $-(Z^1)_a M_b((Z^2)_c R^Z)$; and $R^4$ is $-(C_1-C_6)$alkyl, $-(C_1-C_6)$alkenyl, $-(C_1-C_6)$alkynyl, $-(C_1-C_6)$haloalkyl, $-(C_3-C_8)$cycloalkyl, -heterocycle, -heteroaryl, or -aryl, wherein the aryl or heteroaryl is optionally substituted with 1 to 4 groups which are independently $-NO_2$, $-ON$, -halo, or $-(Z^1)_a M_b((Z^2)_c R^Z)$;

provided that when X is $-O-$ or $-N(R^N)-$, then m is two; and provided that when R is covalently bonded to B, n is one and X is not $-O-$, $-S-$, $-S(O)-$, or $-S(O)_2-$;

comprising the steps of:

a) treating, in at least one solvent, at least one active compound of formula (Ib),

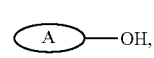

(Ib)

wherein

A is as defined in formula (I); and $-OH$ is covalently bonded to F;

with a trivalentphosphine, an azodicarbonyl compound, and an optional tertiary amine additive; and b) adding a polymeric nucleophile of formula (Ic),

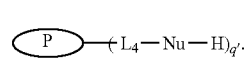

(Ic)

2. A process according to claim 1, wherein
Nu is —N(SO$_2$R$^4$)—, -phenyl-O—, —N(C(O)CF$_3$)—, —(NC)C(H)C(O)—, or —C(O)O—, wherein
R$^4$ is —(C$_1$-C$_6$)alkyl, —(C$_1$-C$_6$)haloalkyl, or -aryl, wherein the aryl is optionally substituted with 1 to 4 groups which are independently —NO$_2$, —CN, -halo, or —(Z$^1$)$_a$M$_b$((Z$^2$)$_c$R$^Z$).

3. A process according to claim 2, wherein
L$_4$ is -D'$_{d'}$E'$_{e'}$F''$_{f'}$—, wherein
D' is —CH$_2$— or —C(O)—;
E' is —CH(R$_{e'}$)—, —(C$_3$-C$_{16}$)alkyl-, or -aryl- wherein R$_{e'}$ is —H or —NH(R$^N$);
F'' is a bond or —CH(R$_{f'}$)— provided that F'' is covalently bonded to B, wherein
R$_{f'}$ is —H, —(C$_1$-C$_6$)alkyl, —(C$_1$-C$_6$)haloalkyl, -aryl, or -heteroaryl, wherein
each aryl or heteroaryl is optionally substituted with one or more groups which are each independently —NO$_2$, —CN, -halo, or —(Z$^1$)$_a$M$_b$((Z$^2$)$_c$R$^Z$);
d' is 0 or 1;
e' is 0 or 1; and
f'' is 0 or 1.

4. A process according to claim 3, wherein A at each occurrence is independently a compound of formula (III), (IV), (V), or (VI),

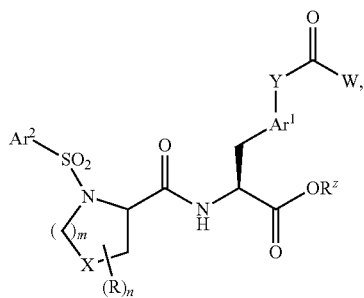
(III)

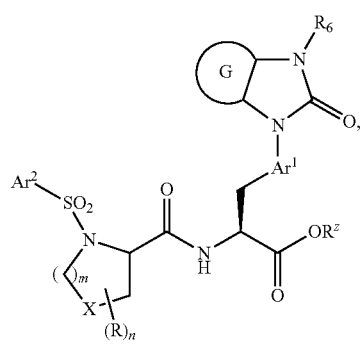
(IV)

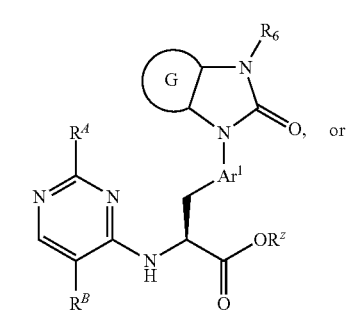
(V)

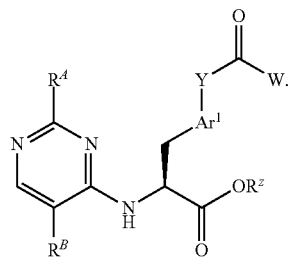
(VI)

5. A process according to claim 4, wherein Ar$^1$ is phenyl.

6. A process according to claim 5, wherein X is —S— or —CH$_2$—; and m is 1.

7. A process according to claim 6, wherein A at each occurrence is a compound of formula (VII),

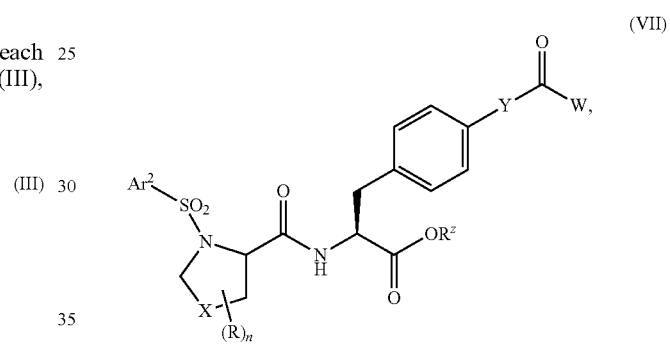
(VII)

wherein
Y is —O—; and
W is -L$_1$-L$_2$-, wherein
L$_1$ is NR$^2$R$^3$, wherein
R$^2$ and R$^3$ together with the nitrogen atom bound thereto, form a heterocycle containing 0 to 4 additional heteroatoms independently selected from —O—, —S—, and —N(R$^N$); and
L$_2$ is -D$_d$E$_e$F—.

8. A process according to claim 7, wherein A at each occurrence is a compound of formula (VIII),

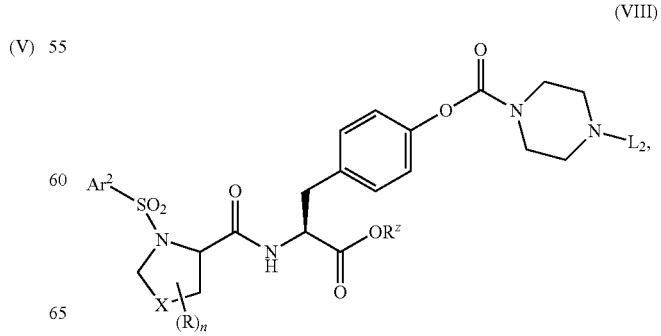
(VIII)

wherein
L₂ is -D_dE_eF—, wherein
  D is —CH₂— or —C(O)—;
  E is —CH(R_e)—, —(C₃-C₁₆)alkyl-, —(C₁-C₆)alkoxy-, —(C₁-C₆)haloalkyl-, —(C₃-C₈)cycloalkyl-, or -aryl-, wherein
    R_e is —H or —NH(R^N);
  F is a bond, —CH(R_f)—, or —CH₂CH(R_f)—, provided that F is covalently bonded to B, wherein
    R_f is —H, —(C₁-C₆)alkyl, —(C₁-C₆)haloalkyl, -aryl, —(C₁-C₆)alkylaryl, —(C₃-C₈)cycloalkyl, -heterocycloalkyl, or -heteroaryl;
  d is 0 or 1; and
  e is 0 or 1.

9. A process according to claim 8, wherein A at each occurrence is a compound of formula (IX),

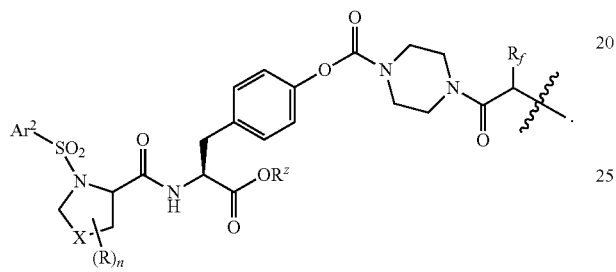

(IX)

10. A process according to claim 9, wherein R^Z is —H or —(C₁-C₆)alkyl.

11. A process according to claim 9, wherein R^Z is —H.

12. A process according to claim 11, wherein X is —CH₂—; and n is 0.

13. A process according to claim 11, wherein A at each occurrence is a compound of formula (X),

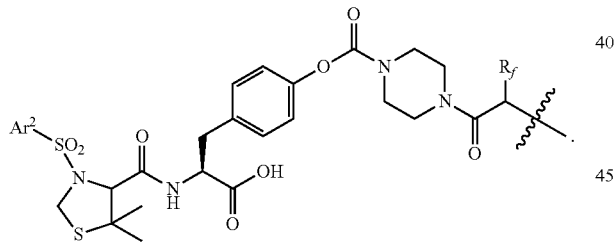

(X)

14. A process according to claim 6, wherein A at each occurrence is a compound of formula (XI),

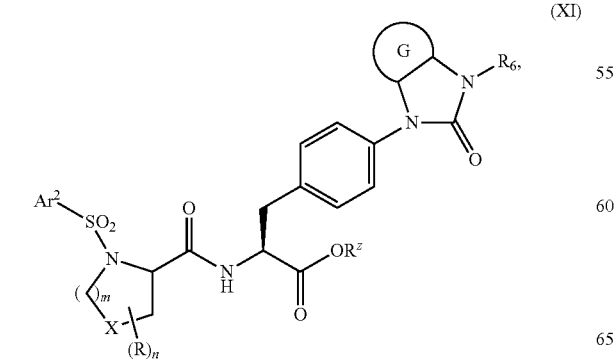

(XI)

wherein
R⁶ is -D_dE_eF—, wherein
  D is —CH₂— or —C(O)—;
  E is —CH(R_e)—, —(C₃-C₁₆)alkyl-, —(C₁-C₆)alkoxy-, —(C₁-C₆)haloalkyl-, —(C₃-C₈)cycloalkyl-, or -aryl-, wherein
    R_e is —H or —NH(R^N);
  F is a bond, —CH(R_f)—, or —CH₂CH(R_f)—, provided that F is covalently bonded to B, wherein
    R_f is —H, —(C₁-C₆)alkyl, —(C₁-C₆)haloalkyl, -aryl, —(C₁-C₆)alkylaryl, —(C₃-C₈)cycloalkyl, -heterocycloalkyl, or -heteroaryl;
  d is 0 or 1; and
  e is 0 or 1.

15. A process according to claim 14, wherein A at each occurrence is a compound of formula (XII),

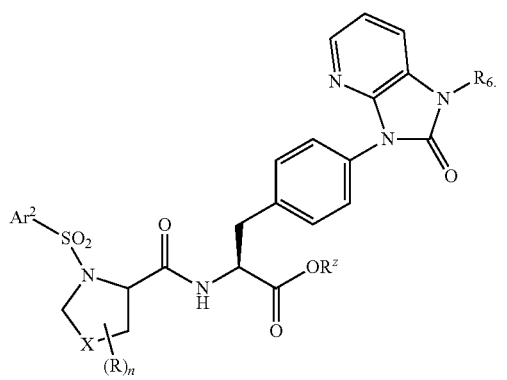

(XII)

16. A process according to claim 15, wherein A at each occurrence is a compound of formula (XIII),

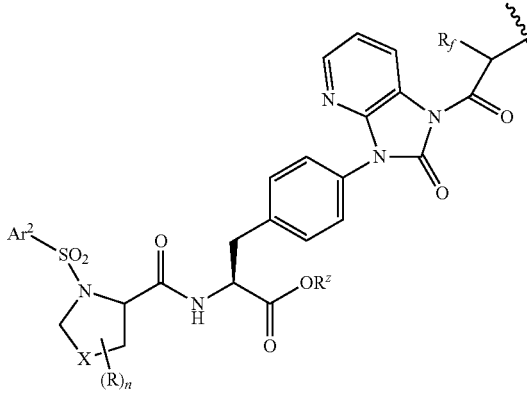

(XIII)

17. A process according to claim 16, wherein
R^Z is —H or —(C₁-C₆)alkyl.

18. A process according to claim 16, wherein R^Z is —H.

19. A process according to claim 18, wherein X is —CH₂—; and n is 0.

20. A process according to claim 18, wherein A at each occurrence is a compound of formula (XIV), (XIV)

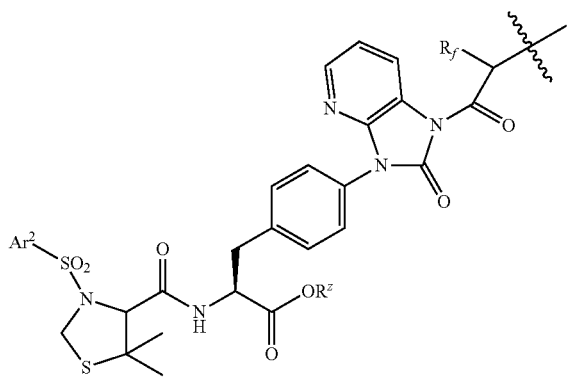

21. A process according to claim 5, wherein A at each occurrence is a compound of formula (XV),

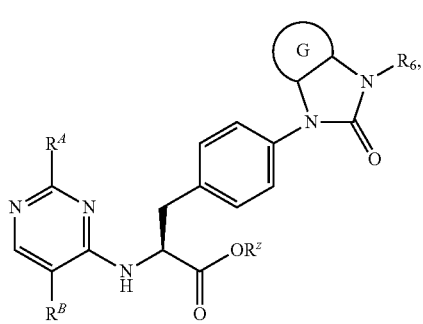
(XV)

wherein
  R⁶ is -D$_d$E$_e$F—, wherein
    D is —CH$_2$— or —C(O)—;
    E is —CH(R$_e$)—, —(C$_3$-C$_{16}$)alkyl-, —(C$_1$-C$_6$)alkoxy-, —(C$_1$-C$_6$)haloalkyl-, —(C$_3$-C$_8$)cycloalkyl-, or -aryl-, wherein
      R$_e$ is —H or —NH(R$^N$);
    F is a bond, —CH(R$_f$)—, or —CH$_2$CH(R$_f$)—, provided that F is covalently bonded to B, wherein
      R$_f$ is —H, —(C$_1$-C$_6$)alkyl, —(C$_1$-C$_6$)haloalkyl, -aryl, —(C$_1$-C$_6$)alkylaryl, —(C$_3$-C$_8$)cycloalkyl, -heterocycloalkyl, or -heteroaryl;
    d is 0 or 1; and
    e is 0 or 1.

22. A process according to claim 21, wherein A at each occurrence is a compound of formula (XVI),

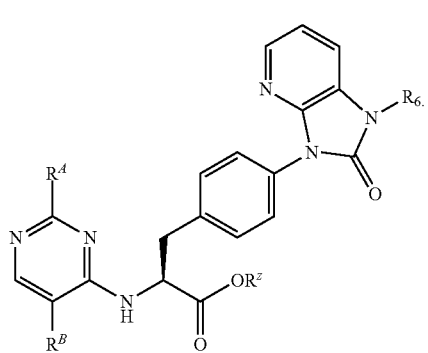
(XVI)

23. A process according to claim 22, wherein A at each occurrence is a compound of formula (XVII),

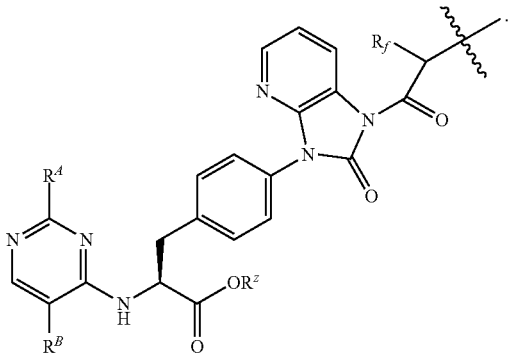
(XVII)

24. A process according to claim 23, wherein R$^Z$ is —H or —(C$_1$-C$_6$)alkyl.

25. A process according to claim 23, wherein R$^Z$ is —H.

26. A process according to claim 5, wherein A at each occurrence is a compound of formula (XVIII),

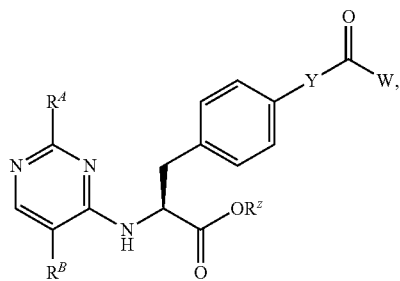
(XVIII)

wherein
  Y is —O—; and
  W is -L$_1$-L$_2$-, wherein
    L$_1$ is NR²R³, wherein
      R² and R³ together with the nitrogen atom bound thereto, form a heterocycle containing 0 to 4 additional heteroatoms independently selected from —O—, —S—, and —N(R$^N$); and
    L$_2$ is -D$_d$E$_e$F—.

27. A process according to claim 26, wherein A at each occurrence is a compound of formula (XIX),

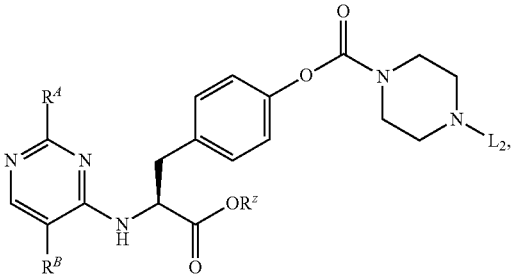
(XIX)

wherein
    $L_2$ is -$D_dE_eF$—, wherein
        D is —$CH_2$— or —C(O)—;
        E is —CH($R_e$)—, —($C_3$-$C_{16}$)alkyl-, —($C_1$-$C_6$)alkoxy-, —($C_1$-$C_6$)haloalkyl-, —($C_3$-$C_8$)cycloalkyl-, or -aryl-, wherein
            $R_e$ is —H or —NH($R^N$);
        F is a bond, —CH($R_f$)—, or —$CH_2$CH($R_f$)—, provided that F is covalently bonded to B, wherein
            $R_f$ is —H, —($C_1$-$C_6$)alkyl, —($C_1$-$C_6$)haloalkyl, -aryl, —($C_1$-$C_6$)alkylaryl, —($C_3$-$C_8$)cycloalkyl, -heterocycloalkyl, or -heteroaryl;
        d is 0 or 1; and
        e is 0 or 1.

28. A process according to claim 27, wherein A at each occurrence is a compound of formula (XX),

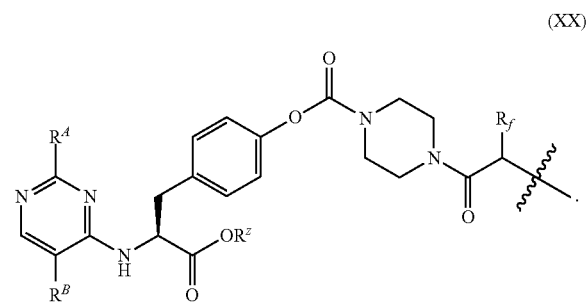

(XX)

29. A process according to claim 28, wherein $R^Z$ is —H or —($C_1$-$C_6$)alkyl.

30. A process according to claim 28, wherein $R^Z$ is —H.

31. A process according to claim 1 wherein the azodicarbonyl compound is dimethyl azodicarboxylate, diethyl azocarboxylate, diisopropyl azodicarboxylate, di-tert-butyl azodicarboxylate, dibenzyl azodicarboxylate, bis(2,2,2-trichloroethyl)azodicarboxylate, diphenyl azodicarboxylate, 4-methyl-3H-1,2,4-triazole-3,5(4H)-dione, N,N,N',N'-tetramethyl azodicarboxamide, 4,7-dimethyl-3,5,7-hexahydro-1,2,4,7-tetrazocin-3,8-dione, 1,1'-(azodicarbonyl)bis(piperidine), 1,1'-(azodicarbonyl)bis(4-methylpiperazine), 4,4'-(azodicarbonyl)bis(morpholine), N,N'-bis(2-(t-butoxy)-2-oxoethyl)azodicarboxamide, bis(5-norbornen-2-ylmethyl) azodicarboxylate, bis(1H,1H,2H,2H-perfluorodecyl) azodicarboxylate, bis(1H,1H,2H,2H-perfluorooctyl) azodicarboxylate, bis(1H,1H,2H,2H,3H,3H-perfluorononyl) azodicarboxylate, or a polymer supported azodicarbonyl compound.

32. A process according to claim 1 wherein the azodicarbonyl compound is diethyl azocarboxylate, diisopropyl azodicarboxylate, di-tert-butyl azodicarboxylate, 4-methyl-3H-1,2,4-triazole-3,5(4H)-dione, N,N,N',N'-tetramethyl azodicarboxamide, or 1,1'-(azodicarbonyl)bis(piperidine).

33. A process according to claim 1, where the optional tertiary amine additive is trimethylamine, triethylamine, tri(n-propyl)amine, triisopropylamine, N-ethyldiisopropylamine, triphenylamine, tri(p-tolyl)amine, tetramethylethylenediamine, N-methylmorpholine, N-methylpiperidine, N,N-dimethylpiperazine, 4-dimethylaminopyridine, N,N-dimethylaniline, N,N-diethylaniline, N,N-diisopropylaniline, N-methylpyrrolidine, pyridine, pyrazine, pyrimidine, 1-methylimidazole, 1,8-diazabicyclo[5.4.0]undec-7-ene, 1,5-diazabicyclo[4.3.0]non-5-ene, 1,4-diazabicyclo[2.2.2]octane, or 6-(dibutylamino)-1,8-diazabicyclo[5.4.0]undec-7-ene.

34. A process according to claim 1 wherein the trivalent-phosphine is triphenylphosphine, trimethylphosphine, triethylphosphine, tri(n-propyl)phosphine, triisopropylphosphine, tri(n-butyl)phosphine, methyl(diphenyl)phosphine, dimethyl(phenyl)phosphine, 1,2-bis-(diphenylphosphino)ethane, 1,3-bis-(diphenylphosphino)propane, 1,4-bis-(diphenylphosphino)butane, 1,5-bis-(diphenylphosphino)pentane, 1,6-bis-(diphenylphosphino)hexane, (p-dimethylaminophenyl)diphenylphosphine, diphenyl(2-pyridyl)phosphine, tris(p-dimethylaminophenyl)phosphine, t-butyl 3-(diphenylphosphino)propanoate, 2-(trimethylsilyl)ethyl 4-(diphenylphosphino)benzoate, 1-(diphenylphosphino)-4-(1H,1H,2H,2H-perfluorodecyl)benzene, di(4-(1H,1H,2H,2H-perfluorooctyl)phenyl)phosphinobenzene, or any of the previously listed on a polymer support.

35. A process according to claim 1 wherein the solvent is an aromatic solvent, a chlorinated solvent, or an ether solvent.

36. A process according to claim 1 wherein the azodicarbonyl compound is dimethyl azodicarboxylate, diethyl azocarboxylate, diisopropyl azodicarboxylate, di-tert-butyl azodicarboxylate, dibenzyl azodicarboxylate, bis(2,2,2-trichloroethyl)azodicarboxylate, diphenyl azodicarboxylate, 4-methyl-3H-1,2,4-triazole-3,5(4H)-dione, N,N,N',N'-tetramethyl azodicarboxamide, 4,7-dimethyl-3,5,7-hexahydro-1,2,4,7-tetrazocin-3,8-dione, 1,1'-(azodicarbonyl)bis(piperidine), 1,1'-(azodicarbonyl)bis(4-methylpiperazine), 4,4'-(azodicarbonyl)bis(morpholine), or N,N'-bis(2-(t-butoxy)-2-oxoethyl)azodicarboxamide.

37. A process according to claim 34, wherein the trivalent-phosphine is triphenylphosphine or tri(n-butyl)phosphine.

38. A process according to claim 1, wherein q is 1 to 64.

39. A process for the preparation of conjugates of active compounds comprising:
    (a) treating a primary or secondary alcohol substituent of at least one active compound under "Mitsunobu" or related conditions; and
    (b) treating the product of (a) with a polymer containing nucleophilic substituents active under "Mitsunobu" or related conditions,
wherein the polymer is selected from the group consisting of:

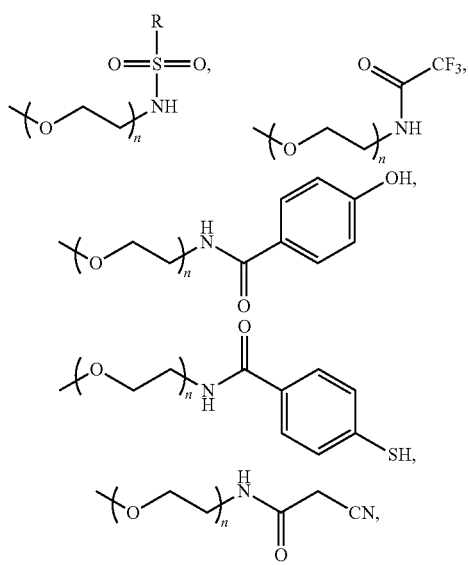

-continued

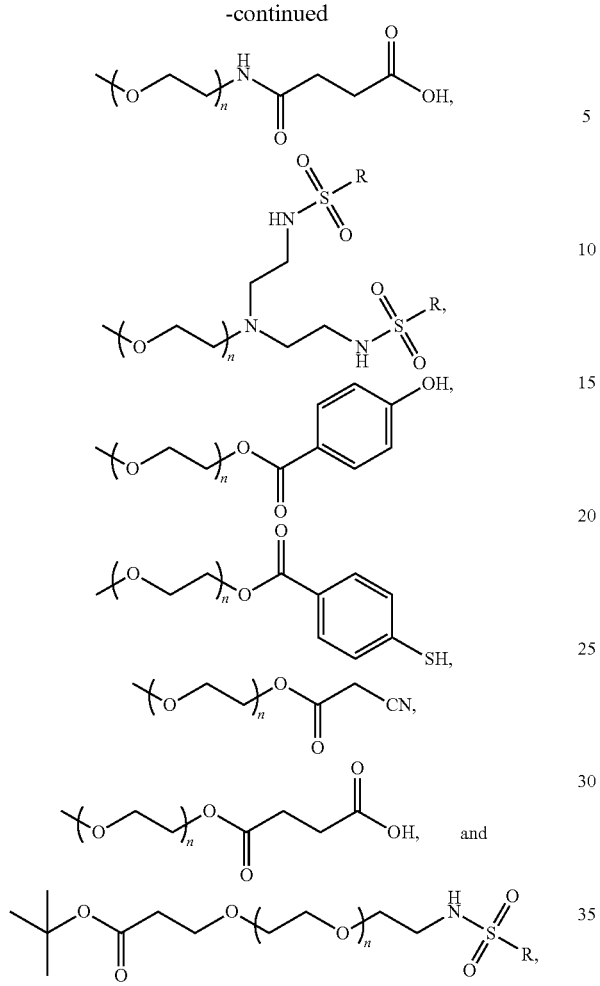

where n is selected to form a polymer having a molecular weight of about 1 kDa to about 20 kDa, and where R is selected from the group consisting of alkyl, cycloalkyl, aryl, heteroaryl, 2,2,2-trifluoroethyl, 3-[2,5-bis(bromomethyl)-4-methoxyphenoxy]-1-propyl, 3-(4-methoxyphenoxy)-1-propyl, phenylmethyl, nonafluoro-1-butyl, trichloromethyl, trifluoromethyl, 10-camphoryl, toluenyl, phenyl, 4-acetamidobenzenyl, 4-tert-butylbenzenyl, 4-bromobenzenyl, 2-carboxybenzenyl, 4-cyanobenzenyl, 3,4-dichlorobenzenyl, 3,5-dichlorobenzenyl, 3,4-dimethoxybenzenyl, 3,5-di(trifluoromethyl)benzenyl, 4-fluorobenzenyl, 4-methoxybenzenyl, 2-methoxycarbonylbenzenyl, 4-methylamidobenzenyl, 4-nitrobenzenyl, 4-trifluoromethyl-benzenyl, 4-trifluoromethoxybenzenyl, 2,4,6-trimethylbenzenyl, 5-chloro-2-thiophenyl, 2,5-dichloro-4-thiophenyl, 2-methyl-4-thiazolyl, 1-methyl-4-imidazolyl, 1-methyl-4-pyrazolyl, and 5-chloro-1,3-dimethyl-4-pyrazolyl.

40. A process according to claim 39, wherein the polymer is optionally bound to a hub molecule, wherein the hub molecule is derived from ethylene glycol, propylene glycol, α,ω-alkyl diols, phthalic acid, isophthalic acid, terphthalic acid, succinic acid, malonic acid, maleic acid, adipic acid, α,ω-alkyl dioic acids, acetylene dicarboxylic acid, glycerol, pentaerythitol, 1,2,4-benzenetriol, glucose, ethylenediamine tetraacetic acid, amino acids, 3- or 4-aminosalicylic acid, 1,3,5-benzene tricarboxylic acid, 1,3-diamino-2-hydroxypropane, glucosamine, and sialic acid.

41. A process according to claim 40, wherein the hub molecule portion of the conjugate is selected from:

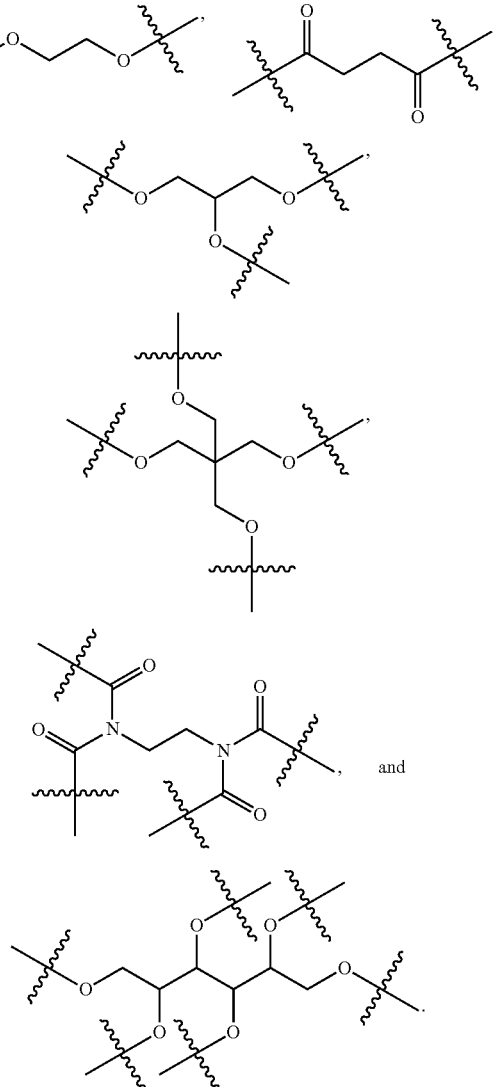

42. A process according to claim 40, wherein the polymer portion of the conjugate is selected from:

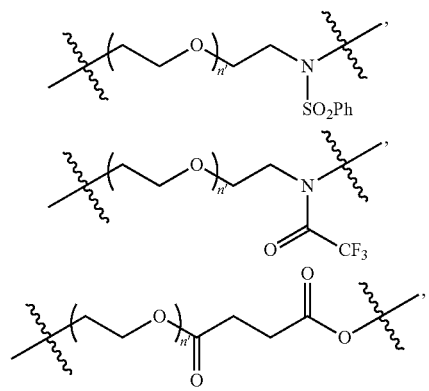

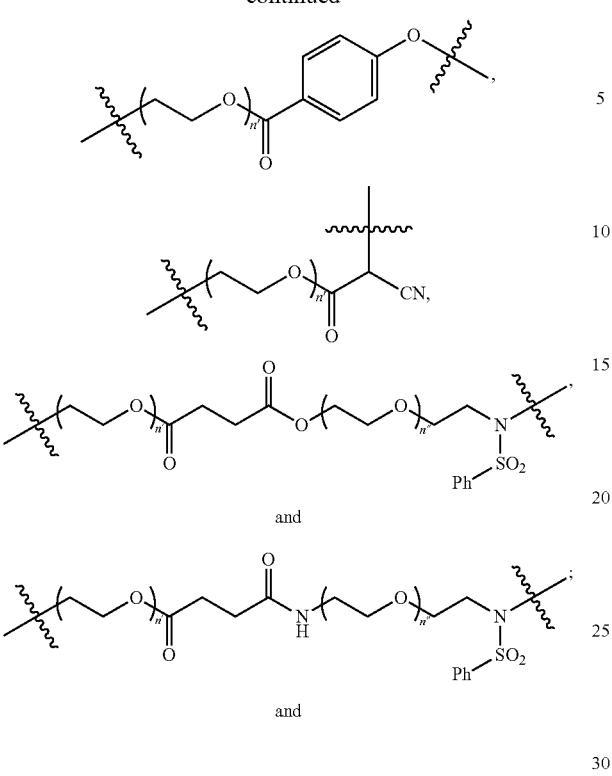
and
the hub molecule portion of the conjugate-is selected from:
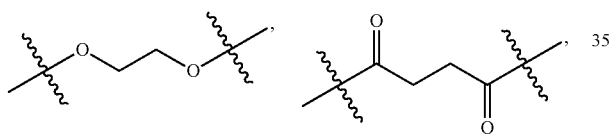
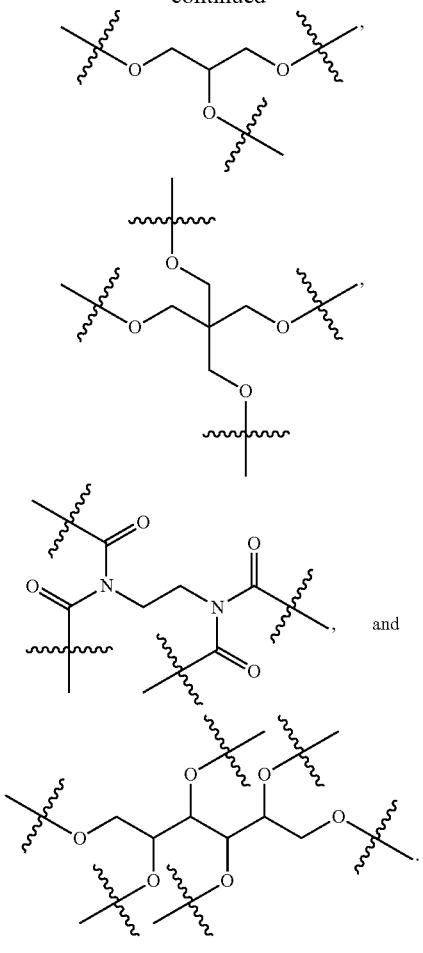
* * * * *